US011246520B2

(12) United States Patent
Clifford et al.

(10) Patent No.: US 11,246,520 B2
(45) Date of Patent: Feb. 15, 2022

(54) USING HEARTRATE INFORMATION TO CLASSIFY PTSD

(71) Applicant: Emory University, Atlanta, GA (US)

(72) Inventors: Gari Clifford, Atlanta, GA (US); Erik Reinertsen, Atlanta, GA (US); Amit Shah, Atlanta, GA (US); Shamim Nemati, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 138 days.

(21) Appl. No.: 16/469,001

(22) PCT Filed: Nov. 1, 2017

(86) PCT No.: PCT/US2017/059490
§ 371 (c)(1),
(2) Date: Jun. 12, 2019

(87) PCT Pub. No.: WO2018/111428
PCT Pub. Date: Jun. 21, 2018

(65) Prior Publication Data
US 2019/0313960 A1    Oct. 17, 2019

Related U.S. Application Data

(60) Provisional application No. 62/433,066, filed on Dec. 12, 2016.

(51) Int. Cl.
*A61B 5/024* (2006.01)
*A61B 5/00* (2006.01)
(Continued)

(52) U.S. Cl.
CPC .............. *A61B 5/165* (2013.01); *A61B 5/024* (2013.01); *A61B 5/316* (2021.01); *A61B 5/352* (2021.01); *A61B 5/7267* (2013.01)

(58) Field of Classification Search
CPC ......... A61B 5/165; A61B 5/352; A61B 5/024; A61B 5/318; A61B 5/316; A61B 5/02405
See application file for complete search history.

(56) References Cited

U.S. PATENT DOCUMENTS 7,177,675 B2    2/2007  Suffin et al.
2008/0269583 A1  10/2008  Reisfeld
(Continued)

FOREIGN PATENT DOCUMENTS

WO      2001085019 A2    11/2001
WO   WO-2016110804 A1 *  7/2016  ........... A61B 5/6814

OTHER PUBLICATIONS

International Search Report and Written Opinion for PCT/US2017/059490 dated Jan. 25, 2018.
(Continued)

*Primary Examiner* — Carl H Layno
*Assistant Examiner* — Aya Ziad Bakkar
(74) *Attorney, Agent, or Firm* — Thomas | Horstemeyer, LLP

(57) ABSTRACT

Systems, methods, and computer-readable media for classifying a PTSD status. In an embodiment, an example method for using a classifier can comprise receiving information from electrocardiography performed on an individual; determining features from the information; comparing the features to the a logistic regression classifier trained using features determined from median quiescent segments of RR interval information from individuals with and without PTSD, wherein the median quiescent segments are non-overlapping time periods of lowest median HR for each individual, and the features include one or more of the following: deceleration capacity (DC), low frequency (LF) power, very low frequency (VLF) power, and standard deviation of all normal RR intervals (SDNN); and determining a posttraumatic stress disorder (PTSD) status of the
(Continued)

individual based on the comparison of the features to the classifier, wherein the PTSD status is a severity of PTSD based on a probability of PTSD.

22 Claims, 32 Drawing Sheets

(51) Int. Cl.
  *A61B 5/316* (2021.01)
  *A61B 5/352* (2021.01)
  *A61B 5/16* (2006.01)

(56) References Cited

U.S. PATENT DOCUMENTS

2014/0121543 A1* 5/2014 Chan .................. A61B 5/0006
  600/483

2014/0330089 A1* 11/2014 Webb .................. A61B 5/0531
  600/301
2016/0249843 A1* 9/2016 Sugiyama ................ A61B 5/18
  600/521

OTHER PUBLICATIONS

Reinertsen, Erik, et al., Heart rate-based window segmentation improves accuracy of classifying posttraumatic stress disorder using heart rate variability measures. Physiol Meas. Jun. 2017 ; 38(6): 1061-1076. doi:10.1088/1361-6579/aa6e9c.

Shah, A. J., et al., Posttraumatic Stress Disorder and Impaired Autonomic Modulation in Male Twins. Biol Psychiatry. Jun. 1, 2013; 73(11): 1103-1110. doi:10.1016/j.biopsych.2013.01.019.

* cited by examiner

USING HEARTRATE INFORMATION TO CLASSIFY PTSD

CROSS-REFERENCE TO RELATED APPLICATIONS

This application is the 35 U.S.C. § 371 national stage application of PCT Application No. PCT/US2017/059490, filed Nov. 1, 2017, where the PCT claims the priority to and benefit of U.S. Provisional Patent Application Ser. No. 62/433,066, filed Dec. 12, 2016, the entire disclosures of which are hereby incorporated by reference in their entireties.

STATEMENT REGARDING FEDERALLY SPONSORED RESEARCH

This invention was made with Government support under grant numbers UL1TR000454, K24HL077506, R01HL68630, R01AG026255, K23 HL127251, and K24 MH076955, awarded by the National Institutes of Health (NIH). The Government has certain rights in the invention.

BACKGROUND

Post-traumatic stress disorder (PTSD) is a condition that can develop after exposure to traumatic events such as violence, natural disasters, or combat. Symptoms of this disorder include nightmares of the trauma, hypervigilance, difficulty sleeping, poor concentration, and avoidance of places, activities, or persons that remind the affected individual of the causal incident. PTSD can have devastating effects on life of an affected individual, and can lead to outcomes such as unemployment, homelessness, suicidality, and ultimately suicide in some severe cases. PTSD has a lifetime prevalence of about 8% in the US general population. The prevalence of PTSD is higher in developing or war-afflicted countries, in which people are exposed to more severe and/or more numerous traumas. The lifetime prevalence of PTSD is thus especially high in veterans, ranging from 6-30%.

Despite the increasing prevalence of PTSD occurrence, physicians currently lack objective standards by which to base diagnosis, treatment, and longitudinal disease prognosis within an individual experience symptoms of PTSD. Current methodology relies on subjective physician evaluation and patient self-reports, which can lead to unreliable diagnosis, unreliable treatments, and poor patient outcome. Accordingly, there is a need to address the aforementioned deficiencies and inadequacies.

SUMMARY

In accordance with the purpose(s) of the disclosure, as embodied and broadly described herein, the disclosure, in one aspect, relates to systems, methods, and computer-readable media for classifying a PTSD status and/or for training a classifier to classify a PTSD status are described herein.

Disclosed herein are systems configured to perform electrocardiography, the system comprising: a transducer that receives a heart signal comprising RR interval information from an individual, a plurality of individuals, or both, wherein the system is further configured to determine features from the information; compare the features to the classifier; and determine a posttraumatic stress disorder (PTSD) status of the individual based on the comparison of the features to the classifier.

Also disclosed are systems comprising: at least one processor; and a non-transitory computer readable medium coupled to the at least one processor and having instructions stored thereon that, when executed by the at least one processor, cause the at least one processor to determine features from electrocardiography information from at least one individual; compare the features to the classifier; and determine a posttraumatic stress disorder (PTSD) status of the at least one individual based on the comparison of the features to the classifier.

Also disclosed are monitoring systems for determining a posttraumatic stress disorder (PTSD) indicator, the monitoring system including one or more electronic processing devices that: obtain subject data indicative of a measured heart activity for the biological subject over a period of time; analyze the subject data to determine one or more quiescent segments of the period of time using the heart activity; analyze the subject data to determine at least one feature relating to the heart activity during a quiescent segment; apply the at least one feature to at least one computational model to determine a posttraumatic stress disorder (PTSD) indicator indicative of a PSTD status of the biological subject, the computational model embodying a relationship between PSTD and one or more features, the computational model being obtained by applying machine learning to test features derived from measured heart activity for one or more test subjects during at least part of test quiescent segments of a test period of time.

Also disclosed are one or more non-transitory computer readable media storing computer-executable instructions that, when executed by one or more processors, cause the one or more processors to perform operations comprising: comparing one or more features from electrocardiogrpahy information received from an individual to a classifier, wherein the electrocardiography information comprises a plurality of RR intervals and one or more quiescent segments, and wherein at least one of the features is based on at least one quiescent segment; determining a posttraumatic stress disorder (PTSD) status based on the comparison of the features to the classifier; and outputting the PTSD status.

Also disclosed are one or more non-transitory computer readable media storing computer-executable instructions that, when executed by one or more processors, cause the one or more processors to perform operations comprising: obtaining subject data indicative of a measured heart activity for the biological subject over a period of time; analyzing the subject data to determine one or more quiescent segments of the period of time using the heart activity; analyzing the subject data to determine at least one feature relating to the heart activity during a quiescent segment; applying the at least one feature to at least one computational model to determine a posttraumatic stress disorder (PTSD) indicator indicative of a PSTD status of the biological subject, the computational model embodying a relationship between PSTD and one or more features, the computational model being obtained by applying machine learning to test features derived from measured heart activity for one or more test subjects during at least part of test quiescent segments of a test period of time.

Also disclosed are methods for using a classifier, the method comprising: receiving measured heart activity from an individual, a plurality of individuals, or both, the information comprising RR interval information and one or more quiescent segments; determining features from the information; comparing the features to the classifier; and determining a posttraumatic stress disorder (PTSD) status of the individual based on the comparison of the features to the classifier.

Also disclosed are methods for determining a posttraumatic stress disorder (PTSD) indicator, the method including: obtaining subject data indicative of a measured heart activity for the biological subject over a period of time; analyzing the subject data to determine one or more quiescent segments of the period of time using the heart activity; analyzing the subject data to determine at least one feature relating to the heart activity during a quiescent segment; applying the at least one feature to at least one computational model to determine a posttraumatic stress disorder (PTSD) indicator indicative of a PSTD status of the biological subject, the computational model embodying a relationship between PSTD and one or more features, the computational model being obtained by applying machine learning to test features derived from measured heart activity for one or more test subjects during at least part of test quiescent segments of a test period of time.

Also disclosed are computer-implemented methods for using a classifier, the method comprising: receiving measured heart activity from an individual, a plurality of individuals, or both, the information comprising RR interval information and one or more quiescent segments; determining features from the information; comparing the features to the classifier; and determining a posttraumatic stress disorder (PTSD) status of the individual based on the comparison of the features to the classifier.

Also disclosed are computer-implemented methods for determining a posttraumatic stress disorder (PTSD) indicator, the method including: obtaining subject data indicative of a measured heart activity for the biological subject over a period of time; analyzing the subject data to determine one or more quiescent segments of the period of time using the heart activity; analyzing the subject data to determine at least one feature relating to the heart activity during a quiescent segment; applying the at least one feature to at least one computational model to determine a posttraumatic stress disorder (PTSD) indicator indicative of a PSTD status of the biological subject, the computational model embodying a relationship between PSTD and one or more features, the computational model being obtained by applying machine learning to test features derived from measured heart activity for one or more test subjects during at least part of test quiescent segments of a test period of time.

The details of one or more embodiments are set forth in the accompanying drawings which are given by way of illustration only, and the description below. Other features, aspects, and advantages will become apparent from the description, the drawings, and the claims. Like reference numbers and designations in the various drawings indicate like elements.

BRIEF DESCRIPTION OF THE DRAWINGS

FIG. 5A is a chart showing that low frequency (LF) power is lower in subjects with PTSD versus healthy controls for 24 hours of.

DETAILED DESCRIPTION

Figure 1:
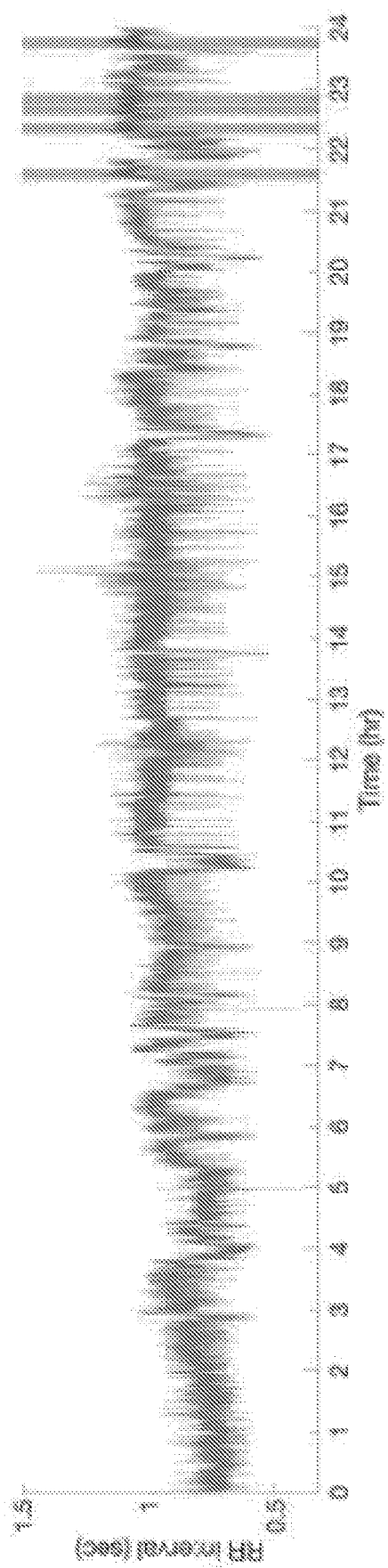
FIG. 1 illustrates a typical 24-hour RR tachogram with quiescent segments indicated by shaded regions.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a method comprising certain features or steps may include additional steps or features. Additionally, the term "comprising" is intended to include examples encompassed by the terms "consisting essentially of" and "consisting of" Similarly, the term "consisting essentially of" is intended to include examples encompassed by the term "consisting of."

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance may or may not occur, and that the description includes instances where said event or circumstance occurs and instances where it does not.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of cardiology, psychiatry, statistics, signal analysis, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, "heart activity" refers to, and includes one or more, measures such as heart rate, blood volume changes (e.g., in the microvascular bed of tissue); blood pressure; RR interval; quiescent segment; cardiac output; cardiac flow; arterial pressure; myocardial acceleration, impedance, flow, ejection fraction, degree of mitral regurgitation and tensiometric measurements; amplitude and direction of an electric heart vector (EHV); amplitude and direction of a magnetic heart vector (MHV); that can be determined, as appropriate, through measurement devices or techniques such as ECG, magnetocardiography, photoplethysmography, and/or devices comprising one or more sensors of cardiac function such as accelerometers, pressure sensors, oxymeters, flow sensors, and impendence sensors.

As used herein, "electrocardiography information" refers to electrocardiography data (ECG data, also known as EKG data) collected from one or more individuals (or subjects) using an electrocardiograph over a period of time.

As used herein, "quiescent segment" or "quiescent segments" refers to one or more non-overlapping 10-minute periods of lowest median HR or lowest average heartrate from a time series of electrocardiography information. As used herein, "quiescent segments" can also refer to 5 overlapping or non-overlapping periods of lowest median heartrate or lowest average heartrate. The duration of a quiescent segment can be 10 minutes, less than 10 minutes, or more than 10 minutes.

As used herein, "RR interval" is the duration between heartbeats, specifically the duration between the R phase of one heartbeat (R phase of the QRS complex) to the R phase of a second heartbeat immediately following the first heartbeat. RR intervals can be identified and analyzed from a time series of electrocardiography data (recorded/stored or in real-time), from one or more quiescent segments within a time series of electrocardiography data, or both.

As used herein, "PTSD status" refers to classification (into a PTSD class) of one or more individuals belonging to a PTSD or healthy group ("normal" group) or refers to severity of PTSD illness. A PTSD status may include PTSD-positive (e.g. diagnosed with, or classified as having, PTSD), PTSD-negative (e.g. determined by a professional healthcare provider as not having PTSD, or classified as not having PTSD), a severity of PTSD, and/or a probability of having PTSD. Multiple PTSD-positive groups or classes can exist, each with different disease severities and/or symptomology (for example: mild, moderate, severe, and the like).

Described herein are systems and methods to classify Post-Traumatic Stress Disorder (PTSD) status. Systems and methods as described herein can screen one or more individuals for PTSD diagnosis, illness severity, and/or PTSD treatment efficacy. Systems and methods as described herein can provide differential PTSD diagnosis in one or more individuals in conjunction with a healthcare provider. Systems and methods as described herein can capture heart activity (i.e. measured heart activity) from one or more individuals (also referred to as subjects); measured heart activity can be in the form of electrocardiography information, photoplethysmography information, or other methodology that provides information about the activity of the heart (heart rate and the like) and variability of heart rate activity from one or more individuals; can provide for patient-based monitoring of heart activity and PTSD status; and can provide for a reporting system leveraging data from one or more individuals. Systems and methods as described herein can provide for improved PTSD prediction accuracy using one or more features identified from heart rate information present in measured heart activity from one or more individuals.

Determining PTSD status traditionally relies on: 1) a physical examination to rule out physical problems that may be determining PTSD symptoms; 2) a psychological examination to discuss symptoms and life events that may have caused or triggered them; and 3) a comparison of results of psychological examination against criteria published in the Diagnostic and Statistical Manual of Mental Disorders by a physician.

Traditional methods for determining PTSD status as described above rely on physician interviews and patient self-evaluation with questionnaires, which are inherently subjective and variable. Subjective methodology as described above can lead to unreliable or misdiagnosis, development of treatment strategies which are a poor fit for the patient, and ultimately poor disease management. These traditional methods lack an objective standard criteria (internal or external) which can be used by physicians for PTSD status classification/determination, development of successful treatment strategies, and longitudinal disease monitoring. Accordingly, new PTSD classifications methods, systems, and strategies are desired.

The past few decades have seen an increase in PTSD research aimed at achieving better PTSD status classification by objective criteria, such as biomarkers. Biomarkers examined as criteria for PTSD classification include single-nucleotide polymorphisms within HPA-axis genes, messenger RNA levels, and genetic haplotype determination, among others. While these approaches have been promising, the interaction between genetics, environment, and adverse events which can lead to PTSD create a complex dynamic underlying PTSD etiology that presently precludes the use of biomarkers for PTSD status classification. As a result, objective standards for determining PTSD status classification remain elusive.

This disclosure provides a multivariate classifier separating PTSD patients and controls using HRV measures. Additionally, this disclosure considers the utility of thresholding on individual HRV measures to identify PTSD. In various aspects, this disclosure pertains to methods and devices comprising a PTSD classifier based on heart rate (HR) and HRV measures and a novel HR-based window segmentation to quantify illness severity.

When attempting to identify differences in autonomic function as measured by HRV, it is important to control for other factors such as stress/affect, physical activity, and cardiovascular or neurological disease not caused by PTSD. Doing so may not be easy, but evaluating HRV during sleep states may account for confounding from stress/affect and physical activity. Furthermore, HRV reductions due to PTSD may be greatest during the night, suggesting that analyzing data only during nocturnal sleep may improve classifier performance. However, HRV metrics vary by sleep stage due to changes in vagal and sympathetic activity during rapid eye movement (REM) sleep, light sleep, and deep sleep.

A novel method of controlling for activity using quiescent segments based on lowest median HR for each subject is described herein. This segmentation approach may reduce random error from mental and physical activity, highlight the involvement of the autonomic nervous system, and approximate restfulness in the absence of validated sleep stage data.

The present disclosure provides methods and devices for: 1) identifying one or more quiescent segments within heart-rate information from one or more individuals; 2) identifying features from HR and HRV measures indicative of PTSD (e.g. in veteran male twins from the Vietnam era using 24-hour Holter ECG recordings); 3) using these features to train a multivariate classifier whose output—a probability of membership in either the PTSD or control group—could potentially be used as a proxy for illness or illness severity (possibly, but not necessarily, after clinical diagnosis of PTSD), and 4) improving classifier performance using a windowed segmentation method on RR interval data to account for potential confounders of HRV measures.

Systems and methods as described herein are an improvement on existing systems and methods for determining PTSD status and provide for improvements in systems and methods relating to determining PTSD status. Systems and methods described herein provide improvements in PTSD classification by analyzing features of physiological measurements under autonomic nervous system. The features which are present in physiological measurements, such as heart rate and heart rate variably, represent the output of the integration of PTSD risk factors: genetics, environment, and adverse events underlying PTSD etiology. Evaluation of physiological measurements can represent a more accurate objective assessment of PTSD status by examining the integration of PTSD risk factors together, rather than on the individual level (such as with genotyping and blood tests). These features, once analyzed, can be compared to a classifier and PTSD status assessed without the reliance on subjective measures such as questionnaires and psychological assessments solely. The systems and methods described herein therefore provide for the improved objective classification of PTSD, which has been previously unobtainable using other methods, such as biomarkers.

Furthermore, systems and methods herein provide for improvements in hardware performance. Feature identification in information from measured heart rate activity is computationally slow. As described herein, a subset of features have been identified which can reliably predict PTSD classification, leading to an optimized feature set within measure heart activity (such as ECG information or photoplethysmography information) for PTSD. Model training and comparison with the optimized subset[s] of features as described herein improve computational performance by reducing computational load on hardware components as compared to identification and comparison with a larger feature set.

Methods and systems as described herein can record heart activity information from one or more individuals (i.e. measured heart activity). Methods and systems as described herein can record heart activity information from multiple individuals or a plurality of individuals. Heart activity information or measured heart activity can be electrocardiography information and can be detected using a heart activity monitor, such as an electrocardiograph, examples of which may be, without limitation, a heart rate monitor or a Holter monitor. Heart activity information or measured heart activity can also be in other forms, such as photoplethysmography information detected using a heart activity monitor, such as one or more devices with low cost optical sensors, examples of which may be, without limitation, wrist-worn consumer wearables. In systems and methods as described herein, cardiographs configured to collect electrocardiography information from an individual or photoplethysmography devices can be incorporated in a variety of physical devices, such as wearables configured to fit around the wrist or chest of an individual.

Heart activity can be detected and recorded from an individual (or a subject) or plurality of individuals for 24 hours. Heart activity information can be detected and recorded from an individual (or a subject) or plurality of individuals for more than 24 hours. Heart activity information can be collected from one or more individuals while the one or more individuals are awake or asleep. Features from measured heart activity can be identified and/or analyzed from stored information, or can be identified/analyzed in real-time as it is collected. As used herein, electrocardiography information can be heartrate information or heart activity, and vice versa.

Measured heart activity can comprise a series of RR intervals and/or one or more quiescent segments, and quiescent segments within electrocardiography or heartrate information can be identified using systems and methods as described herein. One or more quiescent segments can be identified in the measured heart activity. 5 quiescent segments each with a duration of 10 minutes can be identified. In embodiments, 1-5 quiescent segments can be identified. In embodiments, 2-4 quiescent segments can be identified. In embodiments, 3 quiescent segments can be identified. In embodiments, more than 5 quiescent segments can be identified. RR intervals can be taken from the median quiescent segment[s]. Quiescent segments can be non-overlapping or overlapping.

Following collection of heart activity, the information (measured heart activity) can be cleaned before processed by systems and methods as described herein. RR intervals in measured heart activity 24 hours past the start of information collection can be discarded; RR intervals greater than 1.5, less than 0.33, or more than 20% shorter or longer than the previous RR interval or the overall mean RR interval can be discarded.

Measured heart activity can contain features relating to heart activity. Features can be identified and extracted from the heart activity or measured heart activity. Features relating to heart activity can be statistical features and can be one or more of: mode, median, standard deviation, interquartile range, skewness, and kurtosis of RR intervals (individually or in combination). Features can be detected within the entirety of the measured heart activity, within the RR intervals of the quiescent segment[s], or both. Features present in heart activity or measured heart activity can be power spectral features such as AC, DC, total power, and the standard deviation of normal-to-normal intervals (SDNN). Features can be DC, low-frequency (LF) power (described below), very low frequency (VLF) power (described below), and SDNN. Features can be power spectral features such as a multi-scale entropy; a standard deviation of average pulse intervals; and, square root of the mean of the squares of differences between adjacent pulse intervals; acceleration capacity (AC); and, deceleration capacity (DC). Any one or more of the above features can be present in heart activity or measured heart activity.

Power spectral measures can be determined from heart activity or measured heart activity collected from one or more individuals. Power spectral measures can be determined with methods such as a fast fourier transform with a Parzen window. The power spectrum can be integrated over one or more frequency bands. The power spectrum can be integrated over one or more of: an ultra-low frequency band (ULF; <0.0033 Hz), a very low frequency band (VLF; 0.0033-0.04 Hz); a low frequency band (LF; 0.04-0.15 Hz); and a high frequency band (HF; 0.15-0.4 Hz). These frequency bands can measure and provide proxies for function of the renin-angiotensin, sympathetic, and parasympathetic cardiovascular control systems. Total power incorporating a full spectrum of up to 0.4 Hz can also be estimated.

Acceleration capacity (AC) and deceleration capacity (DC) can also be identified and extracted from the measured heart activity. Phase rectified signal averaging (PRSA) can be performed to quantify acceleration/deceleration capacity. Heartbeat interval shortenings can be used as anchors for acceleration-related PRSA signals. Heartbeat interval lengthening's can be used as anchors for deceleration-related PRSA signals. Sampling frequency for AC and DC measurements can be 512 Hz. Window length for AC and DC measurements can be 30 elements. AC can be higher in individuals with a current PTSD status classification compared to normal, non-pathologic individuals. DC, LF, and SDNN each can be lower in individuals with a current PTSD status classification compared to normal, non-pathologic, individuals. Although PRSA is used as an example, other HRV and/or mobility signals and signal variability approaches (such as the use of Hjorth parameters, for example) can be used.

Features as described above can be used to train a classifier (also referred to herein as a model or the model). The classifier can be a binary classifier, the output of which being the probability of having membership in a PTSD group or control group. Without intending to be limiting, a classifier as described herein can be a logistic regression classifier, a support vector machine classifier, or other classifiers. The classifier may be any one of many methods for classification or regression known in the art. The model may be an artificial neural network, a Bayesian graphical model, a Gaussian process, a logistic regression, a support vector machine, a decision tree, a hidden Markov model, or k-nearest neighbor. K-fold cross-validation may be used.

Regularization can be performed on the electrocardiography information to reduce coefficient values for co-linear or non-predictive features and to create a sparser and more generalizable model. Regularization can be L1 (LASSO), L1-L2 (elastic net), and/or L2 (ridge). Additional classifier refinement can be undertaken, such as maximum likelihood estimation by methods such as quasi-Newton limited-memory Broyden-Fletcher-Goldfarb-Shanno updating and grid searching to assess combination of features. A grid search can be performed to select an optimal value of a parameter $\lambda$ that maximizes the test set out of sample area under the receiver operating characteristic curve (AUC). Performance metrics of the classifier can include AUC, accuracy, sensitivity, specificity, positive predictive value (PPV), and negative predictive value (NPV).

Following collection by a heart activity monitor (such as electrocardiograph or photoplethysmography device), measured heart activity can be transmitted to a computing device or plurality of computing devices across a wired or wireless connection. One transmitted to the computing device or plurality of computing devices, the measured heart activity can be stored (ie recorded) by methods and systems as described herein, analyzed, or both. Logic executable on a computer readable storage medium can comprise instructions which can aid in feature detection from the measured heart activity, model classification, comparison of features to a classifier, and output of the result of any comparisons, feature detections, and/or analysis. Additional system components are described in further detail below.

Figure 7:
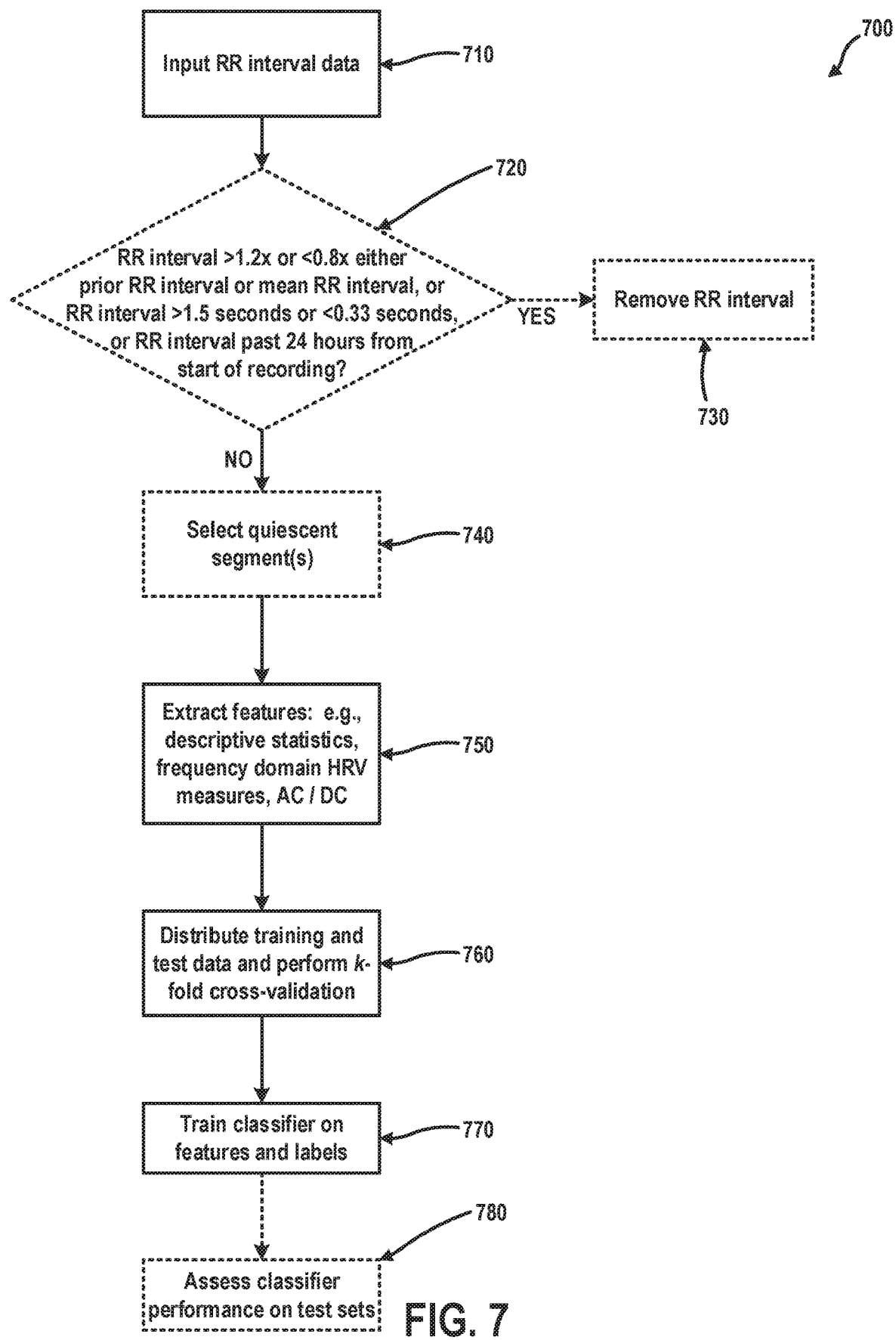
FIG. 7 is a flow diagram of an example method for training a classifier that classifies a PTSD status.
Figure 8:
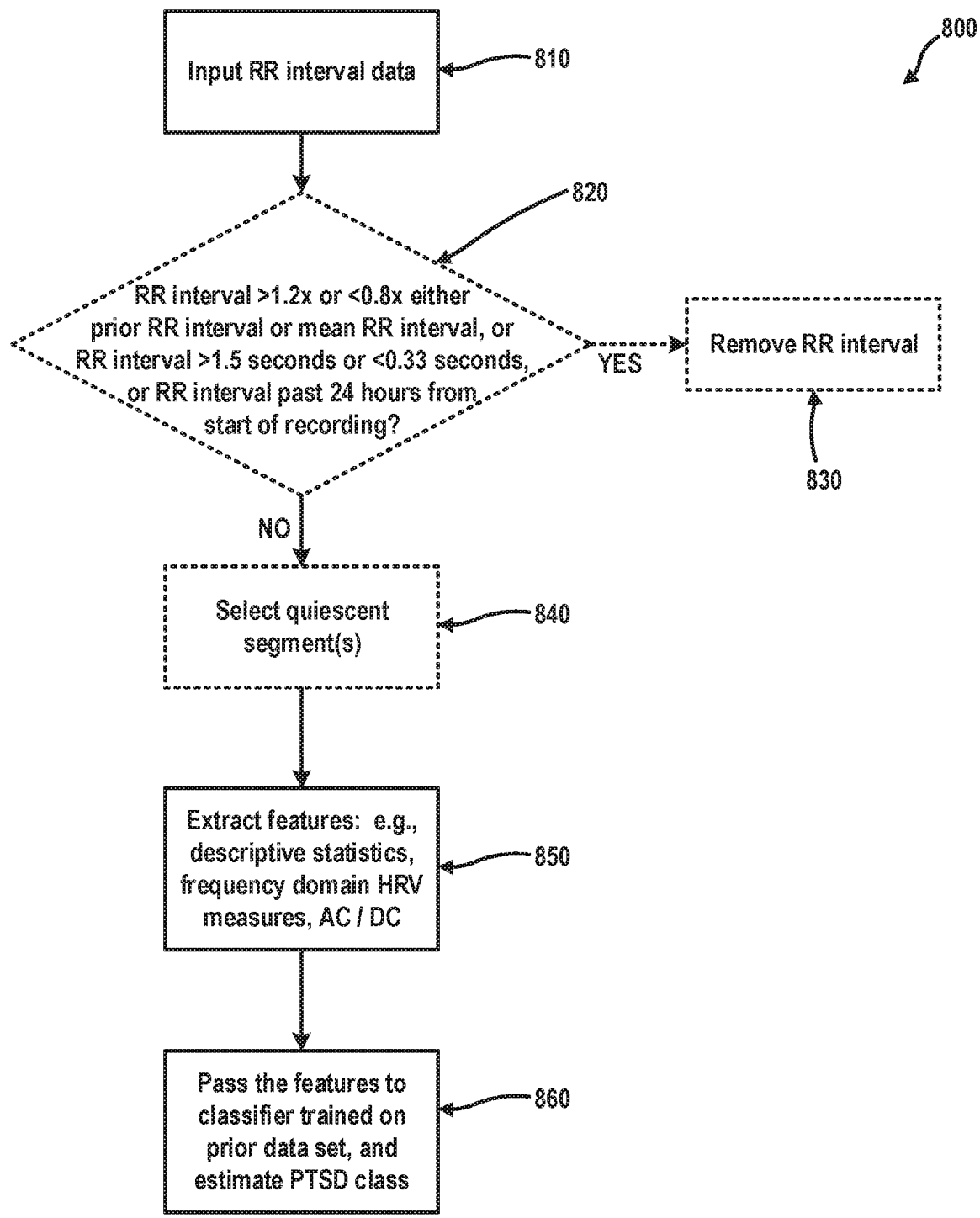
FIG. 8 is a flow diagram of an example method for classifying PTSD.

The following is a method for determining or selecting a quiescent segment according to one or more embodiments, and the following method may be used at 720 of FIG. 7 or at 820 of FIG. 8 for selecting quiescent segments. The following example uses an electrocardiograph and electrocardiography information, but one skilled in the art would appreciate that other collection devices (such as wearables incorporating photoplethysmography) and photoplethysmography can be used.

Using a sliding 10-minute window on information from electrocardiography 1535 performed on an individual 1010, find five non-overlapping 10-minute periods of lowest median HR; these five periods are quiescent segments.

RR interval data from the median quiescent segment of these five periods may be used to calculate HRV features, but the embodiments are not limited thereto. The median quiescent segment may be determined by taking the median quiescent segment in an ordering of the five quiescent segments by the median heart rate of each quiescent segment. The median quiescent segment may be determined by taking the median quiescent segment in an ordering of the five quiescent segments by the average heart rate of each quiescent segment.

FIG. 7 is a flow diagram of an example method (700) for training a classifier that classifies a PTSD status. First, RR interval data is input (710). The RR interval data may be measured heart activity 1535 performed on one individual, multiple individuals, or both. RR interval data may be excluded if a duration of a recording of RR interval data does not meet a threshold (e.g. less than 24 hours). The RR interval data may be input to a computing device. Optionally, second, at 720, an RR interval is removed (730) if any of the following are true: the RR interval is greater than 1.2 times or less than 0.8 times either the prior RR interval or a mean RR interval, the RR interval is greater than 1.5 seconds or less than 0.33 seconds, or the RR interval occurs more than 24 hours past the start of recording. Optionally, third, at least one quiescent segment is selected (740). Fourth, features are extracted (750) from the RR interval data. The features may include descriptive statistics, frequency domain HRV measures, AC, DC, the phase of the median quiescent window (time of day normalized to radians), basic RR interval statistics (mean, median, mode, standard deviation, interquartile range, skewness, and kurtosis), power spectral measures (VLF, LF, HF, total power), and/or other measures of the distribution of RR intervals (NNN, MNN, PNN, PNN50, RMSSD, and/or SDNN. Fifth, training and test data are distributed, and k-fold cross-validation is performed (760). Sixth, a classifier is trained (770) on the features and labels. The classifier may be trained using a computing device. Optionally, seventh, the classifier's performance is assessed (780) on test sets.

FIG. 8 is a flow diagram of an example method (800) for classifying a PTSD status. First, RR interval data is input (810). The RR interval data may be information from measured heart activity 1535 from an individual (i.e. a subject). RR interval data may be excluded if a duration of a recording of RR interval data does not meet a threshold (e.g. less than 24 hours). The RR interval data may be input to a computing device. Optionally, second, at 820, an RR interval is removed (830) if any of the following are true: the RR interval is greater than 1.2 times or less than 0.8 times either the prior RR interval or a mean RR interval, the RR interval is greater than 1.5 seconds or less than 0.33 seconds, or the RR interval occurs more than 24 hours past the start of recording. Optionally, third, at least one quiescent segment is selected (840). Fourth, features are extracted (850) from the RR interval data. The features may include descriptive statistics, frequency domain HRV measures, AC, DC, the phase of the median quiescent window (time of day normalized to radians), basic RR interval statistics (mean, median, mode, standard deviation, interquartile range, skewness, and kurtosis), power spectral measures (VLF, LF, HF, total power), and/or other measures of the distribution of RR intervals (NNN, MNN, PNN, PNN50, RMSSD, and/or SDNN. Fifth, the features are passed to the classifier trained on a prior data set, and a PTSD class is estimated (860).

Figure 10:
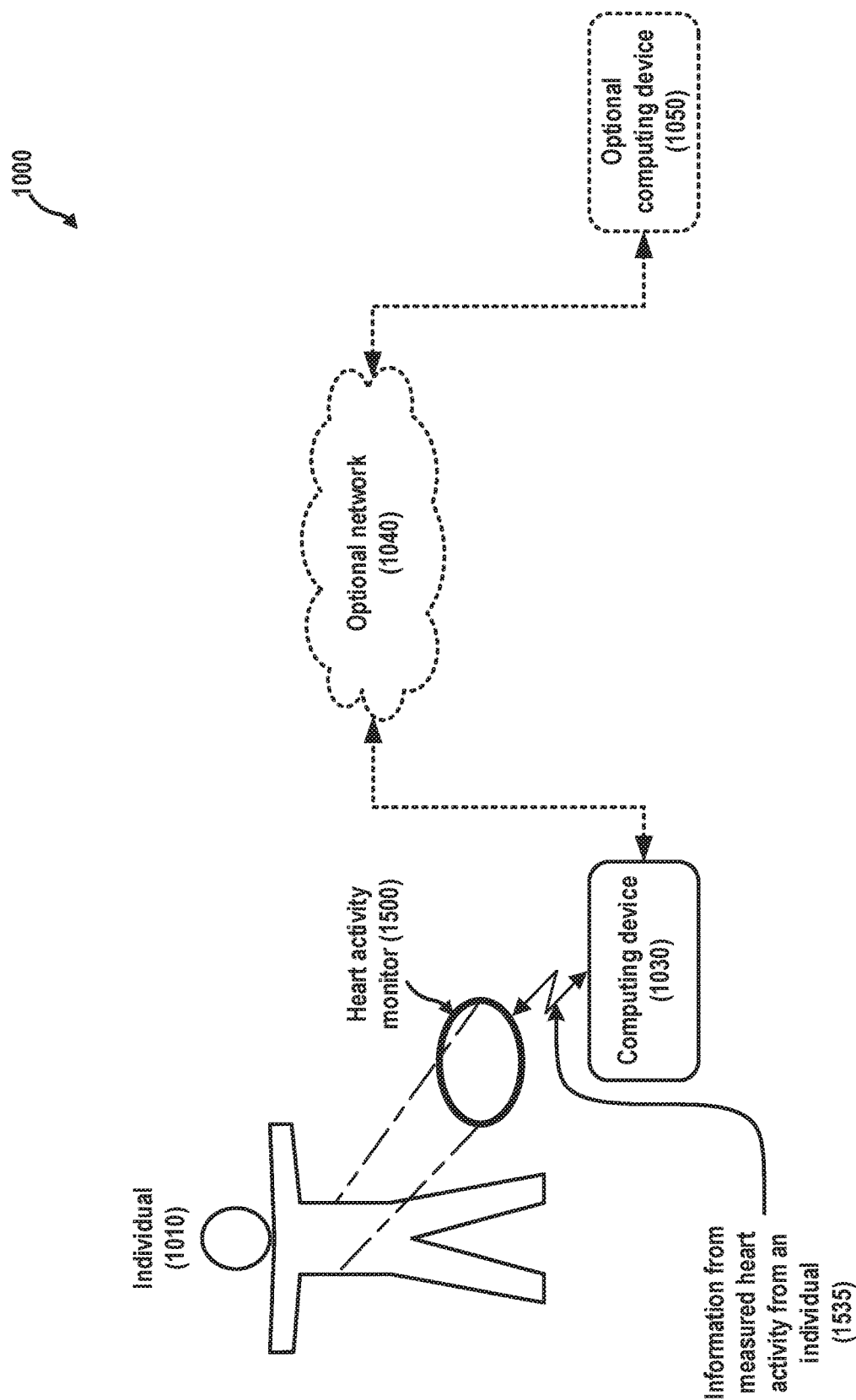
FIG. 10 is a high-level diagram of a system for classifying PTSD and/or for training a classifier to classify PTSD.

FIG. 10 is a high-level diagram of a system (1000) for classifying a PTSD status and/or for training a classifier to classify a PTSD status. Individual 1010 wears a heart activity monitor 1500 to measured heart activity from the individual (1535). The heart activity monitor 1500 may be, without limitation, a heart rate monitor or a Holter monitor, or a wearable incorporating sensors for photoplethysmography. The heart activity monitor 1500 may be an adhesive-type heart activity monitor that, when worn, looks similar to a large adhesive bandage. The heart activity monitor (1500) may transmit information from measured heart activity (1535) from an individual (1010) to a computing device 1030. The computing device 1030 may be, for example, a personal computer, a smartphone, or a tablet computer. The heart activity monitor (1500) may transmit information measured heart activity from an individual (1535) to the computing device 1030 wirelessly using a protocol such as Bluetooth or Bluetooth Smart (Bluetooth low energy). Other protocols may include a proprietary protocol or a protocol based on IEEE 802.15.4 such as Zigbee. In at least one embodiment, the heart activity monitor 1500 may include a SIM card and circuitry to communicate with a base station in a cellular network. In at least one embodiment, the heart activity monitor 1500 may communicate with a platform in the cloud such as Philips Healthsuite or Samsung ARTIK Cloud.

In at least one embodiment, the computing device 1030 (e.g. OnHub SRT-AC1900 by Asus and Google) can receive information via IEEE 802.15.4 or Bluetooth and transmit information to another computing device (e.g. a smartphone or a computing device in the cloud) via, for example, IEEE 802.11ac or over a wide area network using, e.g., a LTE connection or Ethernet. A protocol such as Bluetooth Smart or a protocol based on IEEE 802.15.4 generally requires less power than a protocol like IEEE 802.11ac, thereby helping preserve battery life of a computing device 1030 or an electrocardiograph 1500. The heart activity monitor (1500) may have the ability to switch between or among different wireless protocols to reduce power demand or increase wireless range, depending on the capabilities of the computing device(s) to which it transmits information. The heart activity monitor 1500 may be connected to the computing device 1030 by an Ethernet connection or a wired connection (e.g. USB). In at least one embodiment, the computing device 1030 is integral with the heart activity monitor 1500. In at least one embodiment, the computing device 1030 is a computing device 1220 accessed by a healthcare provider involved in the diagnosis or reporting of a PTSD status to the individual 1010.

In at least one embodiment, the computing device (1030) may transmit information over a network (1040) (e.g. the Internet) to another computing device (1050). The information may include measured heart activity 1535 from the individual 1010, features determined from information from measured heart activity 1535 performed on the individual 1010, a PTSD status, and/or RR interval information. The computing device 1050 may be part of software as a service (SaaS) or cloud computing infrastructure. In at least one embodiment, the computing device 1050 is a computing device 1220 accessed by a healthcare provider involved in the diagnosis or reporting of a PTSD status to the individual 1010.

Computing device (1030) may implement all or a portion of measured heart activity processing unit (1100). Computing device (1050) may implement all or a portion of measured heart activity processing unit (1100).

As used herein, information from measured heart activity includes information in a signal received by a heart activity monitor and information transmitted or stored by a heart activity monitor. Information from measured heart activity may include an analog signal or data resulting from converting an analog signal to digital information.

As used herein, a PTSD status may include PTSD-positive (e.g. diagnosed with, or classified as having, PTSD), PTSD-negative (e.g. determined by a professional healthcare provider as not having PTSD, or classified as not having PTSD), a severity of PTSD, and/or a probability of having PTSD.

Figure 11:
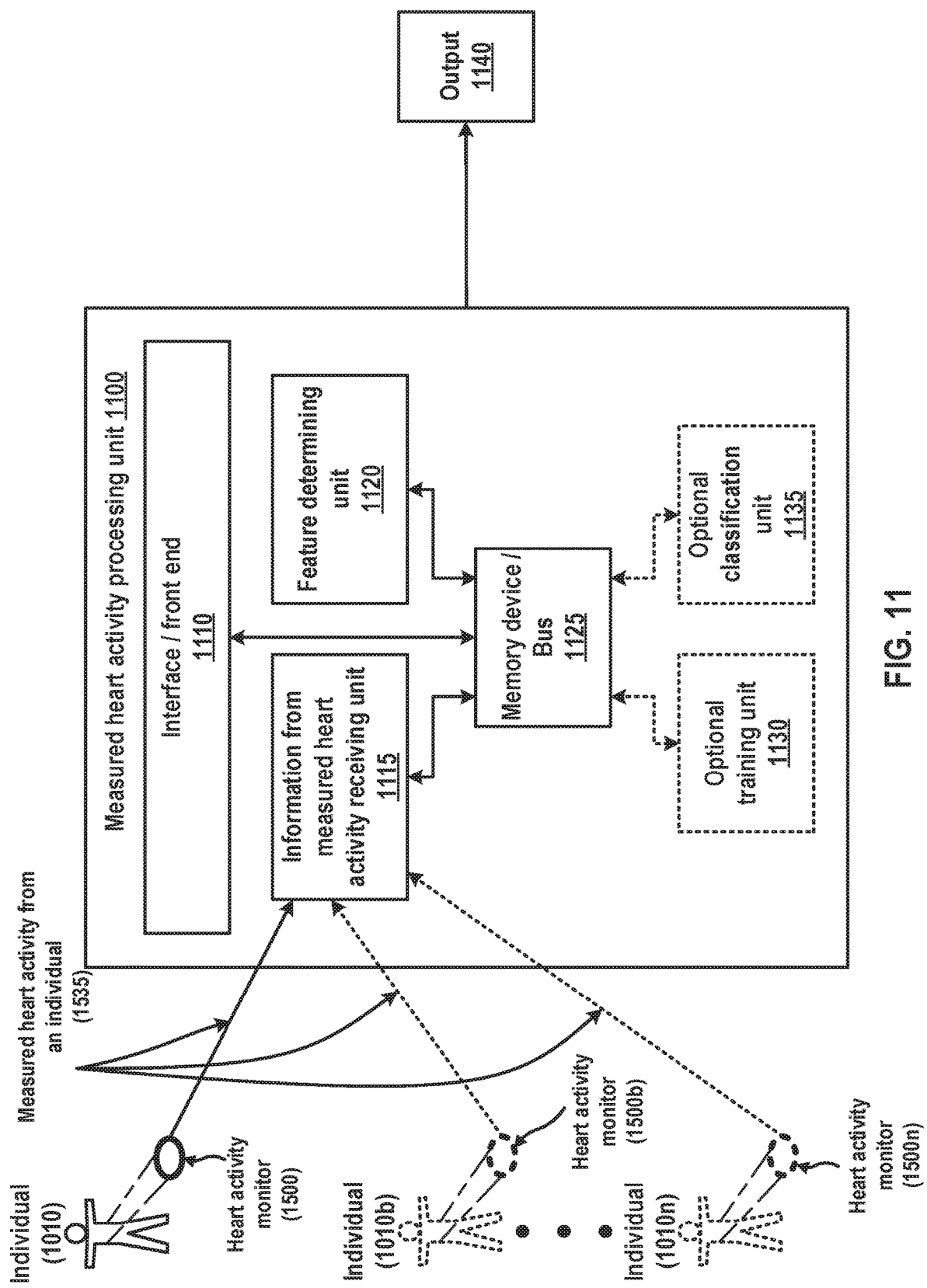
FIG. 11 is a block diagram of a measured heart activity processing unit according to at least one embodiment.

FIG. 11 is a block diagram of a measured heart activity processing unit (1100) according to at least one embodiment. A measured heart activity processing unit (1100) may include interface/front end (1110), information from measured heart activity receiving unit (1115), feature determining unit (1120), and a memory device/bus (1125). Measured heart activity processing unit (1100) may optionally include an optional training unit (1130). Measured heart activity processing unit (1100) may optionally include an optional classification unit (1135).

The measured heart activity processing unit (1100) receives information from measured heart activity 1535 from an individual (1010). The measured heart activity processing unit (1100) provides an output (1140). The output (1140) may be a PTSD status, a severity of PTSD, a probability of PTSD, quiescent segments, RR interval data, an error message, a feature determined or extracted by the feature determining unit (1120), etc. The output (1140) may be a model, including a model trained or learned by the optional training unit (1130). The output (1140) may be a machine learning model, including a machine learning model trained or learned by the optional training unit (1130). The output (1140) may be displayed on a display. A PTSD status may be determined rapidly, by using a computing device, upon completion of receiving information from measured heart activity 1535 from an individual 1010. A PTSD status may be determined securely and rapidly, by using a computing device 1220, upon request by a healthcare provider.

Information from measured heart activity receiving unit (1115) receives information from measured heart activity 1535 from an individual (1010). The information from the measured heart activity receiving unit (1115) may provide the information from measured heart activity 1535 from an individual (1010) to the memory device/bus (1125).

Feature determining unit (1120) determines or extracts features from the information from the measured heart activity 1535 from the individual (1010). The features may include or be based on at least one quiescent segment. The feature determining unit (1120) may determine a quiescent segment. The features may include RR interval information, quiescent segments of RR interval information, lowest median HR, acceleration capacity (AC), deceleration capacity (DC), total power, low frequency (LF) power, very low frequency (VLF) power, standard deviation of all normal RR intervals (SDNN), a phase of a median quiescent segment window, a mode of RR intervals, a median of RR intervals, a standard deviation of RR intervals, an interquartile range of RR intervals, a skewness of RR intervals, a kurtosis of RR intervals, a PTSD status, a severity of PTSD, and/or a probability of PTSD. The feature determining unit (1120) may determine a feature vector including one or more features. The feature determining unit (1120) may provide features or feature vectors to the memory device/bus (1125).

The features may be determined using a computing device. A feature vector may comprise a data structure with at least one value determined by the computing device based the information from measured heart activity 1535 from an individual 1010. Each feature vector may be associated with a label. The label may be a classification which a model will provide as output when the model is used as a classifier for classification or determination of a PTSD status. The label may be, without limitation, a PTSD status, a severity of PTSD, a probability of PTSD, or a quiescent segment.

The measured heart activity processing unit (1100) may optionally include an optional training unit (1130). The optional training unit may receive from the memory device/bus 1125 the features or feature vectors that the feature determining unit 1120 provided to the memory device/bus 1125. The optional training unit may further receive a label associated with each feature or feature vector. The optional training unit 1130 may train a model or a machine learning model. The optional training unit 1130 may use a machine learning algorithm implemented on a computing device to train the model or machine learning model.

In the case that the measured heart activity processing unit 1100 includes the optional training unit 1130, the information from measured heart activity receiving unit 1115 may receive information from electrocardiography 1535 performed on individuals 1010, 1010b, ..., 1010n, n≥2. The memory device/bus 1125 may provide the information from measured heart activity 1535 from individuals 1010, 1010b, ..., 1010n, to the feature determining unit 1120. The feature determining unit 1120 may determine features or a feature vector related to each individual 1010, 1010b ... 1010n, and may receive as input a label associated with each individual 1010, 1010b ... 1010n. The memory device/bus 1125 may provide the features or feature vector related to each individual 1010, 1010b ... 1010n, and any respective labels, to the optional training unit 1130.

A model (e.g. machine learning model) may be a kernel or learned classifier, and determining features and comparing a feature vector to the model may involve computational complexity exceeding what is feasible for a person. That is, some data classification problems, such as determining a PTSD status or training a classifier that determines a PTSD status, may require a technical solution (e.g. implementation on a computing device) due to their computational complexity. This technical solution may lead to the technical effect of reporting a PTSD status based on features determined from information from measured heart activity 1535 from an individual 1010.

An ensemble of models may be used via boosting or another ensemble method. The model may be any one of many methods for classification or regression known in the art. The model may be an artificial neural network, a Bayesian graphical model, a Gaussian process, a logistic regression, a support vector machine, a decision tree, a hidden Markov model, or k-nearest neighbor. K-fold cross-validation may be used. The optional training unit (1130) may provide the model to the memory device/bus (1125).

The optional classification unit (1135) classifies information from measured heart activity 1535 from an individual 1010 by comparing features or a feature vector associated with the information from measured heart activity 1535 from the individual 1010 to the model. The model may be a model trained by the optional training unit (1130). The optional classification unit (1135) may provide the output (1140). The optional classification unit (1135) may use an unsupervised learning method such as clustering or hierarchical clustering to classify features or a feature vector. The optional classification unit (1135) may provide the classification or output (1140) to the memory device/bus (1125).

Note the training unit (1130) is optional. The model (e.g. machine learning model) may be provided as input to the measured heart activity processing unit 1100 in an embodiment where the model is a predetermined model.

The memory device/bus (1125) may comprise a system bus, memory bus, volatile storage, and/or non-volatile storage. Further, the memory device/bus (1125) may comprise a bus connecting multiple computers. The memory device/bus may connect computers via a network or Internet connection. That is, the various components in the heart activity processing unit 1100 may be part of a distributed computing system, and the memory device/bus (1125) may connect the various components in the distributed computing system. Thus, the memory device/bus (1125) may include a network connection and equipment such as routers, gateways, network adapters, base stations (e.g. eNodeB), etc., to enable the various components of the measured heart activity processing unit 1100 to communicate and perform methods, including the methods described herein. The memory device/bus (1125) communicates information between or among various portions of the measured heart activity processing unit 1100, including the interface/front end (1110). The memory device/bus (1125) may provide the output (1140) to e.g. the individual 1010, a healthcare provider 1240, or the interface/front end (1110).

Interface/front end (1110) may comprise an output device such as a display (e.g. monitor) or a speaker, etc. Interface/front end (1110) may further comprise an input device such as a keyboard, mouse, microphone, etc. Interface/front end (1110) may be web-based. Interface/front end (1110) may be the interface/front end (1230). Interface/front end (1110) may report or indicate the output (1140).

Figure 12:
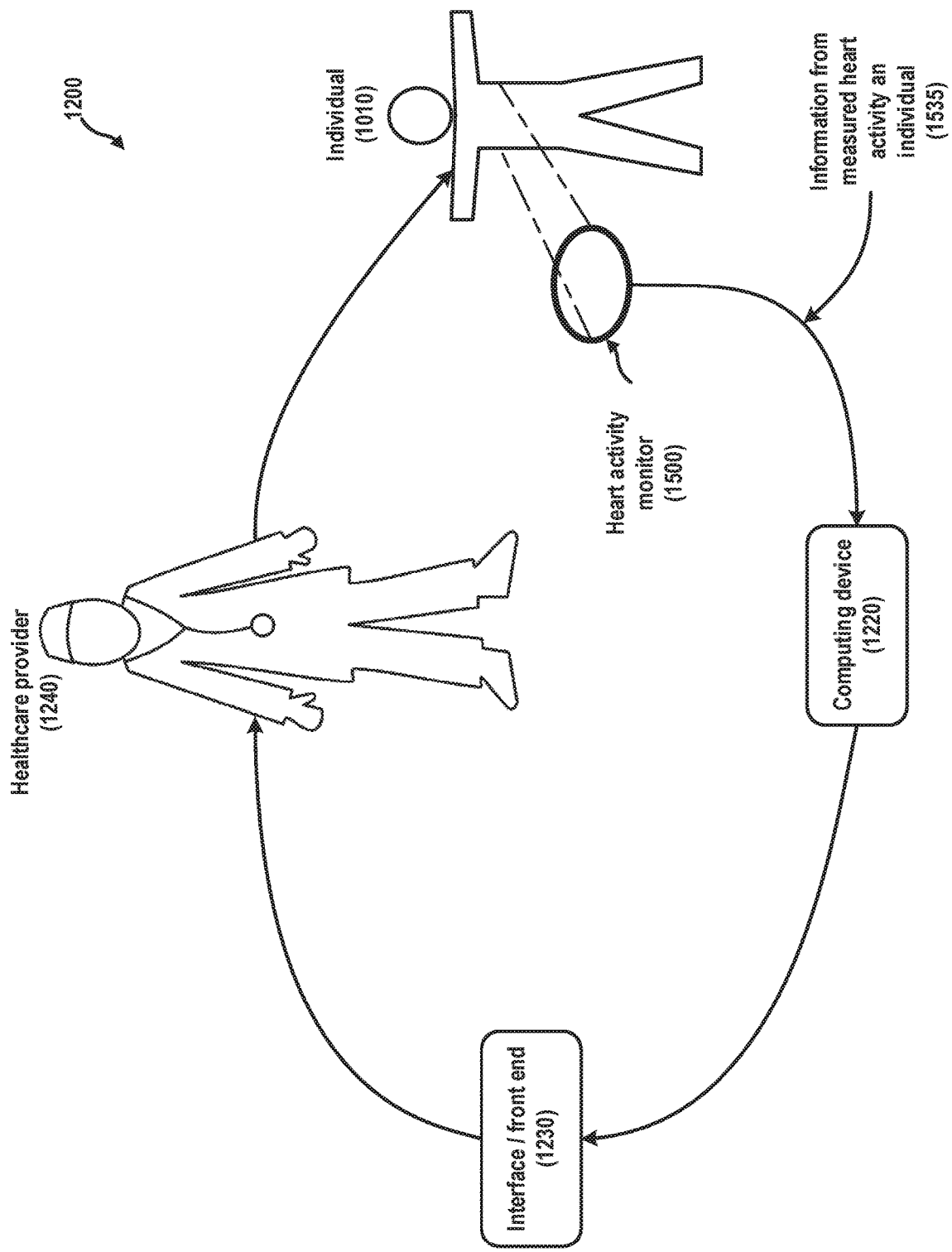
FIG. 12 is a high-level block diagram of a system and/or method for professional monitoring of a PTSD status according to at least one embodiment.

FIG. 12 is a high-level block diagram of a system and/or method (1200) for professional monitoring of a PTSD status according to at least one embodiment. Information from measured heart activity 1535 from the individual 1010 using the heart activity monitor 1500 is provided to a computing device 1220. The computing device 1220 may implement the measured heart activity processing unit 1100. Note given the structure of memory device/bus 1125, the computing device 1220 may comprise multiple computing devices, including computing device 1030 and/or 1050. Computing device 1220 may provide information (e.g. output 1140) to the interface/front end 1230. Computing device 1220 may be part of, or in communication with, a cloud platform such as Philips Healthsuite or Samsung ARTIK Cloud.

The interface/front end (1230) may be a secure interface compliant with privacy or healthcare regulations such as HIPAA. The interface/front end (1230) may be the interface/front end (1110).

The healthcare provider 1240 may obtain information (e.g. output 1140) from the interface/front end (1230). For example, the healthcare provider 1240 may interpret information from measured heart activity 1535 from the individual 1010, features or a feature vector determined by the feature determining unit 1120, and/or a classification determined by the classification unit 1135. The healthcare provider 1240 may determine or diagnose a PTSD status based on the information from the interface/front end (1230). The healthcare provider 1240 may provide information (e.g. output 1140) to the individual 1010.

In certain aspects, systems and methods as described herein can provide data for PTSD treatment efficacy over time. In at least one embodiment, the healthcare provider 1240 provides ongoing monitoring to the individual 1010. The healthcare provider 1240 may monitor the individual's 1010 PTSD severity or status over the course of multiple days or multiple healthcare provider visits. The healthcare provider 1240 may receive information from measured heart activity 1535 from the individual 1010 or output 1140 in real-time. Therefore, in the case of an emergent PTSD issue, healthcare provider may be advised by the interface/front end (1230) of the emergent PTSD issue rapidly. The healthcare provider 1240 may provide a PTSD intervention which may be administered at the healthcare provider's 1240 location (e.g. hospital or out-patient clinic) and/or the individual's 1010 location (e.g. home and/or place of work). The system 1200 may facilitate the healthcare provider's 1240 ongoing monitoring of the PTSD intervention provided to the individual 1010. In certain aspects, information from the ongoing monitoring can provide data to the individual, healthcare provider, or both which can be used to assess the effectiveness of PTSD treatment over time or at a specific time point.

Figure 13:
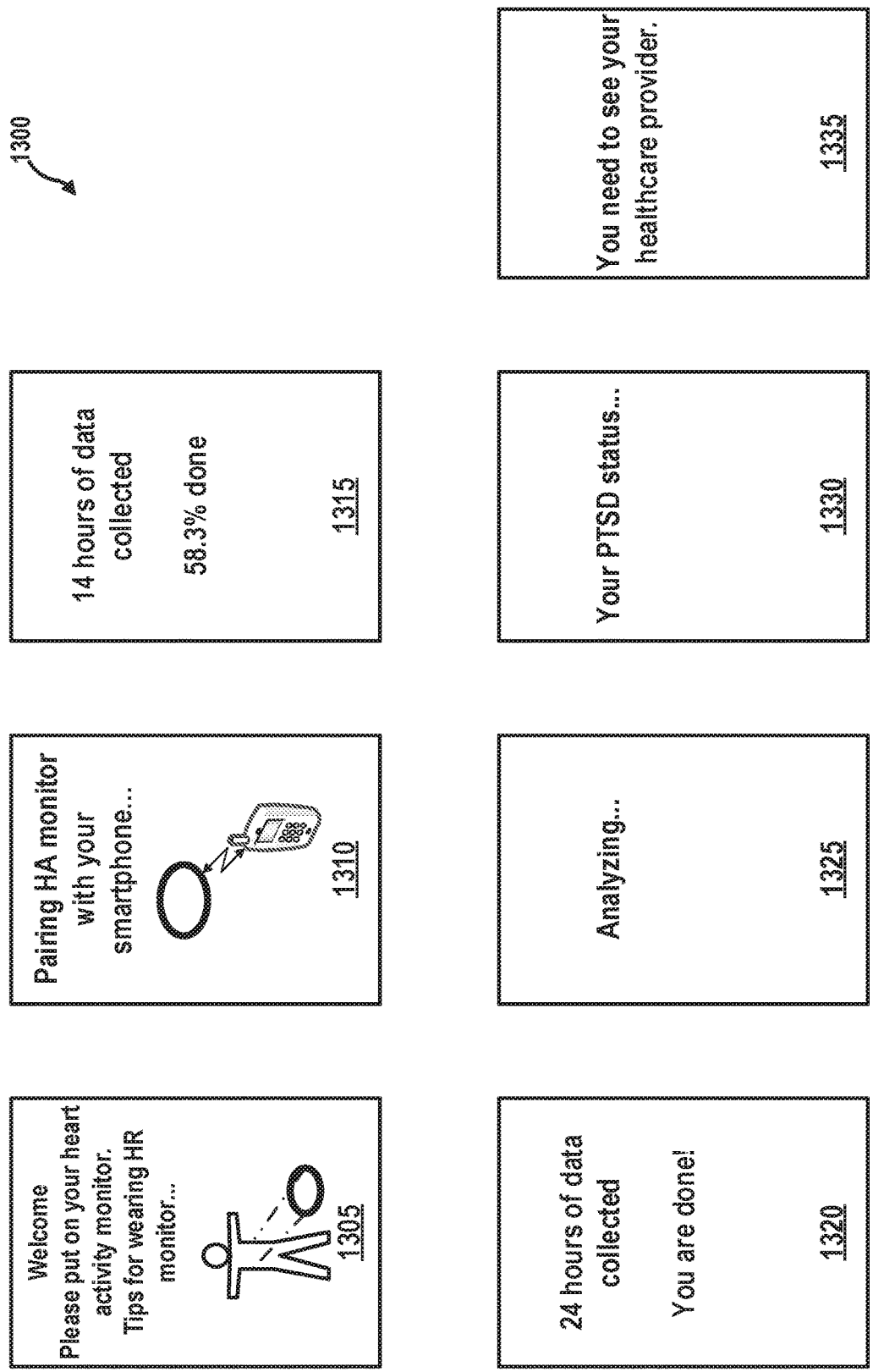
FIG. 13 is an illustration of a user interface of software for receiving information from measured heart activity from an individual according to at least one embodiment.

FIG. 13 is an illustration of a user interface of software (1300) for receiving information from measured heart activity 1535 from an individual 1010 according to at least one embodiment. The software (1300) may be provided on a computing device, such as computing device (1030), computing device (1050), or computing device (1220). Software (1300) may be an implementation of all or a portion of measured heart activity processing unit 1100. At image 1305, software 1300 may advise individual 1010 to put on the heart activity monitor 1500 and may be provided with instructions on how to put on the heart activity monitor 1500. At image 1310, software 1300 may advise individual 1010 of an attempt to make a communication link between the heart activity monitor 1500 and a computing device 1030. Once the communication link is established, at image 1315, the individual 1010 may be advised of an amount of information from measured heart activity 1535 from the individual 1010 that has been received. After an appropriate or predetermined amount of time has elapsed, at image 1320, the software 1300 may advise the individual 1010 that no further receipt of information from measured heart activity 1535 is required. At image 1325, the software 1300 may advise the individual 1010 that the software 1300 is processing the information from measured heart activity 1535, and this processing may comprise determining features from the information from measured heart activity 1535, comparing the features to a model (e.g. a classifier), and/or determining a PTSD status of the individual 1010 based on the comparison of the features to the model. At image 1330, the software 1300 may advise the individual 1010 of information such as an output 1140 (e.g. a PTSD status). At image 1335, the software 1300 may advise the individual 1010 of additional advice or recommendations based on the information provided at image 1330. For example, if a PTSD status is positive or of a certain severity, the software 1300 may advise the individual 1010 to see the healthcare provider 1240.

Figure 16:
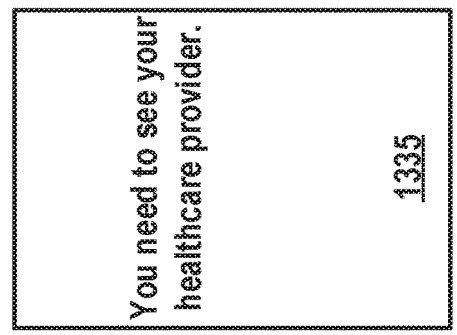
FIG. 16 is an illustration of a user interface of software for receiving information from measured heart activity from an individual according to at least one embodiment.
Figure 16:
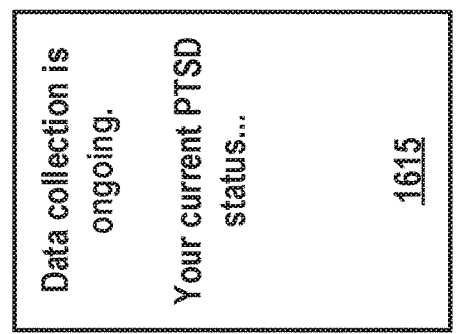
Figure 16:
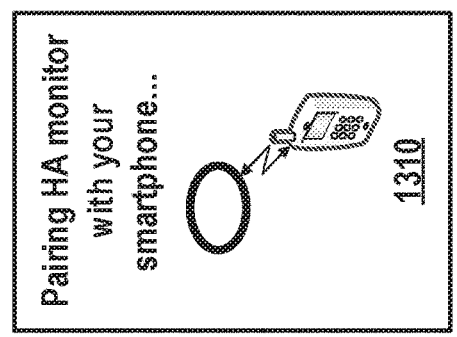
Figure 16:
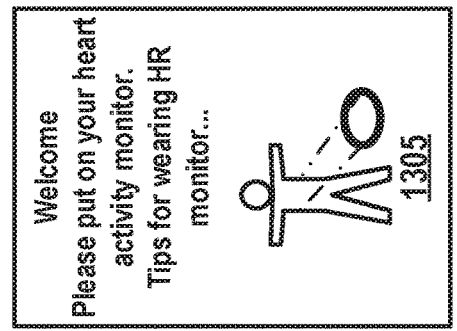

FIG. 16 is an illustration of a user interface of software (1600) for receiving information from measured heart activity from an individual according to at least one embodiment. The software (1600) may be designed for ongoing receipt of information from measured heart activity 1535. The software (1600) may be provided on a computing device, such as computing device (1030), computing device (1050), or computing device (1220). Software (1600) may be an implementation of all or a portion of electrocardiography information processing unit 1100. At image 1305, software 1600 may advise individual 1010 to put on the heart activity monitor 1500 and may be provided with instructions on how to put on the heart activity monitor 1500. At image 1310, software 1600 may advise individual 1010 of an attempt to make a communication link between the heart activity monitor 1500 and a computing device 1030. Once the communication link is established, at image 1615, software 1600 may advise the individual 1010 that information from measured heart activity 1535 from the individual 1010 is being received. Software 1600 may perform processing comprising determining features from the information from measured heart activity 1535, comparing the features to a model (e.g. a classifier), and/or determining a PTSD status of the individual 1010 based on the comparison of the features to the model. Also at image 1615, the software 1600 may advise the individual 1010 of information such as an output 1140 (e.g. a PTSD status). At image 1335, the software 1600 may advise the individual 1010 of additional advice or recommendations based on the information provided at image 1615. For example, if a PTSD status is positive or of a certain severity, the software 1600 may advise the individual 1010 to see the healthcare provider 1240.

Figure 14:
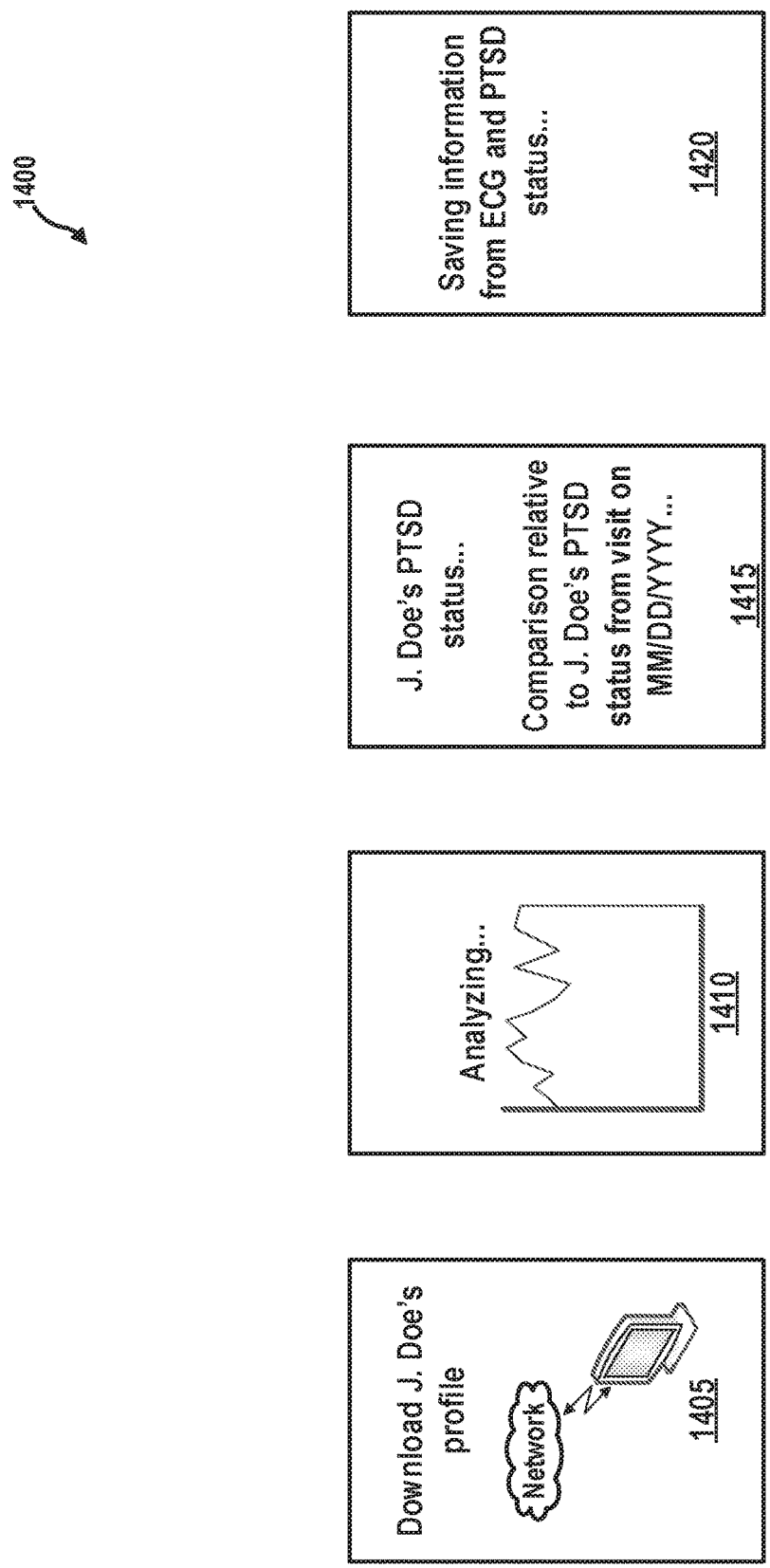
FIG. 14 is an illustration of a user interface of software for professional monitoring of a PTSD status according to at least one embodiment.

FIG. 14 is an illustration of a user interface of software (1400) for professional monitoring of a PTSD status according to at least one embodiment. The software (1400) may be provided on a computing device, such as computing device (1030), computing device (1050), or computing device (1220). The software may be presented to the healthcare provider 1240 by the interface/front end 1230. Software (1400) may be an implementation of all or a portion of electrocardiography information processing unit 1100. At image 1405, software 1400 may provide an interface to access information from measured heart activity 1535 performed on the individual 1010 or an output 1140 (e.g. a PTSD status), and the interface may be a secure interface complaint with healthcare or privacy regulations (e.g. HIPAA). At image 1410, the software 1400 may advise the healthcare provider 1240 that the software 1400 is processing (e.g. processing the information from electrocardiography 1535 or determining an output 1140 (e.g. a PTSD status)), and this processing may comprise determining features from the information from electrocardiography 1535, comparing the features to a model (e.g. a classifier), and/or determining a PTSD status of the individual 1010 based on the comparison of the features to the model. At image 1415, the software 1400 may advise the healthcare provider 1240 of information such as an output 1140 (e.g. a PTSD status). Also at image 1415, the software 1400 may provide information such as a comparison relative to a prior access of information from electrocardiography 1535 performed on the individual 1010 or a prior output 1140 (e.g. a prior PTSD status). Therefore, software 1400 may provide ongoing information of a PTSD status. At image 1420, software 1400 may provide an interface to save information from electrocardiography 1535 performed on the individual 1010 or an output 1140 (e.g. a PTSD status) so that saved information can be retrieved at a later time.

Figure 15:
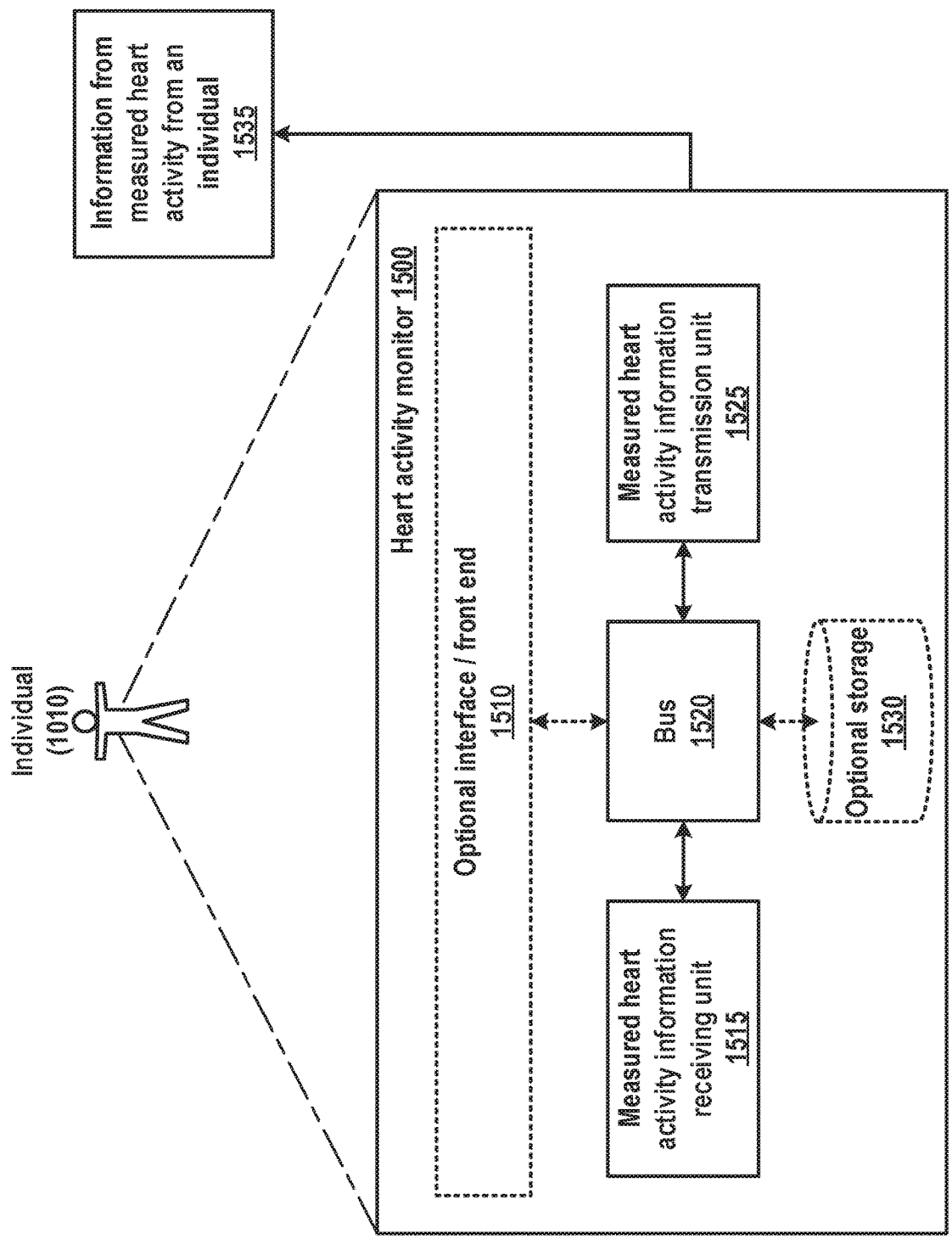
FIG. 15 is a high-level block diagram of heart activity monitor according to at least one embodiment.

FIG. 15 is a high-level block diagram of a heart activity monitor (1500) according to at least one embodiment. The heart activity monitor 1500 includes measured heart activity receiving unit 1515, bus 1520, and measured heart activity transmission unit 1525. Optionally, heart activity monitor 1500 may include optional interface/front end 1510. Optionally, heart activity monitor 1500 may include optional storage 1530.

Individual 1010 wears or is in communication with heart activity monitor 1500 such that measured heart activity receiving unit 1515 receives a heart signal from individual 1010. Measured heart activity receiving unit 1515 may be in electronic communication with bus 1520. Measured heart activity transmission unit 1525 may be in electronic communication with bus 1520. In certain embodiments, the heart activity monitor 1500 can be a heartrate monitor.

Measured heart activity transmission unit 1525 may transmit information from measured heart activity from an individual 1535 using transmission methods disclosed herein, including the transmission methods disclosed herein with respect to heart activity monitor 1500.

Optional interface/front end (1510) may report a PTSD status that is determined using one or more of the methods disclosed herein. Optional interface/front end (1510) may comprise a display (e.g. LCD or LED display), an audio speaker, a vibration generator, a tactile feedback generator, and/or one or more LEDs. Optional interface/front end (1510) may report any of the following: that a heart signal is or is not being received, an amount of time that a heart signal has been received, an amount of time remaining for heart signal reception, that information from measured heart activity from an individual has been saved to optional storage 1530, and/or a status of transmission of information from measured heart activity on an individual. A status of transmission of information from measured heart activity performed on an individual may include any of the following: that the heart activity monitor 1500 is attempting to pair (via e.g. a Bluetooth protocol, a IEEE 802.15.4 protocol, or a IEEE 802.11 protocol) with another device, that the heart activity monitor 1500 is or is not paired with another device, and/or that the electrocardiograph is, or has completed, transmitting information from measured heart activity from an individual 1535.

The amount of information received by the measured heart activity receiving unit 1515 will depend on factors including sampling frequency and duration of sampling of a heart signal. Given the methods disclosed herein, an advantageous amount of optional storage 1530 may be determined. In at least one embodiment, optional storage 1530 is sufficient to store an amount of heart signal appropriate to determine a PTSD status, and in this embodiment, information from measured heart activity from an individual 1535 may not need to be transmitted by the measured heart activity transmission unit 1525 until the entire amount of heart signal appropriate to determine a PTSD status has been received by the measured heart activity receiving unit 1515 and/or stored by the optional storage 1530. Other factors, including mass and cost of optional storage 1530 and mass and cost of any battery included in heart activity monitor 1500, may affect design preferences pertaining to a battery, an optional storage 1530, and a design of the measured heart activity transmission unit 1525.

The implementation of the optional storage 1530 may be done using a volatile or non-volatile storage comprising memory such as flash or 3D XPoint (e.g. Intel Optane or Micron QuantX). Further, the heart activity monitor 1500 may include an analog to digital converter, an electrode, a transducer, a microprocessor, and/or a system on a chip (SoC). The transducer may receive a heart signal from an individual 1010.

Figure 17:
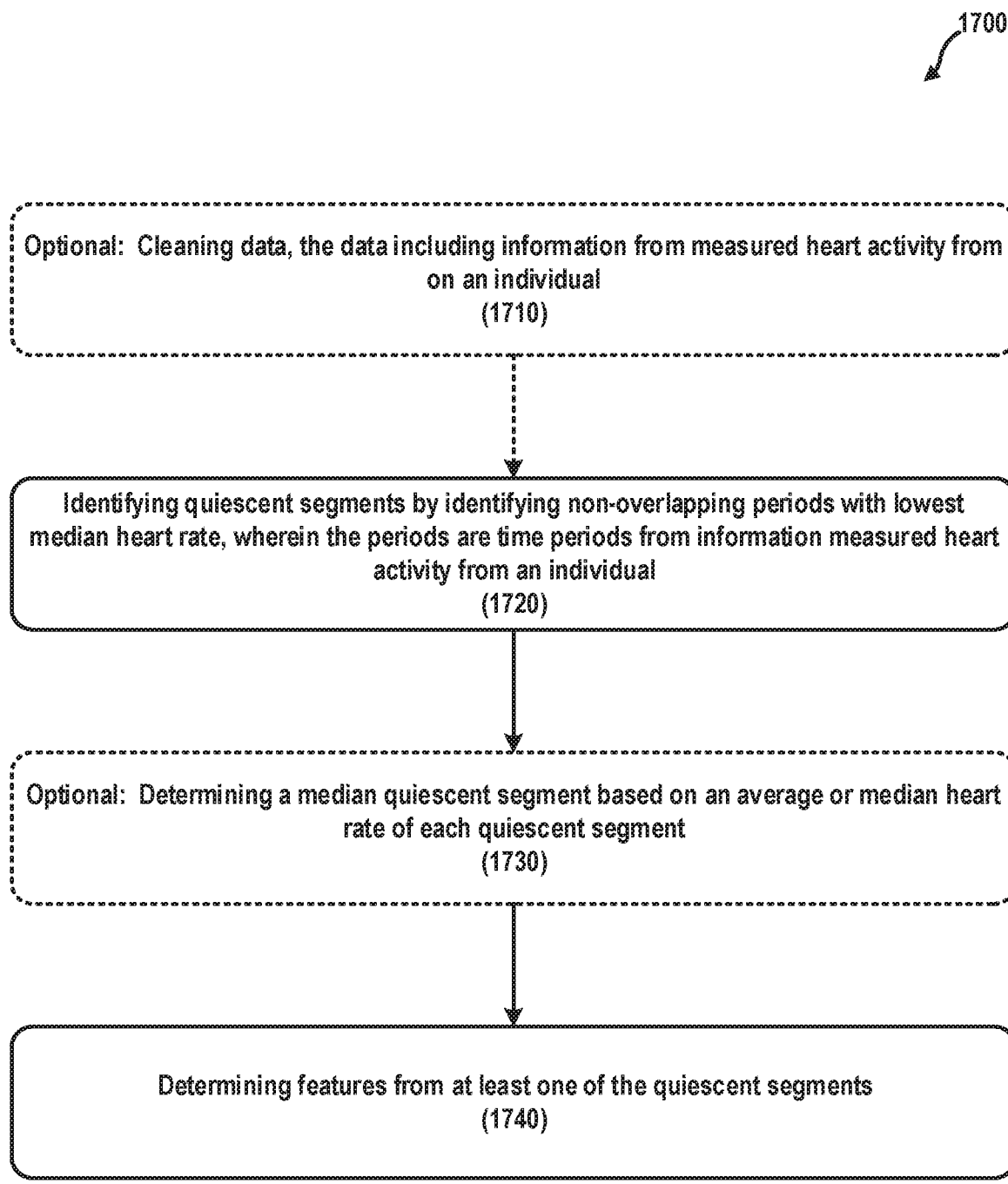
FIG. 17 is a flow diagram illustrating a method for identifying at least one quiescent segment and determining features from the at least one quiescent segment according to at least one embodiment.

FIG. 17 is a flow diagram illustrating a method (1700) for identifying at least one quiescent segment and determining features from the at least one quiescent segment according to at least one embodiment. Optionally, first, data may be cleaned (1710). The data cleaning may be done according to the data cleaning methods disclosed herein and may include one or more exclusion criteria disclosed herein. Second, quiescent segments may be identified (1720) by identifying non-overlapping (or overlapping) periods with lowest median heart rate, wherein the periods are time periods from information from measured heart activity 1535 from an individual 1010. Optionally, third, a median quiescent segment may be determined (1730) based on an average or median heart rate of each quiescent segment. Fourth, features may be determined (1740) from at least one of the quiescent segments. The determining the features from the at least one of the quiescent segments may include determining features from the median quiescent segment. At least a portion of the method (1700) may be used to select quiescent segment(s) as called for at 740 at FIG. 7 and at 840 at FIG. 8.

Figure 18:
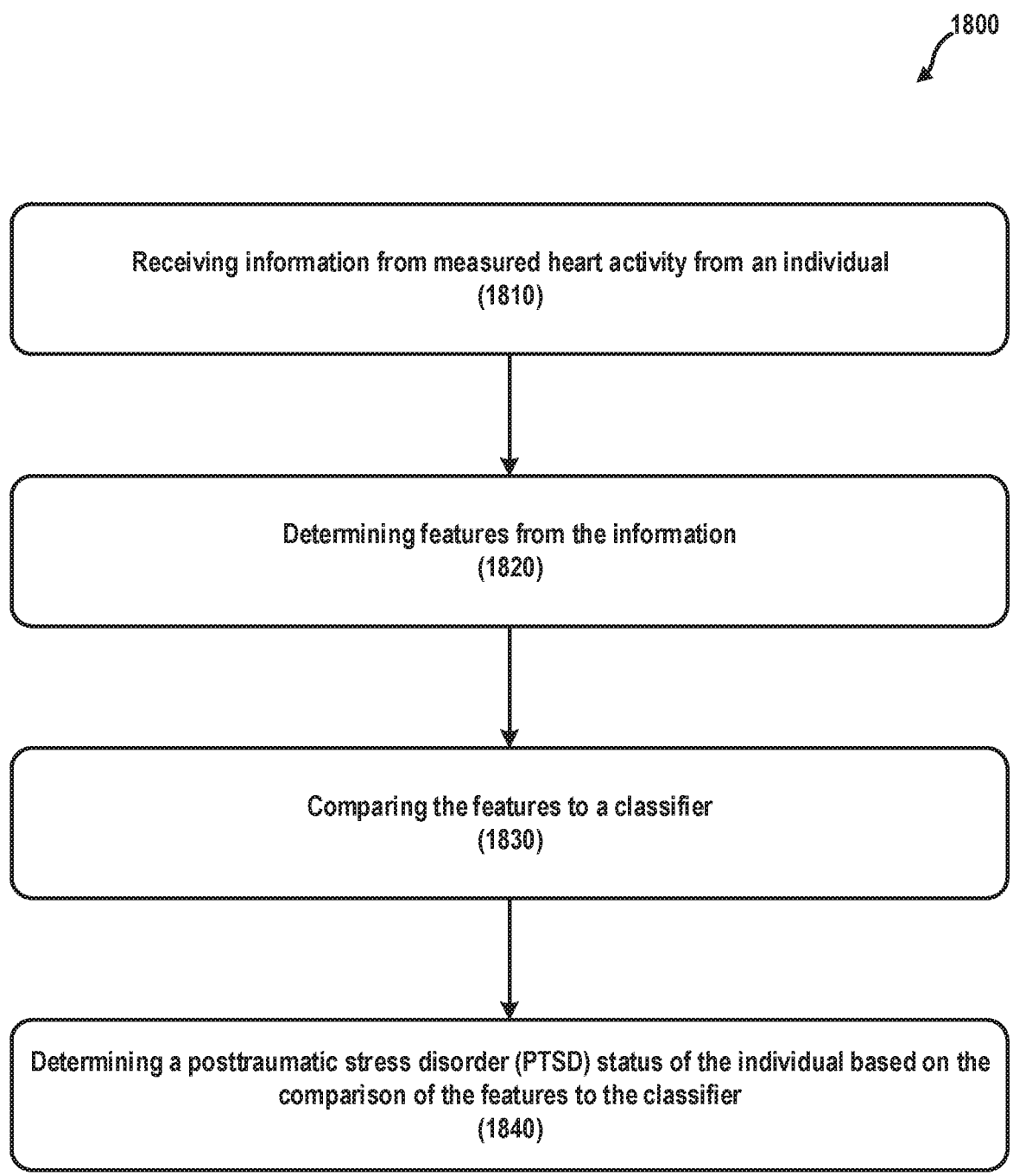
FIG. 18 is a flow diagram illustrating a method for using a classifier to determine a PTSD status according to at least one embodiment.

FIG. 18 is a flow diagram illustrating a method (1800) for using a classifier to determine a PTSD status according to at least one embodiment. First, information from measured heart activity from an individual may be received (1810). Second, features may be determined (1820) from the information. Third, the features may be compared (1830) to a classifier. Fourth, based on the comparison of the features to the classifier, a posttraumatic stress disorder (PTSD) status of the individual may be determined (1840).

Figure 19:
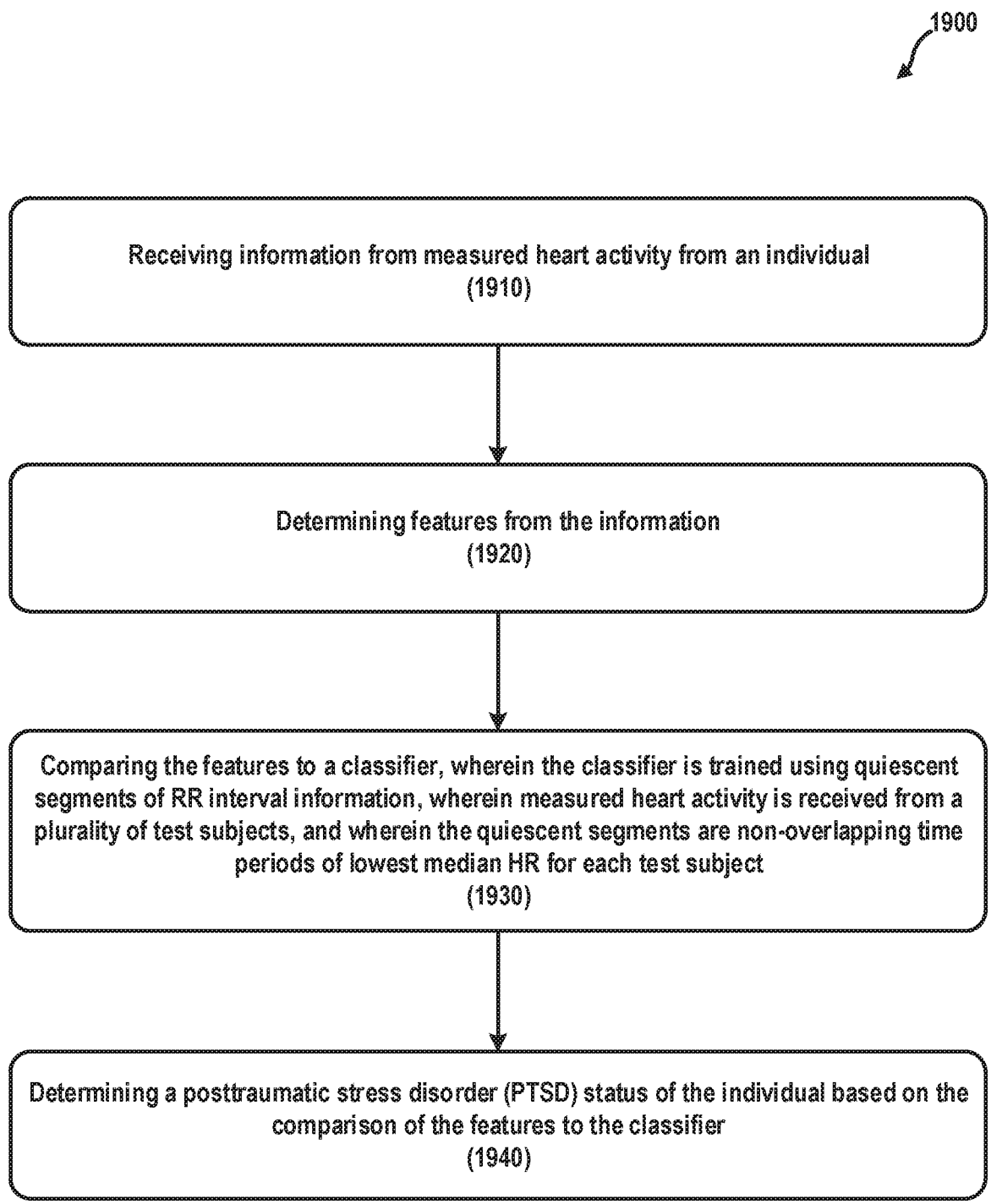
FIG. 19 is a flow diagram illustrating a method for using a classifier to determine a PTSD status according to at least one embodiment.

FIG. 19 is a flow diagram illustrating a method (1900) for using a classifier to determine a PTSD status according to at least one embodiment. First, information measured heart activity from an individual may be received (1910). Second, features may be determined (1920) from the information. Third, the features may be compared (1930) to a classifier, wherein the classifier is trained using quiescent segments of RR interval information, wherein measured heart activity is received from a plurality of test subjects, and wherein the quiescent segments are non-overlapping time periods of lowest median HR for each test subject. Fourth, based on the comparison of the features to the classifier, a posttraumatic stress disorder (PTSD) status of the individual may be determined (1940).

Figure 9:
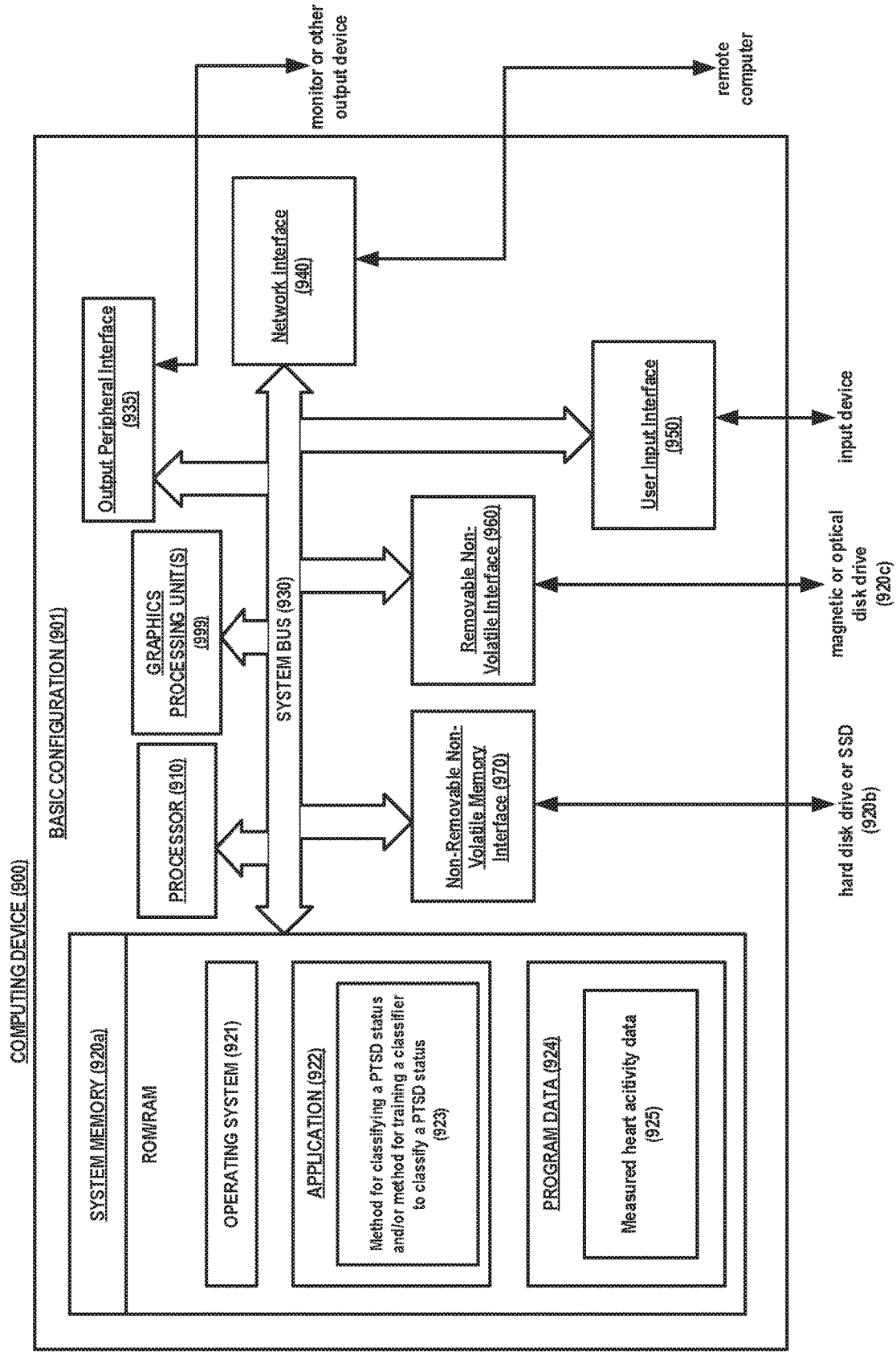
FIG. 9 is a high-level block diagram of an example computer that is arranged for classifying a PTSD status and/or for training a classifier to classify PTSD.

FIG. 9 is a high-level block diagram of an embodiment of an example computer (900) that is arranged for using a classifier to determine a PTSD status and/or for training a PTSD machine learning model. In a very basic configuration (901), the computing device (900) typically includes one or more processors (910) and system memory (920). A system bus (930) can be used for communicating between the processor (910) and the system memory (920).

Depending on the desired configuration, the processor (910) can be of any type including but not limited to a microprocessor (µP), a microcontroller (µC), a digital signal processor (DSP), or any combination thereof. The processor (910) can include one more levels of caching, a processor core, and registers. The processor core can include an arithmetic logic unit (ALU), a floating point unit (FPU), a digital signal processing core (DSP Core), or any combination thereof. A memory controller can also be used with the processor (910), or in some implementations the memory controller can be an internal part of the processor (910).

Depending on the desired configuration, the system memory (920) can be of any type including but not limited to volatile memory (such as RAM), non-volatile memory (such as ROM, flash memory, etc.) or any combination thereof. System memory (920) typically includes an operating system (921), one or more applications (922), and program data (924). The application (922) may include a method for using a classifier to determine a PTSD status and/or a method for training a PTSD machine learning model. Program data (924) includes storing instructions that, when executed by the one or more processing devices, implement a system and method for using a classifier to determine a PTSD status and/or for training a PTSD machine learning model (923). Program data may include (924) may include heart activity data (925). In some embodiments, the application (922) can be arranged to operate with program data (924) on an operating system (921). Program data may include heart activity (e.g. information from a heart activity monitor) (925).

The computing device (900) can have additional features or functionality, and additional interfaces to facilitate communications between the basic configuration (901) and any required devices and interfaces, such non-removable non-volatile memory interface (970), removal non-volatile interface (960), user input interface (950), network interface (940), and output peripheral interface (930). A hard disk drive may be connected to the system bus (930) through a non-removable memory interface (970). A magnetic or optical disk drive may be connected to the system bus (930) by the removable non-volatile interface (960). A user of the computing device (900) may interact with the computing device (900) through input devices such as a keyboard, mouse, or other input peripheral connected through a user input interface (950). A monitor or other output peripheral device may be connected to the computing device (900) through an output interface (930) in order to provide output from the computing device (900) to a user or another device.

System memory (920) is an example of computer storage media. Computer storage media includes, but is not limited to, RAM, ROM, EEPROM, flash memory or other memory technology, CD-ROM, digital versatile disk (DVD), Blu-ray Disc (BD) or other optical storage, magnetic cassettes, magnetic tape, magnetic disk storage or other magnetic storage devices, or any other medium which can be used to store the desired information and which can be accessed by computing device (900). Any such computer storage media can be part of the device (900). One or more graphics processing units (GPUs) (999) may be connected to the system bus (930) to provide computing capability in coordination with the processor (910), especially where single instruction, multiple data (SIMD) problems are present.

The computing device (900) can be implemented as a portion of a small-form factor portable (or mobile) electronic device such as a cell phone, a smartphone, a personal data assistant (PDA), a personal media player device, a tablet computer (tablet), a wireless web-watch device, a personal headset device, an application-specific device, or a hybrid device that includes any of the above functions. The computing device (900) can also be implemented as a personal computer including both laptop computer and non-laptop computer configurations. Additionally, the computing device (900) may operate in a networked environment where it is connected to one or more remote computers over a network using the network interface (950).

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will appreciate that the mechanisms of the subject matter described herein are capable of being distributed as a program product in a variety of forms, and that an illustrative embodiment of the subject matter described herein applies regardless of the particular type of non-transitory signal bearing medium used to actually carry out the distribution. Examples of a non-transitory signal bearing medium include, but are not limited to, the following: a recordable type medium such as a floppy disk, a hard disk drive, a solid state drive (SSD), a Compact Disc (CD), a Digital Video Disk (DVD), a Blu-ray disc (BD), a digital tape, a computer memory, etc.

The computing device (1030), the optional computing device (1050), the electrocardiography information processing unit (1100), the computing device (1220), and/or the interface/front end (1230) may be implemented by all or a portion of the computing device (900). Software (1300), software (1400), and/or software (1600) may executed by the computing device (900).

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1: Methods

Single-channel electrocardiogram (ECG) data were collected from 23 subjects with current PTSD, and 25 discordant twin brother controls with no history of PTSD over 24 hours. RR intervals were derived from these and cleaned using published methods before calculating HR and HRV metrics. A logistic regression model was trained to differentiate between the two groups and its performance assessed via 10-fold cross validation. To reduce noise and activity-related effects, features from five non-overlapping quiescent segments of RR intervals, defined by lowest HR in a 10-minute period, were calculated.

Using 24 hours of data, an exemplary classifier achieved an out-of-sample area under the receiver operating characteristic curve (AUC) of 0.71±0.02 and an accuracy of 0.73±0.01. Using segmentation and selection of data by quiescent state improved the AUC to 0.84±0.01 and the accuracy to 0.80±0.01.

As demonstrated herein, objective quantification of PTSD from ECG data is feasible when using a novel data segmentation approach. This provides the potential for tracking PTSD illness severity via objective physiological monitoring with one or more classifiers as described herein.

Data Analysis.

All data processing, feature extraction, and analysis was performed using MATLAB (MathWorks, Natick, Mass.) R2016b, but the embodiments are not limited thereto.

Data Recording.

ECG recordings were obtained from 24 male subjects with current PTSD (symptoms within the past 30 days) and 26 healthy control subjects following the methodology described in A. J. Shah, R. Lampert, J. Goldberg, E. Veledar, J. D. Bremner, and V. Vaccarino, "Posttraumatic stress disorder and impaired autonomic modulation in male twins," *Biol. Psychiatry*, vol. 73, no. 11, pp. 1103-1110, 2013, which is incorporated entirely herein by reference. Participants were twin pairs discordant for PTSD, but individuals lacking sufficient ECG data were excluded for reasons discussed below, resulting in some twins being unpaired. All participants wore an ambulatory ECG (Holter) monitor (GE Marquette SEER digital system; GE Medical Systems, Waukesha, Wis.) for at least 24 hours. Participants (each twin pair) had matched recording times, schedules, and activity levels. Furthermore, activity was restricted to non-strenuous walking around campus, and participants were told to refrain from smoking and drinking alcohol or coffee.

Data Cleaning and Exclusion Criteria.

RR intervals were derived from ECG data. RR intervals past 24 hours from the start of recording, greater than 1.5 seconds, less than 0.33 seconds, or more than 20% shorter or longer than the previous RR interval or the overall mean RR interval were discarded. Subjects with less than 24 hours of ECG were excluded to ensure that 24 hour metrics were meaningful. One subject with PTSD and one subject without PTSD had fewer than 22 hours of ECG data; both were excluded from further analysis. Cleaned data were obtained from 23 subjects with PTSD and 25 control subjects (48 total). This final cohort consisted of 10 unpaired twins (10 subjects) and 19 discordant twin pairs (38 subjects).

Identifying Quiescent Segments.

To reduce noise and confounding effects of mental and physical activity, quiescent segments were identified. That is, the five non-overlapping 10-minute periods with the lowest median HR were identified for each testing subject; these periods are hereinafter referred to as "quiescent segments". FIG. 1 illustrates a typical 24-hour RR tachogram with quiescent segments indicated by shaded regions. Healthy humans cycle through each of the five defined sleep stages with a period of approximately 100 minutes, and each sleep stage lasts up to 20 minutes; this informed selection of quiescent segment length as used herein. RR interval data from the median quiescent segment was used to calculate HRV features. The median quiescent segment may be determined by taking the median quiescent segment in an ordering of the five quiescent segments by the median heart rate of each quiescent segment. The median quiescent segment may be determined by taking the median quiescent segment in an ordering of the five quiescent segments by the average heart rate of each quiescent segment. A quiescent segment may be from a period during which an individual is asleep. A quiescent segment may be from a period during which an individual is awake.

Feature Extraction and Heart Rate Variability Metrics.

Features were calculated from RR intervals over 24 hours of ECG recordings, or from median quiescent segments. Mode, median, standard deviation, interquartile range, skewness, and kurtosis of RR intervals were calculated. Power spectral measures and acceleration and deceleration capacity were also calculated.

Power Spectral Measures of HRV.

HRV power spectral measures were computed from RR interval time series with a fast Fourier transform with a Parzen window, following the methodology in A. J. Shah, R. Lampert, J. Goldberg, E. Veledar, J. D. Bremner, and V. Vaccarino, "Posttraumatic stress disorder and impaired autonomic modulation in male twins," *Biol. Psychiatry*, vol. 73, no. 11, pp. 1103-1110, 2013, which is incorporated entirely herein by reference. The power spectrum was integrated over four discrete frequency bands: ultra-low frequency (ULF)<0.0033 Hz; very low frequency (VLF) 0.0033-0.04 Hz; low frequency (LF) 0.04-0.15 Hz; and high frequency (HF) 0.15-0.40 Hz. These frequency bands measure the renin-angiotensin, sympathetic, and parasympathetic cardiovascular control systems. Total power, incorporating the full spectrum from (up to 0.40 Hz) was also estimated.

Phase-Rectified Signal Averaging.

Phase-rectified signal averaging (PRSA) was performed to quantify acceleration and deceleration capacity of HR. This method can be used to detect quasi-periodic oscillations in noisy, non-stationary signals and to separate processes occurring during increasing and decreasing parts of the signal. The method may be found in A. Bauer et al., "Phase-rectified signal averaging detects quasi-periodicities in non-stationary data," *Phys. A Stat. Mech. its Appl.*, vol. 364, pp. 423-434, 2006. Because nonperiodic components are eliminated, the PRSA computation is robust against artifacts and ectopic beats. Heartbeat interval shortenings are used as anchors for acceleration-related PRSA signals, whereas heartbeat interval lengthenings are used as anchors for deceleration-related PRSA signals. Sampling frequency was set to 512 Hz, and the window length around anchors was set to 30 elements.

Assessment of PTSD.

The Structured Clinical Interview for Psychiatry Disorders was administered to classify subjects into two categories (also referred to as labels, classes, or classifications): 1) current PTSD with symptoms within the past 30 days, or 2) no history of PTSD (control subjects).

Feature Selection and Classification.

All features, as well as features one a time, were used to train a logistic regression. The output of this binary classifier was the probability of membership in either the PTSD or control group. To reduce coefficient values for co-linear or non-predictive features and create a sparser and more generalizable model, L1 (lasso), L1-L2 (elastic net), and L2 (ridge) regularization were performed. Maximum likelihood estimation was performed using quasi-Newton limited-memory Broyden-Fletcher-Goldfarb-Shanno (L-BFGS) updating. Several implementations of L-BFGS exist, including within the fmincon MATLAB optimization toolbox. Additionally, given the relatively low number of features, a grid search was performed to assess combinations of features. Model performance was assessed using ten-fold cross-validation. To balance the distribution of labels within each fold, data were divided into training and test sets at a 70:30 ratio for each label. Within each fold, training features and labels were used to train the logistic regression, and a grid search was performed to select the optimal value of 2\, that maximized the test set AUC. Classifier performance metrics included AUC, accuracy, sensitivity, specificity, positive predictive value (PPV), and negative predictive value (NPV). These metrics were calculated for training and test sets within each fold.

Example 2: Results: Temporal Distribution of Quiescent Segments

Figure 2:
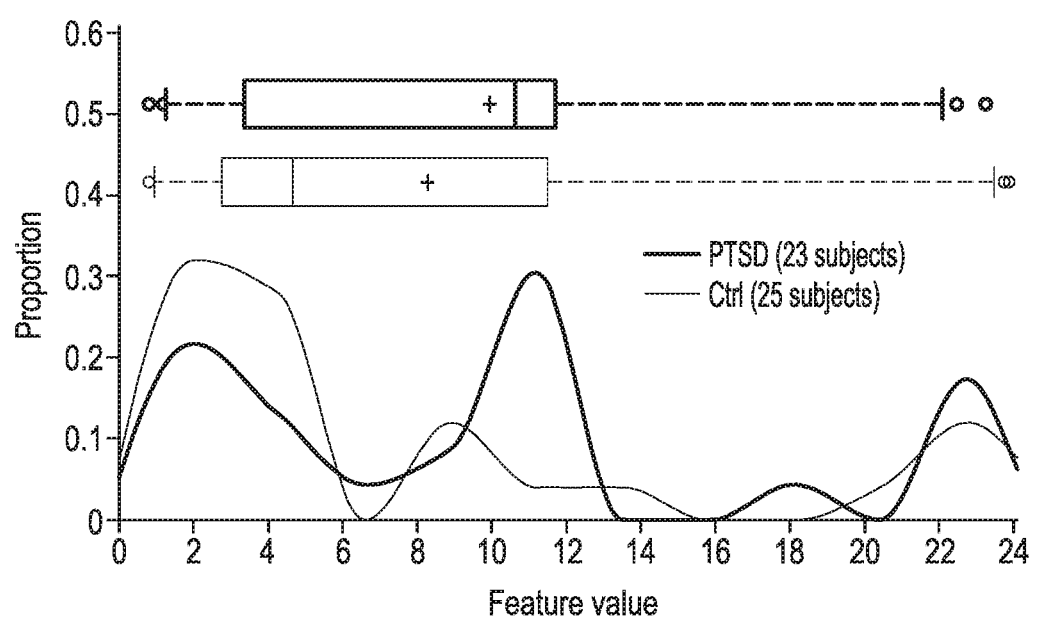
FIG. 2 is a chart showing the temporal distribution of quiescent segments does not differ by PTSD status.

FIG. 2 shows the temporal distribution of quiescent segments does not differ by PTSD status (P=0.32, calculated via two-sided Wilcoxon rank-sum test). The darker of the two lines indicates quiescent segments from subjects with PTSD (23 subjects); the lighter of the two lines indicates the same but for healthy controls (25 subjects). Feature value is hours past midnight, ranging from 0 to 24; 12 corresponds to noon. Box plots are not associated with the y-axis. Within each box plot, + indicates the mean, the middle line indicates the median, the leftmost and rightmost vertical lines in the box indicate the 25th and 75th percentiles respectively, the vertical lines outside of the box indicate the 9th and 91st percentiles, and outliers are denoted by circles.

Example 3: Results: Classifier Trained on all Features

Using all HR and HRV measures from quiescent segments as features for a classifier improves both the training and test set performance of an L1-L2 regularized logistic regression, compared to using features from all 24 hours. Features included the phase of the median quiescent window (time of day normalized to radians), basic RR interval statistics (mean, median, mode, standard deviation, interquartile range, skewness, and kurtosis), AC, DC, power spectral measures (VLF, LF, HF, total power), and other measures of the distribution of RR intervals (NNN, MNN, PNN, PNN50, RMSSD, and SDNN). Training and test set AUC values are shown in Table 1.

TABLE 1

Performance of L1-L2 regularized logistic regression using all HR and HRV features extracted with two different segmentation approaches. Values shown are median ± variance across folds.

| Metric | 24 hrs | Quiescent segments |
|---|---|---|
| Training AUC | 0.75 ± 0.01 | 0.88 ± 0.01 |
| Test AUC | 0.56 ± 0.03 | 0.69 ± 0.01 |

Results for Classifier Trained on Individual Features and Combinations of Features.

Classifier performance using all features was suboptimal, so individual features and combinations of features were explored. The latter approach is generally computationally slow, yet feasible here given the small number of features and subjects and fast speed of training a logistic regression.

Table 2 lists values of some predictive features when using 24 hours of data. The combination of features resulting in the highest training set AUC included AC, DC, total power, and standard deviation of all normal RR intervals (SDNN).

TABLE 2

24 hours of RR interval data: values of most predictive features (median ± variance across subjects) and classifier performance (median ± variance across folds) using individual features. Individual features were selected by median training set AUC.

| | Feature value | | Classifier performance | |
|---|---|---|---|---|
| Feature | PTSD | CTRL | AUC | Accuracy |
| AC (ms)* | −8.28 ± 1.3e1 | −1.04e1 ± 2.1e1 | 0.54 ± 0.01 | 0.67 ± 0.01 |
| DC (ms)* | 8.19 ± 1.2e1 | 1.05e1 ± 2.2e1 | 0.58 ± 0.01 | 0.67 ± 0.01 |
| LF power $(ms^2)$# | 3.51e2 ± 1.3e5 | 5.86e2 ± 2.3e5 | 0.71 ± 0.01 | 0.77 ± 0.01 |
| VLF power $(ms^2)$# | 6.16e2 ± 3.8e5 | 1.02e3 ± 3.2e5 | 0.62 ± 0.01 | 0.73 ± 0.01 |
| Total power $(ms^2)$#,* | 1.22e3 ± 1.5e6 | 2.05e3 ± 1.9e6 | 0.62 ± 0.01 | 0.73 ± 0.01 |
| SDNN (ms)#,* | 3.89e1 ± 2.3e2 | 5.07e1 ± 2.2e2 | 0.61 ± 0.02 | 0.73 ± 0.01 |

CTRL refers to the control group.

$P < 0.05$ comparing feature values from PTSD vs. control subjects via two-sided Wilcoxon rank sum test.

*Feature in combination of features resulting in maximum training set AUC using 24 hours of data.

Table 3 lists values of highly separable features when using quiescent segments. The combination of features resulting in the highest training set AUC included DC, LF power, very low frequency (VLF) power, and SDNN. More detailed performance metrics for the best classifiers for 24 hours and quiescent segments are shown in Table 4. Using quiescent segments rather than 24 hours of data improved out-of-sample AUC from 0.71±0.01 to 0.84±0.01.

TABLE 3

Quiescent segments of RR interval data: values of most predictive features (median ± variance across subjects) and classifier performance (median ± variance across folds) using individual features. Individual features were selected by median training set AUC.

| Feature | Feature value | | Classifier performance | |
| --- | --- | --- | --- | --- |
| | PTSD | CTRL | AUC | Accuracy |
| AC (ms)[#] | −9.62 ± 1.5e1 | −1.28e1 ± 4.4e1 | 0.77 ± 0.01 | 0.77 ± 0.01 |
| DC (ms)[#,*] | 9.43 ± 1.6e1 | 1.40e1 ± 5.6e1 | 0.82 ± 0.01 | 0.80 ± 0.01 |
| LF power (ms$^2$)[#,*] | 3.31e2 ± 6.9e4 | 7.56e2 ± 4.5e5 | 0.82 ± 0.01 | 0.80 ± 0.01 |
| VLF power (ms$^2$)[#,*] | 7.52e2 ± 7.4e5 | 1.65e3 ± 1.2e6 | 0.66 ± 0.03 | 0.70 ± 0.02 |
| Total power (ms$^2$)[#] | 1.82e3 ± 1.8e6 | 2.89e3 ± 4.6e6 | 0.72 ± 0.03 | 0.77 ± 0.01 |
| SDNN (ms)[#,*] | 4.68e1 ± 2.9e2 | 6.47e1 ± 3.8e2 | 0.75 ± 0.02 | 0.77 ± 0.01 |

CTRL refers to the control group.
[#]P < 0.05 comparing feature values from PTSD vs. control subjects via two-sided Wilcoxon rank sum test.
*Feature in combination of features resulting in maximum training set AUC using quiescent segments.

TABLE 4

Out-of-sample (test set) performance of best classifiers trained on features extracted with two different segmentation approaches. Values are median ± variance.

| Metric | 24 hrs | Quiescent segments |
| --- | --- | --- |
| AUC[#] | 0.71 ± 0.02 | 0.84 ± 0.01 |
| Accuracy | 0.73 ± 0.02 | 0.80 ± 0.01 |
| Sensitivity | 0.81 ± 0.02 | 0.72 ± 0.03 |
| Specificity | 0.79 ± 0.01 | 0.94 ± 0.04 |
| PPV | 0.77 ± 0.02 | 0.92 ± 0.03 |
| NPV | 0.81 ± 0.02 | 0.78 ± 0.01 |

PPV is positive predictive value and
NPV is negative predictive value.
[#]P < 0.05 via Wilcoxon rank sum test.

Results for Distribution of Predictive Features.

Distributions of some predictive features were visualized. FIGS. 3-5 show histograms of estimated kernel density of each feature, as well as box plots of distributions (not associated with the y-axis). Within each box plot, + indicates the mean, the middle line indicates the median, the leftmost and rightmost vertical lines in the box indicate the 25th and 75th percentiles respectively, the vertical lines outside of the box indicate the 9th and 91st percentiles, and outliers are denoted by circles. P-values were calculated via two-sided Wilcoxon rank-sum test comparing median feature values from subjects with PTSD versus healthy controls.

Figure 3A:
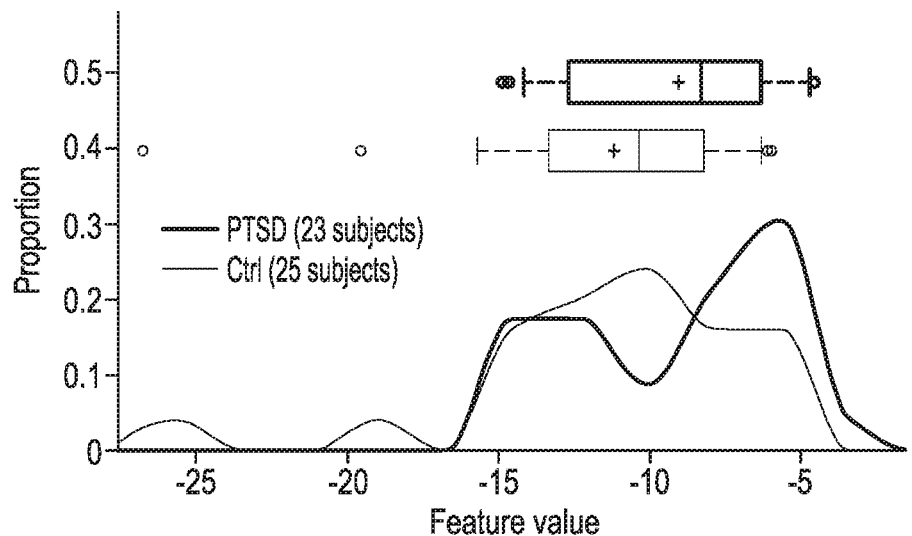
FIG. 3A is a chart showing acceleration capacity (AC) does not differ significantly by PTSD status for 24 hours of data.
Figure 3B:
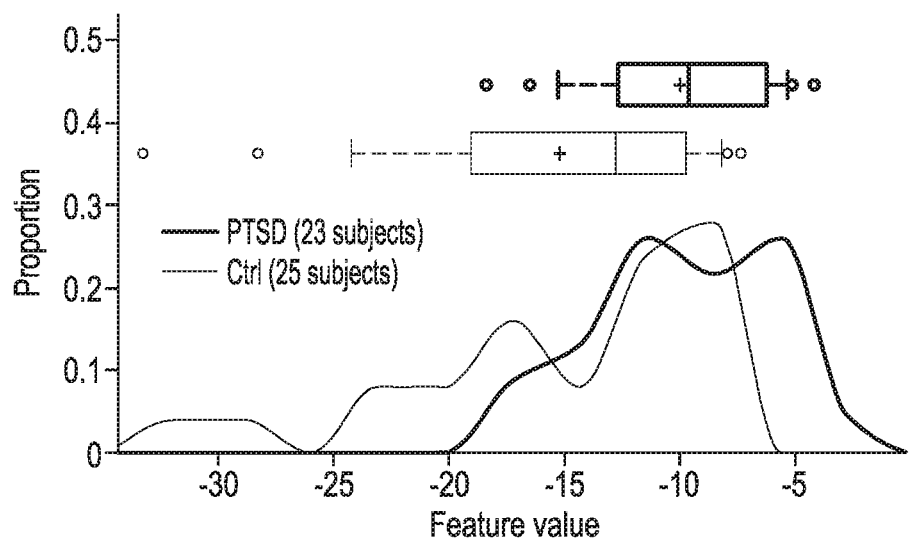
FIG. 3B is a chart showing AC is significantly higher in subjects with PTSD versus controls when analyzing quiescent segments.
Figure 4A:
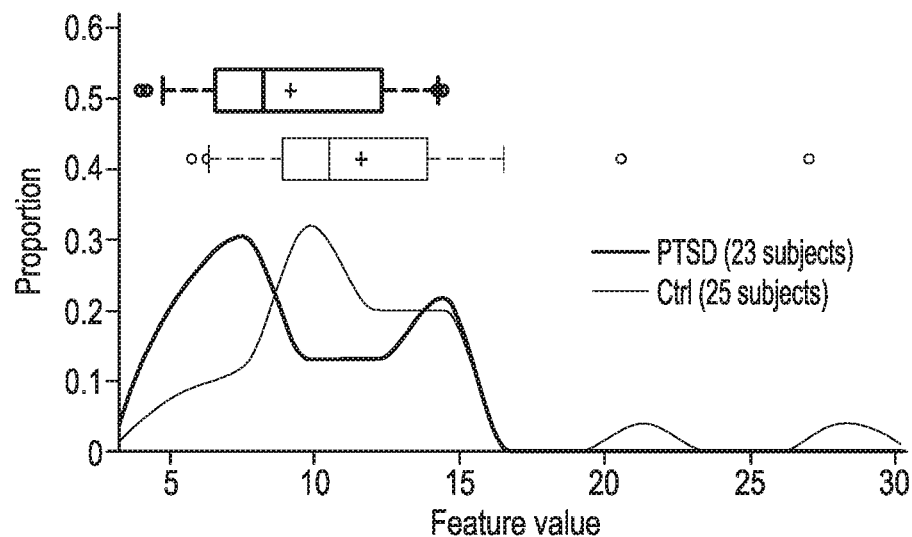
FIG. 4A is a chart showing that deceleration capacity (DC) does not differ significantly by PTSD status for 24 hours of data.
Figure 4B:
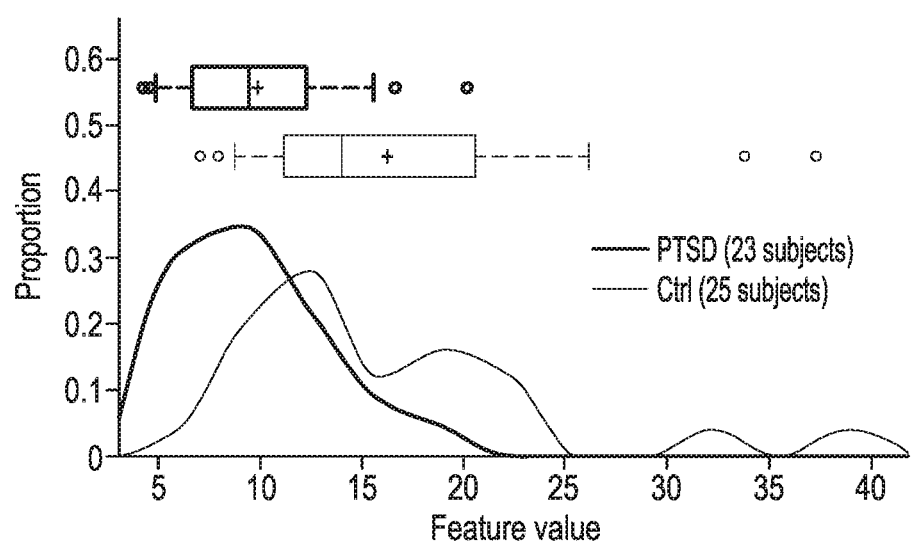
FIG. 4B is a chart showing that deceleration capacity (DC) is lower in subjects with PTSD versus controls when analyzing quiescent segments.
Figure 5A:
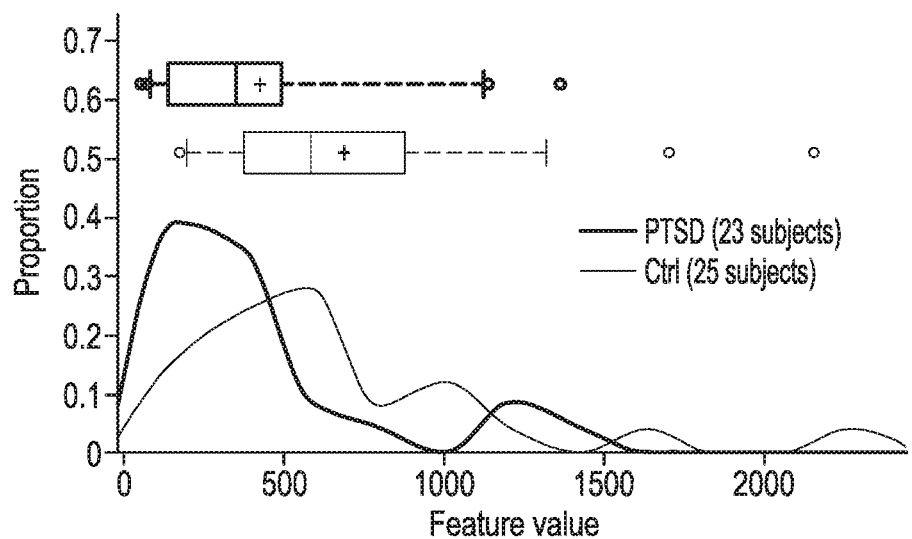
Figure 5B:
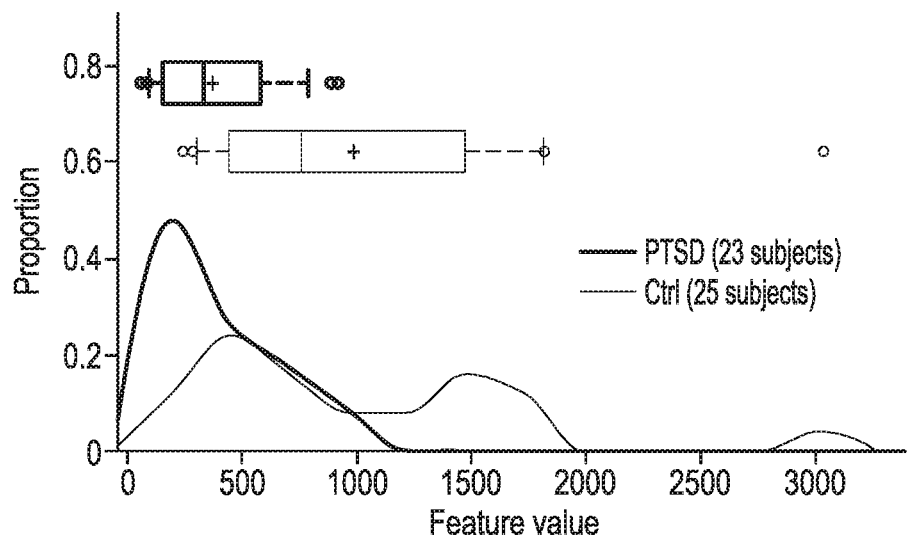
FIG. 5B is a chart showing that LF power is lower in subjects with PTSD versus healthy controls when analyzing quiescent segments.
Figure 6A:
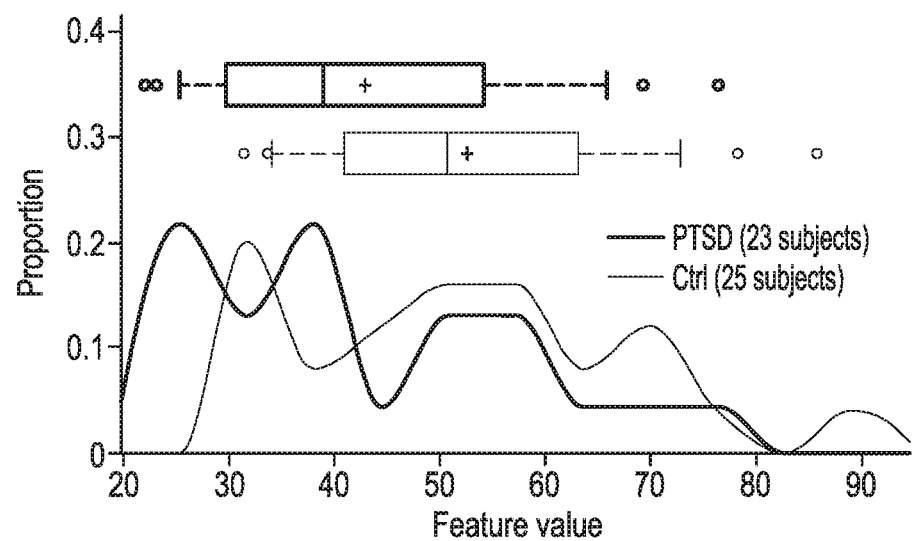
FIG. 6A is a chart showing that the standard deviation of normal-to-normal RR intervals (SDNN) is lower in subjects with PTSD versus healthy controls for 24 hours of data.
Figure 6B:
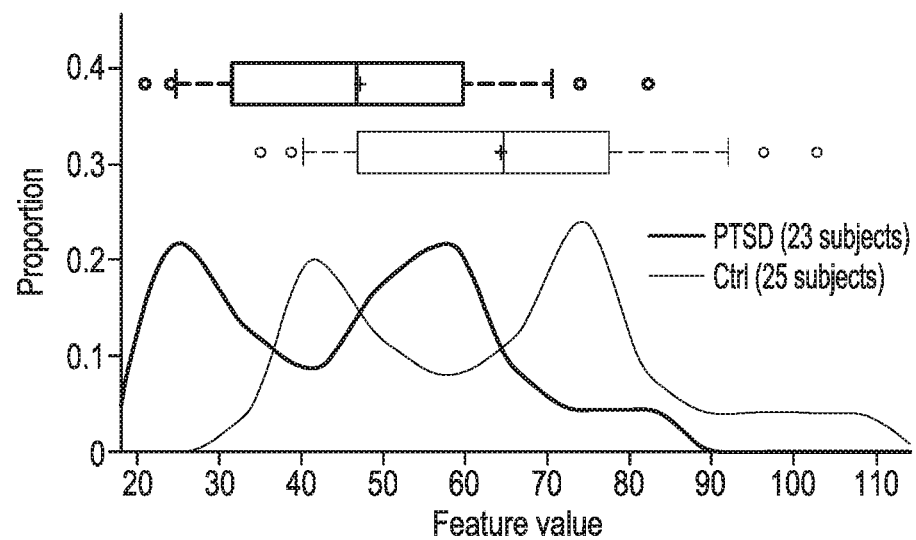
FIG. 6B is a chart showing that SDNN is lower in subjects with PTSD versus healthy controls when analyzing quiescent segments.

Segmentation improves separation of some features. AC does not significantly differ by PTSD status when evaluating 24 hours of data (P=0.18; FIG. 3a), but is significantly higher in subjects with PTSD versus controls when analyzing quiescent segments (P<0.05; FIG. 3b). (P-values calculated via two-sided Wilcoxon rank sum test.) Similarly, DC does not significantly differ by PTSD status when evaluating 24 hours of data (P=0.09; FIG. 4a), but is significantly lower in subjects with PTSD versus controls when analyzing quiescent segments (P<0.05; FIG. 4b). (P-values calculated via two-sided Wilcoxon rank sum test.) On the other hand, LF power was lower for subjects with PTSD versus healthy controls, for both 24-hour data (P<0.05; FIG. 5a) and quiescent segments of data (P<0.05; FIG. 5b). (P-values calculated via two-sided Wilcoxon rank sum test.) Similarly, the standard deviation of normal-to-normal RR intervals (SDNN) was significantly lower for subjects with PTSD versus healthy controls, for both 24-hour data (P<0.05; FIG. 6a) and quiescent segments of data (P<0.05; FIG. 6b). (P-values calculated via two-sided Wilcoxon rank sum test.)

In this study on 23 subjects with current PTSD and 25 controls with no history of PTSD, HR and HRV features were extracted and used to train a regularized logistic regression to classify PTSD status. A classifier trained on a combination of four most predictive features—AC, DC, total power, and SDNN for 24 hours of data, and DC, LF power, VLF power, and SDNN for quiescent segments—achieved an out-of-sample AUC of 0.71±0.02 using 24 hours of RR interval data, whereas a classifier trained on most predictive features from quiescent segments of data achieved an out-of-sample AUC of 0.84±0.01.

Sleep disordered breathing and sleep disruption are both associated with PTSD; therefore, proxies of sleep are expected to differ between subjects with PTSD and controls. However, the temporal distribution of median quiescent segments did not differ with PTSD status (P=0.32; FIG. 2), indicating that these factors were not significant in this cohort. Most quiescent segments occurred from midnight to early morning in control subjects. A larger portion of segments were distributed closer to noon in subjects with PTSD. Periods of low HR—a measure of restfulness, not sleep stage—can occur at any time and may reflect differences in sleep patterns, differences in activity, or both. Quiescent segments may contain less noise and movement artifact, as well as reflect lower levels of mental and physical activity, and thus improve the performance of a classifier trained on features from those periods.

HR and HRV measures were used as features for a logistic regression classifier. L1-L2 regularization was performed to reduce coefficient values associated with co-linear or redundant features and isolate predictive features. A classifier trained with 24 hours of RR intervals achieved a test AUC of 0.55. Using features extracted from quiescent segments improved the test AUC to 0.69 (Table 1). Compared to these low test set AUCs, training set AUCs were 0.75 and 0.88 for 24 hours and quiescent segments respectively.

In this population, classifier performance using all features was too low to have clinical utility, so we tested individual features and combinations of features to train lower-dimensional models. Given m=20 total features and a subset of k=1, 2, . . . , 4 features, the number of possible combinations (i.e. possible arrangements of k features) is the binomial coefficient $$\binom{m}{k}.$$

To ensure feasible computation time and a parsimonious and interpretable model, the maximum number of features used in a combination may be limited, for example, to four, i.e. k=1, 2, . . . , 4, but the embodiments are not limited thereto.

$$\left(\text{Note } \binom{20}{4} = 4845.\right)$$

It may be desirable to have at least ten times as many individuals as features in each class in the training data, but the embodiments are not limited thereto. In this population, using more than four features led to the selection of co-linear features and overfitting on the training data, but the embodiments are not limited thereto as different data sets may motivate different choices of features.

Values of some individually predictive features, and test set AUC and accuracy for classifiers trained on these features, are shown in Table 3. We selected features based on predictability, not significance; the latter property does not guarantee predictability.

When using 24 hours of RR interval data, training set AUC was maximized using a combination of four features: AC, DC, total power, and standard deviation of all normal RR intervals (SDNN).

When using quiescent segments of RR interval data, training set AUC was maximized using a different combination of four features: DC, LF power, very low frequency (VLF) power, and SDNN.

The distribution of AC stratified by PTSD status is shown in FIG. 3a for 24 hours of data, and FIG. 3b for quiescent segments. Similarly, the distribution of DC by PTSD status is shown in FIG. 4. AC may reflect physiologic performance when parasympathetic withdrawal occurs, whereas DC measures general parasympathetic augmentation. Although some literature suggests that AC also measures sympathetic activation, this is unlikely because sympathetic modulations occur at 0.1 Hz, which may be four times faster than the modulation frequency of AC, depending on the underlying heart rate.

The distribution of LF power stratified by PTSD status is shown in FIG. 5a for 24 hours of data, and FIG. 5b for quiescent segments of data. Differences in these measures by PTSD status may be exacerbated in quiescent segments, which may reflect increased insomnia or sleep-disordered breathing in PTSD. Hence, during slow-wave sleep, when vagal augmentation is expected, a reduction in this activity may occur in PTSD. Other physiologic pathways may also be affected during abnormal sleep episodes, as low LF may reflect baroreceptor insensitivity, and low VLF may reflect impairment in the renin-angiotensin pathway. Overall, these findings underscore physiologic changes that occur with PTSD.

When shifting from 24 hours to quiescent segments, total power and AC become less predictive, whereas VLF— which may approximate total power for short time periods— and LF become more predictive. Total power and SDNN quantify variability of the data, are non-specific, and may reflect large changes in HRV due to behavioral differences, movement, and other stressors. Quiescent segments approximate restfulness rather than sleep state, but may also correspond to slow-wave sleep, during which vagal activity may be augmented and the predictive utility of AC reduced.

A classifier trained with four most predictive features from quiescent segments outperformed a classifier trained with four most predictive features from all 24 hours of data (Table 4). The median AUC on out-of-sample test data improved from 0.71 to 0.84. Every performance metric improved except sensitivity and NPV, which decreased; however, AUC was the only classifier metric that significantly differed when changing from 24 hours to quiescent segments.

In at least one embodiment, the approach we described may enable home-based continuous physiologic monitoring of the efficacy of a PTSD intervention. Such monitoring may last longer than 24 hours. Additional validation studies and a specific, rather than sensitive, assay may be developed to prevent alarm fatigue driven by false positives, and studies may include monitoring during an intervention.

In at least one embodiment, the model uses physiological effects of PTSD on the ANS as input and provides probability of being diagnosed with PTSD as output. This output may be a proxy for severity of PTSD. For example, a subject with a known diagnosis of PTSD, but low indicators of ANS dysfunction typically associated with current PTSD, might have a lower severity of illness. Generally, probability of a diagnosis of PTSD may not be equivalent to clinical measures of illness symptomatology, but the embodiments are not thereby limited. Estimating manifestations of PTSD severity may be more clinically useful than estimating a binary state of diagnosis.

The classification of PTSD within a sample of veteran twin brothers discordant for PTSD is described herein using features extracted from 24 hours of HR and HRV features and an L1-L2 regularized logistic regression model. In the tested population, features extracted from quiescent segments, or periods with lowest HR, are shown to be more predictive than features calculated from 24 hours of data; classifier AUC significantly improves from 0.71±0.02 to 0.84±0.01, and accuracy improves from 0.73±0.01 to 0.80±0.01. Classification performance is also improved using a novel method of segmenting data into quiescent segments to filter out activity- or noise-related effects.

Results stated herein were based on a population of a certain size with each individual providing data pertinent to that individual. Results may vary. Lesser favorable results may not be less favorable given a different population. Therefore, lesser favorable results stated herein could be interpreted as not foreclosing or not dissuading the use of the combinations or methods leading to said lesser favorable results. Feature selection may depend on the population used to train a classifier.

The logistic regression classifier may be in a feature space of k dimensions, where k is the number of features in the feature vectors on which the logistic regression classifier was trained. A feature vector from a time slice of an individual's RR pattern may be mapped to the feature space, and the logistic regression classifier may output a probability of PTSD for an individual. This probability may be a proxy for severity of PTSD of the individual.

Example 4

A further example of a monitoring system and method for determining a posttraumatic stress disorder (PTSD) indicator.

For the purpose of explanation, the term "test subject" is used to refer to one or more individuals in a sample population, with "test data" being used to refer to data collected from the test subject. The term "subject" refers to any individual that is being assessed for the purpose of determining a PTSD indicator, with "subject data" being used to refer to data collected from the subject. The test subject and subject are animals, and more particularly humans, although this is not intended to be limiting and the techniques could be applied more broadly to other vertebrates and mammals.

For the purpose of this example, it is assumed that the monitoring system includes one or more electronic processing devices typically forming part of one or more processing systems, such as servers, personal computers or the like and which may optionally be connected to one or more processing systems, data sources or the like via a network architecture as will be described in more detail below.

In use the processing devices obtain subject data indicative of a measured heart activity for the biological subject over a period of time. The subject data could be obtained in any appropriate manner, including receiving data from a monitoring device, computer system or the like, retrieving the subject data from a data store such as a database, collecting at least some of the subject data using one or more sensors, or the like. The subject data typically includes heart activity data indicative of the heart activity, which may be in the form of simple heart rate, such as pulse information, but may also include waveform information, for example obtained via electrocardiography (ECG) or the like. The heart activity is typically measured for at least part of a sleep episode, but more typically over at least one entire sleep episode, which is a period of time during which the subject is asleep, between sleep onset and waking events. The subject data may also be indicative of a heart activity measured over multiple sleep episodes and/or non-sleep periods, with the data optionally being collected continuously during the sleep episode or at periodic intervals through the sleep episode. The subject data may also include additional data, such as data regarding subject attributes or other physiological signals measured from the subject, such as measures of physical or mental activity, or the like.

The processing device(s) then analyze the subject data to determine one or more quiescent segments of the period of time using the heart activity. This can be achieved in any appropriate manner, but typically involves determining variations in the recorded heart activity, and then identifying quiescent segments by comparison to the heart activity variations, for example to identify time periods of lowest median HR or lowest average heartrate.

Following this, the processing device(s) analyze the subject data to determine at least one feature relating to the heart activity during a quiescent segment. The feature can be of any appropriate form, and will be determined based on analysis of the heart rate or other parameters, such as heart activity waveforms, power spectra, or the like.

The processing device(s) then apply the at least one feature to at least one computational model to determine a posttraumatic stress disorder (PTSD) indicator indicative of a PSTD status of the biological subject. In this regard, the computational model embodies a relationship between PSTD and one or more features, and is obtained by applying machine learning to test features derived from measured heart activity for one or more test subjects during at least part of test quiescent segments of a test period of time.

Thus, it will be appreciated that in practice test subject data, equivalent to subject data, is collected for a plurality of test subjects for which a variety of different PTSD states have been diagnosed. The collected test subject data is used to calculate test features, which are then used to train the computational model(s) so that the computational model(s) can discriminate between different PTSD states, based on features derived from the subject's heart activity. The nature of the model and the training performed can be of any appropriate form and could include any one or more of decision tree learning, random forest, logistic regression, association rule learning, artificial neural networks, deep learning, inductive logic programming, support vector machines, clustering, Bayesian networks, reinforcement learning, representation learning, similarity and metric learning, genetic algorithms, rule-based machine learning, learning classifier systems, or the like. As such schemes are known, these will not be described in any further detail.

In one example, the PTSD indicator could include a numerical value, for example indicating that there is a 95% likelihood of the subject having PTSD, or could be a general indication, such as a low, medium or high likelihood. The indicator may also include separate indicators indicative of a likelihood of and severity of PTSD, although this is not essential.

Accordingly, it will be appreciated that the above described method utilises a machine leaning technique in order to assess a PTSD status for a subject, utilising certain defined features relating to specific aspects of heart activity.

A number of further features will now be described.

In one example, the PTSD status is indicative of a severity of PTSD and/or a probability of PTSD, although any suitable indication could be used.

The processing device(s) typically determine the quiescent segment based on a period during which the subject was awake and/or a period during which the subject was asleep. This could be determined based on heart activity, but also based on other data, such as general movement data or the like. The quiescent segment can be based on a median quiescent segment and/or from one or more non-overlapping 10-minute periods of lowest median HR or lowest average heartrate.

Typically the features are selected from heart rate statistic features, heart rate spectral power features or heart rate variability features, with multiple features optionally being selected from across these groups.

Heart rate statistic features are based on the subject's heart rate and can include any one or more of a mean, a median, an average, a variance, a skew, a kurtosis, a percentile, a cumulative distribution function, or the like. Heart rate spectral power features are based on a spectral power of the subject's heart beats, and are typically assessed in frequency bands including, an ultra-low frequency band, such as less than about 0.003 Hz, a very low frequency band, such as between about 0.003 Hz and about 0.04 Hz, a low frequency band, such as between about 0.04 Hz and about 0.15 Hz or a high-frequency band, such as between about 0.15 Hz and about 0.4 Hz. The heart rate variability feature is based on the subject's heart rate and typically includes one or more of a multi-scale entropy, a standard deviation of average pulse intervals, a square root of the mean of the squares of differences between adjacent pulse intervals, or the like.

The features can also include one or both of an acceleration capacity (AC) or deceleration capacity (DC), which can be quantified using phase-rectified signal averaging (PRSA).

The analysis is also typically performed to take into account subject attributes, such as subject characteristics, possible mental states suffered by the subject, possible medications taken, or one or more subject body states. In this example, the one or more processing devices can use the one or more subject attributes to apply the computational model so that the at least one feature is assessed based on test features derived for one or more test subjects having similar attributes to the subject attributes. This can be achieved in a variety of ways, depending on the preferred implementation, and can include selecting features and/or one of a number of different computational models at least in part depending on the subject attributes. Irrespective of how this is achieved, it will be appreciated that taking into account subject attributes can further improve the discriminatory performance by taking into account that subjects with different attributes may react differently to PTSD. For example, a male 35 year old with PTSD may react differently to a female 60 year old with PTSD.

In one example, the monitoring system includes a monitoring device having at least one sensor and a monitoring device processor that generates sensor data in accordance with signals from the sensor, with the sensor data being indicative of at least heart activity of the subject.

In one example, the monitoring device is in the form of a wearable monitoring device which could include a wrist or chest mounted heart rate monitor, including a suitable heart activity detection mechanism. Examples include the use of an optical based system for detection of wrist pulse, or a movement sensor for detection of a chest pulse. The monitoring system could also incorporate electrocardiography sensing.

It will be appreciated that the techniques of using machine learning classification can be performed using the techniques previously outlined in the document, and that respective features of the embodiments can be used interchangeably as desired.

Example 5

Figure 20:
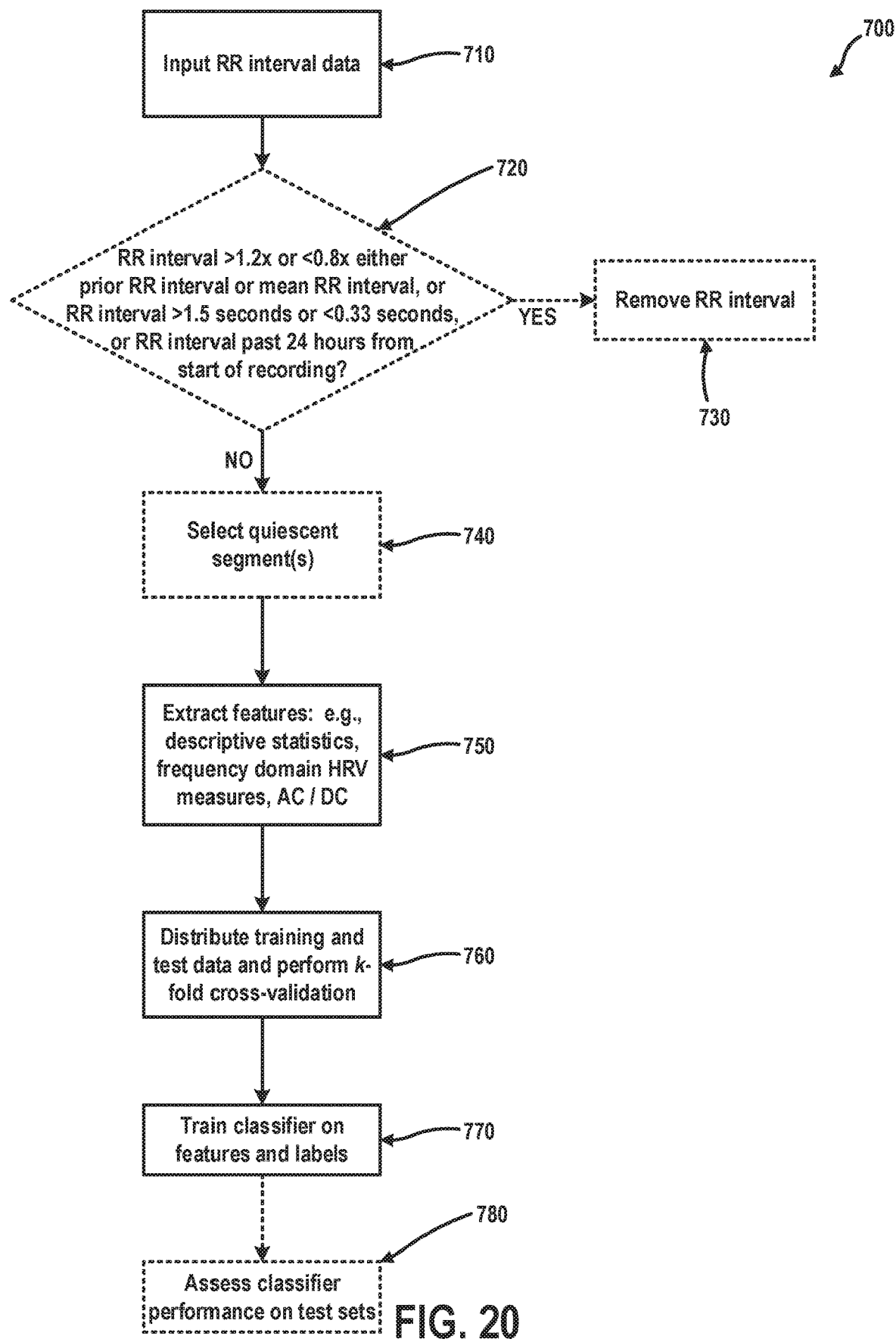
FIG. 20 is a flow diagram of an example method for training a classifier that classifies a PTSD status.
Figure 21:
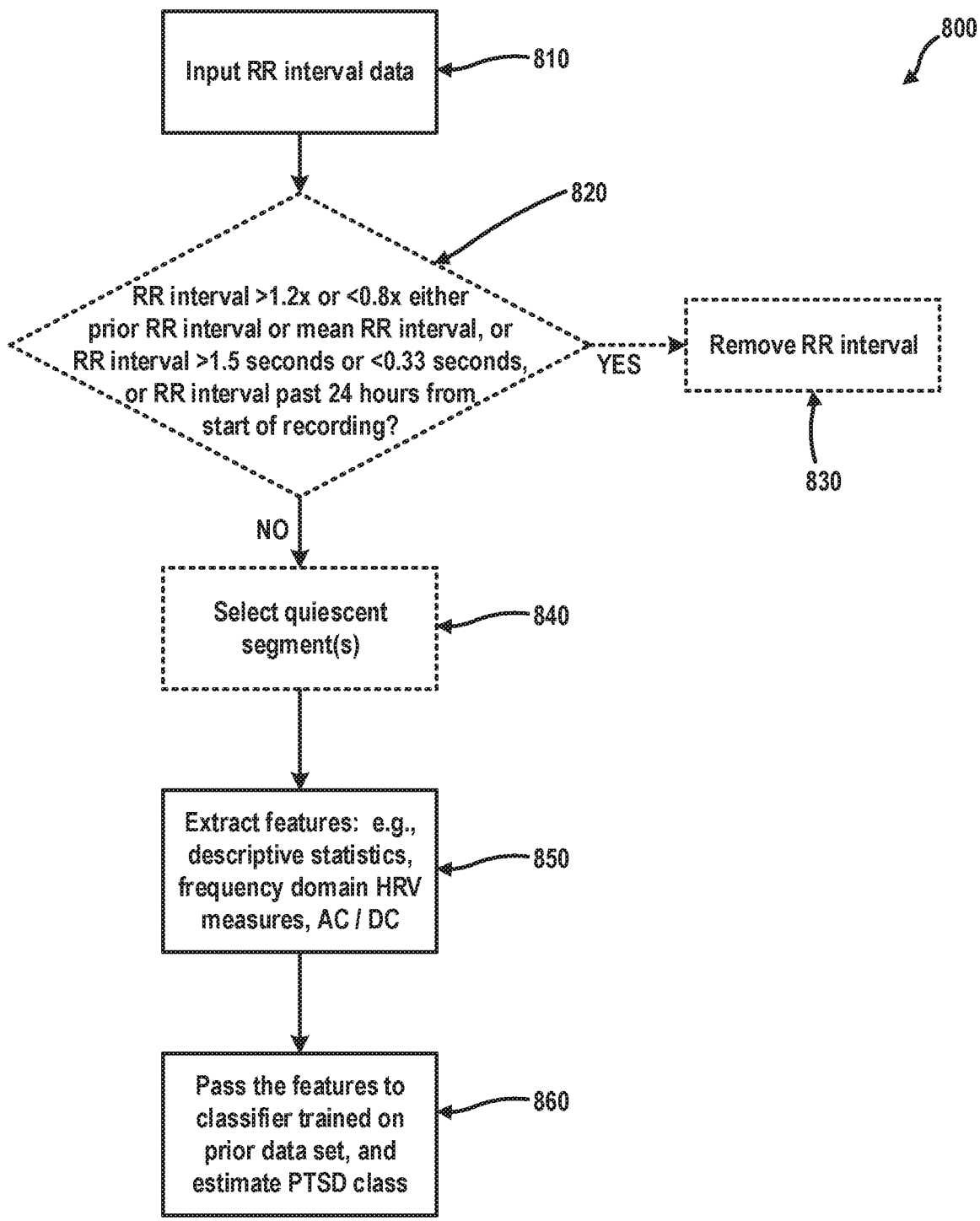
FIG. 21 is a flow diagram of an example method for classifying PTSD.

The following is a method for determining or selecting a quiescent segment according to one or more embodiments, and the following method may be used at 720 of FIG. 20 or at 820 of FIG. 21 for selecting quiescent segments. The following example uses an electrocardiograph and electrocardiography information, but one skilled in the art would appreciate that other collection devices (such as wearables incorporating photoplethysmography) and photoplethysmography can be used.

Using a sliding 10-minute window on information from electrocardiography 1535 performed on an individual 1010, find five non-overlapping 10-minute periods of lowest median HR; these five periods are quiescent segments.

RR interval data from the median quiescent segment of these five periods may be used to calculate HRV features, but the embodiments are not limited thereto. The median quiescent segment may be determined by taking the median quiescent segment in an ordering of the five quiescent segments by the median heart rate of each quiescent segment. The median quiescent segment may be determined by taking the median quiescent segment in an ordering of the five quiescent segments by the average heart rate of each quiescent segment.

FIG. 20 is a flow diagram of an example method (700) for training a classifier that classifies a PTSD status. First, RR interval data is input (710). The RR interval data may be information from electrocardiography 1535 performed on one individual, multiple individuals, or both. RR interval data may be excluded if a duration of a recording of RR interval data does not meet a threshold (e.g. less than 24 hours). The RR interval data may be input to a computing device. Optionally, second, at 720, an RR interval is removed (730) if any of the following are true: the RR interval is greater than 1.2 times or less than 0.8 times either the prior RR interval or a mean RR interval, the RR interval is greater than 1.5 seconds or less than 0.33 seconds, or the RR interval occurs more than 24 hours past the start of recording. Optionally, third, at least one quiescent segment is selected (740). Fourth, features are extracted (750) from the RR interval data. The features may include descriptive statistics, frequency domain HRV measures, AC, DC, the phase of the median quiescent window (time of day normalized to radians), basic RR interval statistics (mean, median, mode, standard deviation, interquartile range, skewness, and kurtosis), power spectral measures (VLF, LF, HF, total power), and/or other measures of the distribution of RR intervals (NNN, MNN, PNN, PNN50, RMSSD, and/or SDNN. Fifth, training and test data are distributed, and k-fold cross-validation is performed (760). Sixth, a classifier is trained (770) on the features and labels. The classifier may be trained using a computing device. Optionally, seventh, the classifier's performance is assessed (780) on test sets.

FIG. 21 is a flow diagram of an example method (800) for classifying a PTSD status. First, RR interval data is input (810). The RR interval data may be information from electrocardiography 1535 performed on an individual. RR interval data may be excluded if a duration of a recording of RR interval data does not meet a threshold (e.g. less than 24 hours). The RR interval data may be input to a computing device. Optionally, second, at 820, an RR interval is removed (830) if any of the following are true: the RR interval is greater than 1.2 times or less than 0.8 times either the prior RR interval or a mean RR interval, the RR interval is greater than 1.5 seconds or less than 0.33 seconds, or the RR interval occurs more than 24 hours past the start of recording. Optionally, third, at least one quiescent segment is selected (840). Fourth, features are extracted (850) from the RR interval data. The features may include descriptive statistics, frequency domain HRV measures, AC, DC, the phase of the median quiescent window (time of day normalized to radians), basic RR interval statistics (mean, median, mode, standard deviation, interquartile range, skewness, and kurtosis), power spectral measures (VLF, LF, HF, total power), and/or other measures of the distribution of RR intervals (NNN, MNN, PNN, PNN50, RMSSD, and/or SDNN. Fifth, the features are passed to the classifier trained on a prior data set, and a PTSD class is estimated (860).

Figure 23:
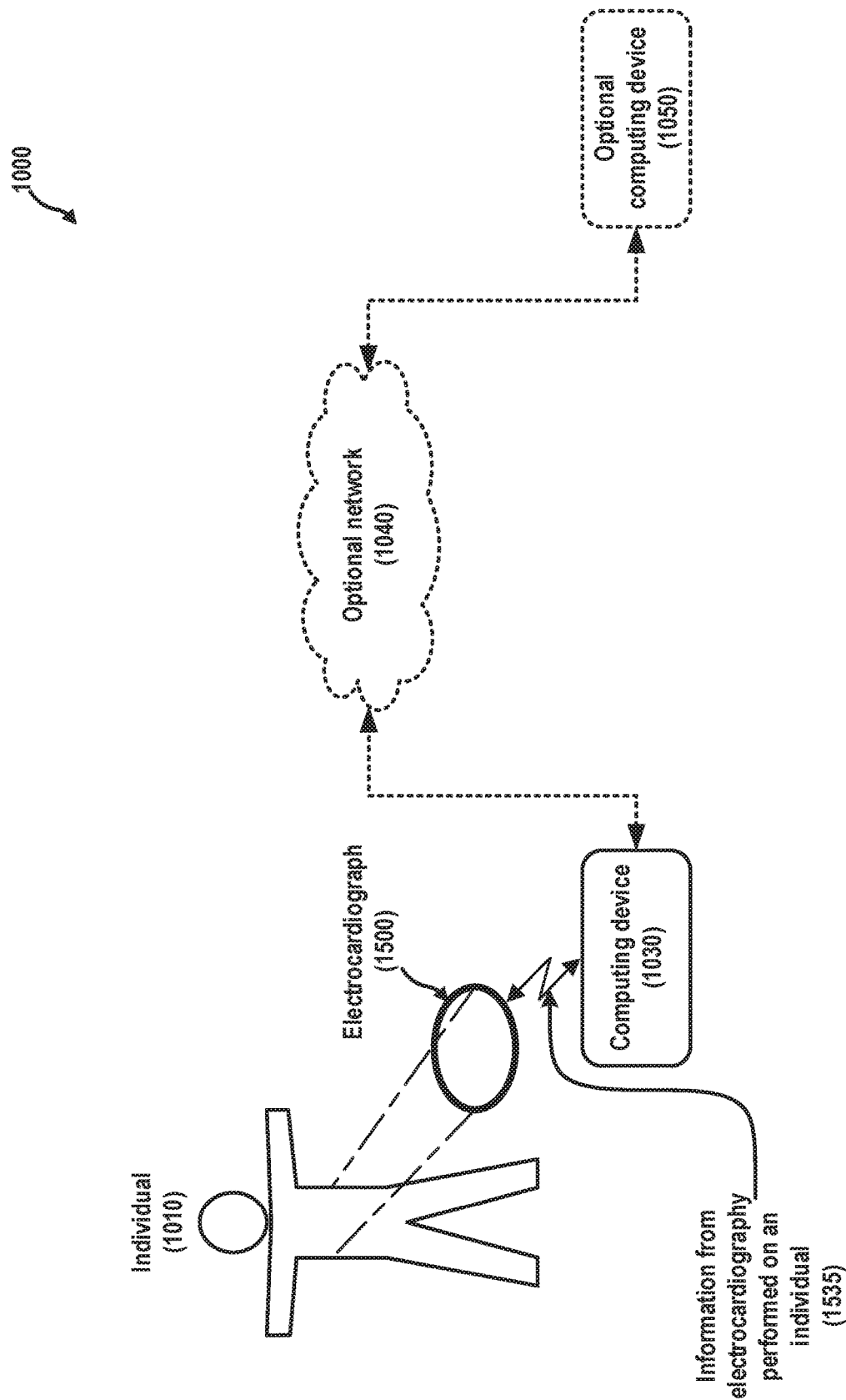
FIG. 23 is a high-level diagram of a system for classifying PTSD and/or for training a classifier to classify PTSD.

FIG. 23 is a high-level diagram of a system (1000) for classifying a PTSD status and/or for training a classifier to classify a PTSD status. Individual 1010 wears an electrocardiograph 1500 to obtain information from electrocardiography performed on an individual (1535). The electrocardiograph 1500 may be, without limitation, a heart rate monitor or a Holter monitor. The electrocardiograph 1500 may be an adhesive-type electrocardiograph that, when worn, looks similar to a large adhesive bandage. The electrocardiograph (1500) may transmit information from electrocardiography (1535) performed on an individual (1010) to a computing device 1030. The computing device 1030 may be, for example, a personal computer, a smartphone, or a tablet computer. The electrocardiograph (1500) may transmit information from electrocardiography performed on an individual (1535) to the computing device 1030 wirelessly using a protocol such as Bluetooth or Bluetooth Smart (Bluetooth low energy). Other protocols may include a proprietary protocol or a protocol based on IEEE 802.15.4 such as Zigbee. In at least one embodiment, the electrocardiograph 1500 may include a SIM card and circuitry to communicate with a base station in a cellular network. In at least one embodiment, the electrocardiograph 1500 may communicate with a platform in the cloud such as Philips Healthsuite or Samsung ARTIK Cloud.

In at least one embodiment, the computing device 1030 (e.g. OnHub SRT-AC1900 by Asus and Google) can receive information via IEEE 802.15.4 or Bluetooth and transmit information to another computing device (e.g. a smartphone or a computing device in the cloud) via, for example, IEEE 802.11ac or over a wide area network using, e.g., a LTE connection or Ethernet. A protocol such as Bluetooth Smart or a protocol based on IEEE 802.15.4 generally requires less power than a protocol like IEEE 802.11ac, thereby helping preserve battery life of a computing device 1030 or an electrocardiograph 1500. The electrocardiograph (1500) may have the ability to switch between or among different wireless protocols to reduce power demand or increase wireless range, depending on the capabilities of the computing device(s) to which it transmits information. The electrocardiograph 1500 may be connected to the computing device 1030 by an Ethernet connection or a wired connection (e.g. USB). In at least one embodiment, the computing device 1030 is integral with the electrocardiograph 1500. In at least one embodiment, the computing device 1030 is a computing device 1220 accessed by a healthcare provider involved in the diagnosis or reporting of a PTSD status to the individual 1010.

In at least one embodiment, the computing device (1030) may transmit information over a network (1040) (e.g. the Internet) to another computing device (1050). The information may include information from electrocardiography 1535 performed on the individual 1010, features determined from information from electrocardiography 1535 performed on the individual 1010, a PTSD status, and/or RR interval information. The computing device 1050 may be part of software as a service (SaaS) or cloud computing infrastructure. In at least one embodiment, the computing device 1050 is a computing device 1220 accessed by a healthcare provider involved in the diagnosis or reporting of a PTSD status to the individual 1010.

Computing device (1030) may implement all or a portion of electrocardiography information processing unit (1100). Computing device (1050) may implement all or a portion of electrocardiography information processing unit (1100).

As used herein, information from electrocardiography includes information in a signal received by an electrocardiograph and information transmitted or stored by an electrocardiograph. Information from electrocardiography may include an analog signal or data resulting from converting an analog signal to digital information.

As used herein, a PTSD status may include PTSD-positive (e.g. diagnosed with, or classified as having, PTSD), PTSD-negative (e.g. determined by a professional healthcare provider as not having PTSD, or classified as not having PTSD), a severity of PTSD, and/or a probability of having PTSD.

Figure 24:
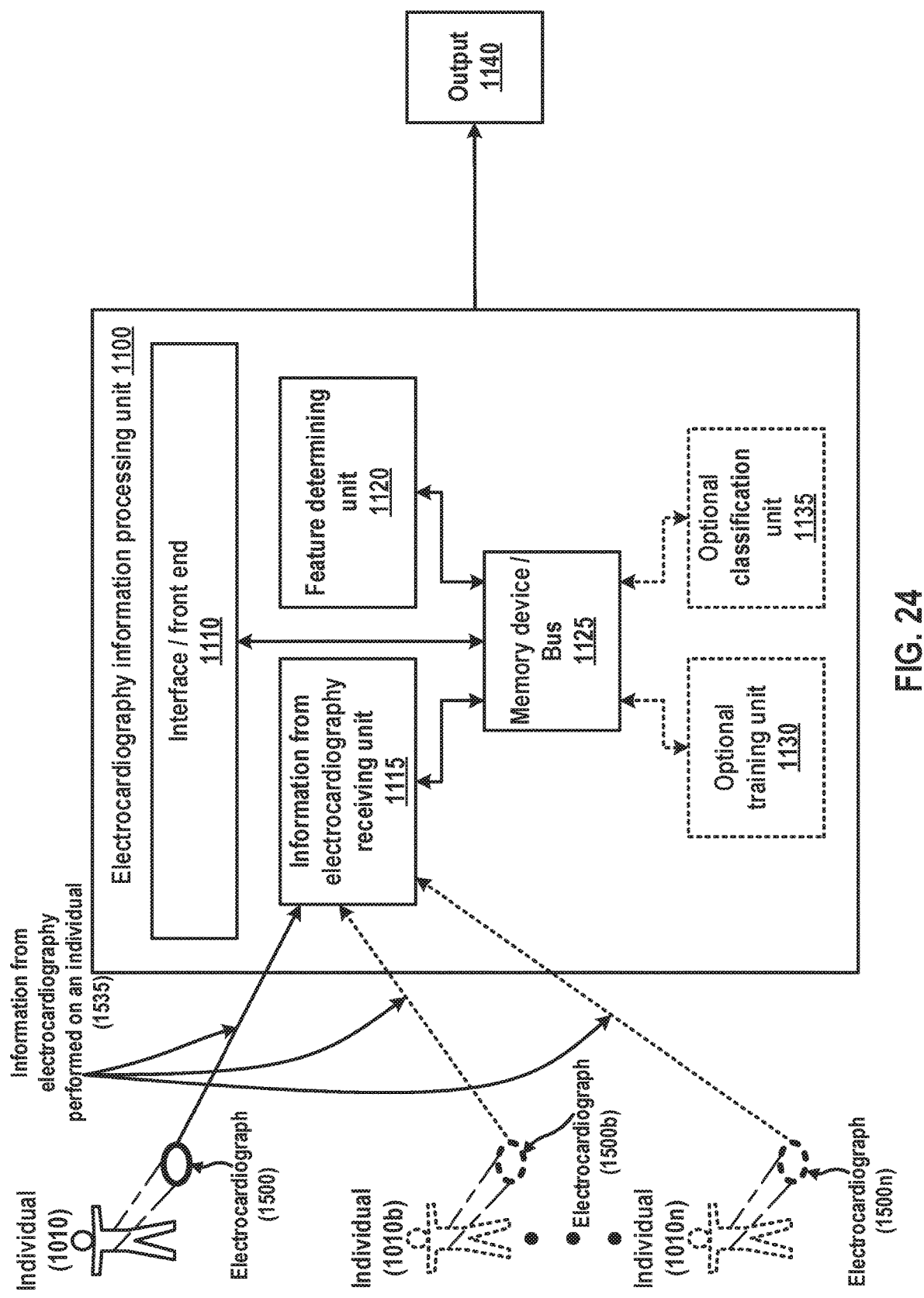
FIG. 24 is a block diagram of an electrocardiography information processing unit according to at least one embodiment.

FIG. 24 is a block diagram of an electrocardiography information processing unit (1100) according to at least one embodiment. Electrocardiography information processing unit (1100) may include interface/front end (1110), information from electrocardiography receiving unit (1115), feature determining unit (1120), and a memory device/bus (1125). Electrocardiography information processing unit (1100) may optionally include an optional training unit (1130). Electrocardiography information processing unit (1100) may optionally include an optional classification unit (1135).

The electrocardiography information processing unit (1100) receives information from electrocardiography 1535 performed on an individual (1010). The electrocardiography information processing unit (1100) provides an output (1140). The output (1140) may be a PTSD status, a severity of PTSD, a probability of PTSD, quiescent segments, RR interval data, an error message, a feature determined or extracted by the feature determining unit (1120), etc. The output (1140) may be a model, including a model trained or learned by the optional training unit (1130). The output (1140) may be a machine learning model, including a machine learning model trained or learned by the optional training unit (1130). The output (1140) may be displayed on a display. A PTSD status may be determined rapidly, by using a computing device, upon completion of receiving information from electrocardiography 1535 performed on an individual 1010. A PTSD status may be determined securely and rapidly, by using a computing device 1220, upon request by a healthcare provider.

Information from electrocardiography receiving unit (1115) receives information from electrocardiography 1535 performed on an individual (1010). The information from electrocardiography receiving unit (1115) may provide the information from electrocardiography 1535 performed on an individual (1010) to the memory device/bus (1125).

Feature determining unit (1120) determines or extracts features from the information from the electrocardiography 1535 performed on the individual (1010). The features may include or be based on at least one quiescent segment. The feature determining unit (1120) may determine a quiescent segment. The features may include RR interval information, quiescent segments of RR interval information, lowest median HR, acceleration capacity (AC), deceleration capacity (DC), total power, low frequency (LF) power, very low frequency (VLF) power, standard deviation of all normal RR intervals (SDNN), a phase of a median quiescent segment window, a mode of RR intervals, a median of RR intervals, a standard deviation of RR intervals, an interquartile range of RR intervals, a skewness of RR intervals, a kurtosis of RR intervals, a PTSD status, a severity of PTSD, and/or a probability of PTSD. The feature determining unit (1120) may determine a feature vector including one or more features. The feature determining unit (1120) may provide features or feature vectors to the memory device/bus (1125).

The features may be determined using a computing device. A feature vector may comprise a data structure with at least one value determined by the computing device based the information from electrocardiography 1535 performed on an individual 1010. Each feature vector may be associated with a label. The label may be a classification which a model will provide as output when the model is used as a classifier for classification or determination of a PTSD status. The label may be, without limitation, a PTSD status, a severity of PTSD, a probability of PTSD, or a quiescent segment.

The electrocardiography information processing unit (1100) may optionally include an optional training unit (1130). The optional training unit may receive from the memory device/bus 1125 the features or feature vectors that the feature determining unit 1120 provided to the memory device/bus 1125. The optional training unit may further receive a label associated with each feature or feature vector. The optional training unit 1130 may train a model or a machine learning model. The optional training unit 1130 may use a machine learning algorithm implemented on a computing device to train the model or machine learning model.

In the case that the electrocardiography information processing unit 1100 includes the optional training unit 1130, the information from electrocardiography receiving unit 1115 may receive information from electrocardiography 1535 performed on individuals 1010, 1010b, ... 1010n, n≥2. The memory device/bus 1125 may provide the information from electrocardiography 1535 performed on individuals 1010, 1010b, ..., 1010n, to the feature determining unit 1120. The feature determining unit 1120 may determine features or a feature vector related to each individual 1010, 1010b ... 1010n, and may receive as input a label associated with each individual 1010, 1010b ... 1010n. The memory device/bus 1125 may provide the features or feature vector related to each individual 1010, 1010b ... 1010n, and any respective labels, to the optional training unit 1130.

A model (e.g. machine learning model) may be a kernel or learned classifier, and determining features and comparing a feature vector to the model may involve computational complexity exceeding what is feasible for a person. That is, some data classification problems, such as determining a PTSD status or training a classifier that determines a PTSD status, may require a technical solution (e.g. implementation on a computing device) due to their computational complexity. This technical solution may lead to the technical effect of reporting a PTSD status based on features determined from information from electrocardiography 1535 performed on an individual 1010.

An ensemble of models may be used via boosting or another ensemble method. The model may be any one of many methods for classification or regression known in the art. The model may be an artificial neural network, a Bayesian graphical model, a Gaussian process, a logistic regression, a support vector machine, a decision tree, a hidden Markov model, or k-nearest neighbor. K-fold cross-validation may be used. The optional training unit (1130) may provide the model to the memory device/bus (1125).

The optional classification unit (1135) classifies information from electrocardiography 1535 performed on an individual 1010 by comparing features or a feature vector associated with the information from electrocardiography 1535 performed on the individual 1010 to the model. The model may be a model trained by the optional training unit (1130). The optional classification unit (1135) may provide the output (1140). The optional classification unit (1135) may use an unsupervised learning method such as clustering or hierarchical clustering to classify features or a feature vector. The optional classification unit (1135) may provide the classification or output (1140) to the memory device/bus (1125).

Note the training unit (1130) is optional. The model (e.g. machine learning model) may be provided as input to the electrocardiography information processing unit 1100 in an embodiment where the model is a predetermined model.

The memory device/bus (1125) may comprise a system bus, memory bus, volatile storage, and/or non-volatile storage. Further, the memory device/bus (1125) may comprise a bus connecting multiple computers. The memory device/bus may connect computers via a network or Internet connection. That is, the various components in the electrocardiography information processing unit 1100 may be part of a distributed computing system, and the memory device/bus (1125) may connect the various components in the distributed computing system. Thus, the memory device/bus (1125) may include a network connection and equipment such as routers, gateways, network adapters, base stations (e.g. eNodeB), etc., to enable the various components of the electrocardiography information processing unit 1100 to communicate and perform methods, including the methods described herein. The memory device/bus (1125) communicates information between or among various portions of the electrocardiography information processing unit 1100, including the interface/front end (1110). The memory device/bus (1125) may provide the output (1140) to e.g. the individual 1010, a healthcare provider 1240, or the interface/front end (1110).

Interface/front end (1110) may comprise an output device such as a display (e.g. monitor) or a speaker, etc. Interface/front end (1110) may further comprise an input device such as a keyboard, mouse, microphone, etc. Interface/front end (1110) may be web-based. Interface/front end (1110) may be the interface/front end (1230). Interface/front end (1110) may report or indicate the output (1140).

Figure 25:
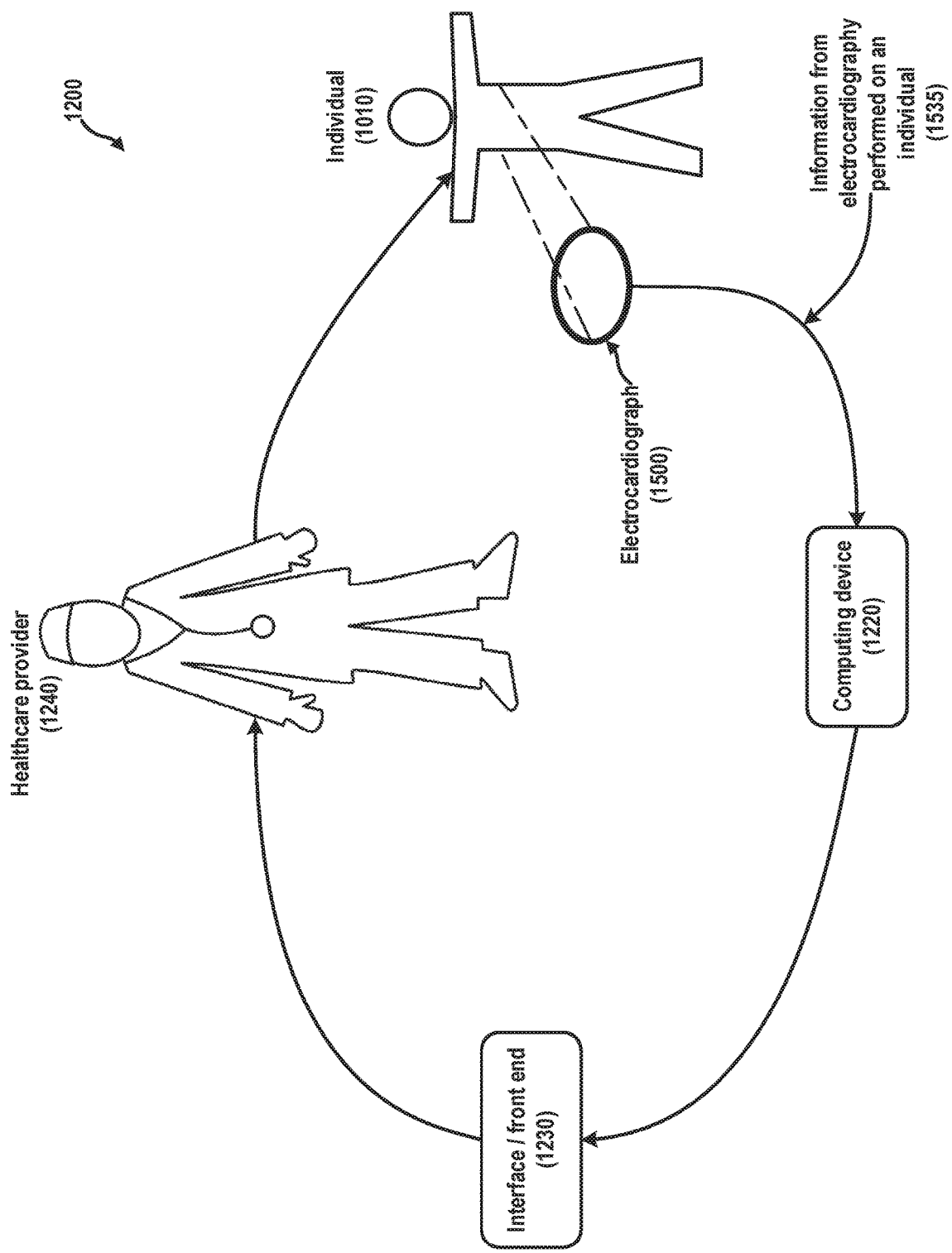
FIG. 25 is a high-level block diagram of a system and/or method for professional monitoring of a PTSD status according to at least one embodiment.

FIG. 25 is a high-level block diagram of a system and/or method (1200) for professional monitoring of a PTSD status according to at least one embodiment. Information from electrocardiography 1535 performed on the individual 1010 using the electrocardiograph 1500 is provided to a computing device 1220. The computing device 1220 may implement the electrocardiography information processing unit 1100. Note given the structure of memory device/bus 1125, the computing device 1220 may comprise multiple computing devices, including computing device 1030 and/or 1050. Computing device 1220 may provide information (e.g. output 1140) to the interface/front end 1230. Computing device 1220 may be part of, or in communication with, a cloud platform such as Philips Healthsuite or Samsung ARTIK Cloud.

The interface/front end (1230) may be a secure interface compliant with privacy or healthcare regulations such as HIPAA. The interface/front end (1230) may be the interface/front end (1110).

The healthcare provider 1240 may obtain information (e.g. output 1140) from the interface/front end (1230). For example, the healthcare provider 1240 may interpret information from electrocardiography 1535 performed on the individual 1010, features or a feature vector determined by the feature determining unit 1120, and/or a classification determined by the classification unit 1135. The healthcare provider 1240 may determine or diagnose a PTSD status based on the information from the interface/front end (1230). The healthcare provider 1240 may provide information (e.g. output 1140) to the individual 1010.

In certain aspects, systems and methods as described herein can provide data for PTSD treatment efficacy over time. In at least one embodiment, the healthcare provider 1240 provides ongoing monitoring to the individual 1010. The healthcare provider 1240 may monitor the individual's 1010 PTSD severity or status over the course of multiple days or multiple healthcare provider visits. The healthcare provider 1240 may receive information from electrocardiography 1535 performed on the individual 1010 or output 1140 in real-time. Therefore, in the case of an emergent PTSD issue, healthcare provider may be advised by the interface/front end (1230) of the emergent PTSD issue rapidly. The healthcare provider 1240 may provide a PTSD intervention which may be administered at the healthcare provider's 1240 location (e.g. hospital or out-patient clinic) and/or the individual's 1010 location (e.g. home and/or place of work). The system 1200 may facilitate the healthcare provider's 1240 ongoing monitoring of the PTSD intervention provided to the individual 1010. In certain aspects, information from the ongoing monitoring can provide data to the individual, healthcare provider, or both which can be used to assess the effectiveness of PTSD treatment over time or at a specific time point.

Figure 26:
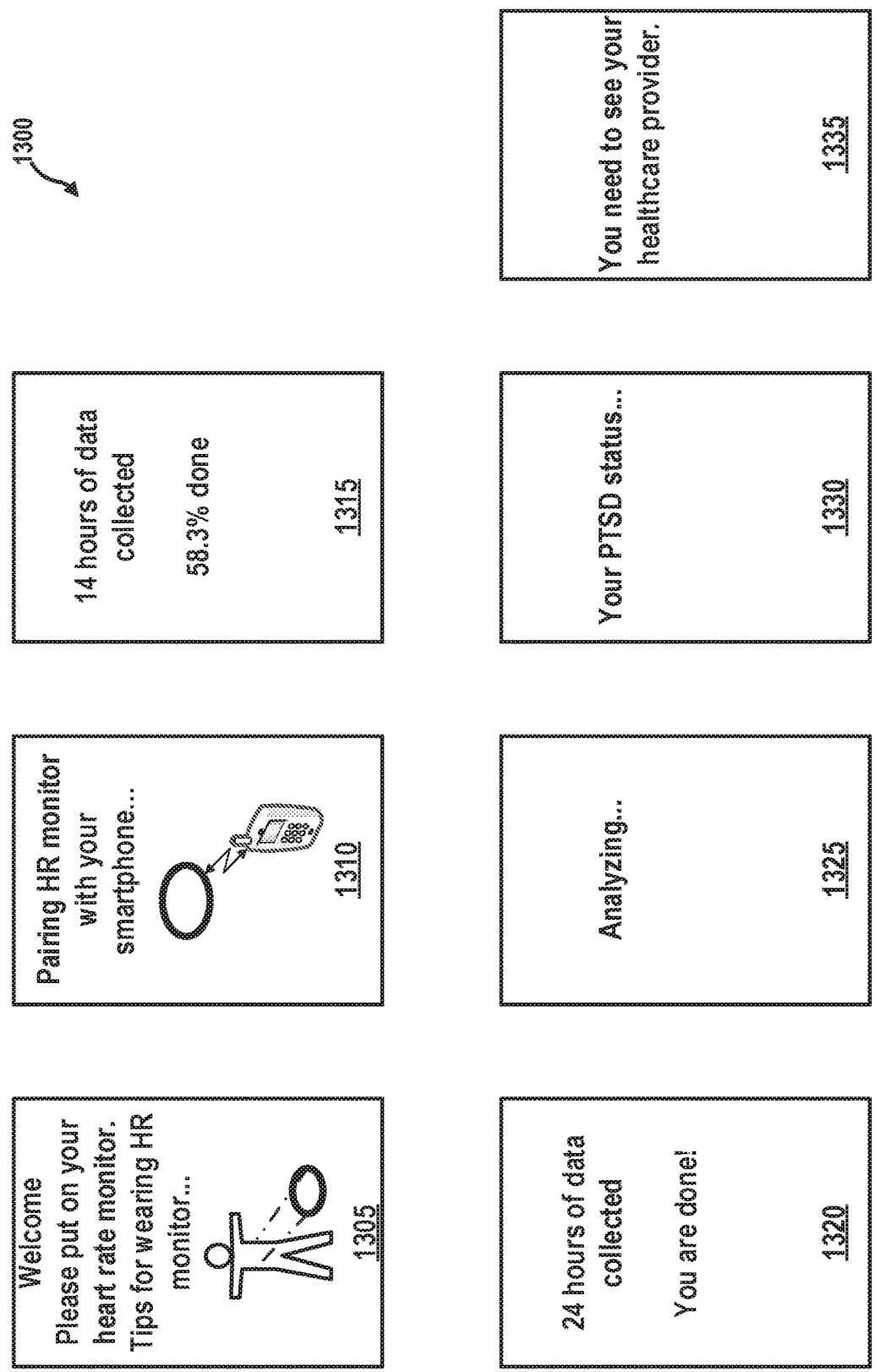
FIG. 26 is an illustration of a user interface of software for receiving information from electrocardiography performed on an individual according to at least one embodiment.

FIG. 26 is an illustration of a user interface of software (1300) for receiving information from electrocardiography 1535 performed on an individual 1010 according to at least one embodiment. The software (1300) may be provided on a computing device, such as computing device (1030), computing device (1050), or computing device (1220). Software (1300) may be an implementation of all or a portion of electrocardiography information processing unit 1100. At image 1305, software 1300 may advise individual 1010 to put on the electrocardiograph 1500 and may be provided with instructions on how to put on the electrocardiograph 1500. At image 1310, software 1300 may advise individual 1010 of an attempt to make a communication link between the electrocardiograph 1500 and a computing device 1030. Once the communication link is established, at image 1315, the individual 1010 may be advised of an amount of information from electrocardiography 1535 performed on the individual 1010 that has been received. After an appropriate or predetermined amount of time has elapsed, at image 1320, the software 1300 may advise the individual 1010 that no further receipt of information from electrocardiography 1535 is required. At image 1325, the software 1300 may advise the individual 1010 that the software 1300 is processing the information from electrocardiography 1535, and this processing may comprise determining features from the information from electrocardiography 1535, comparing the features to a model (e.g. a classifier), and/or determining a PTSD status of the individual 1010 based on the comparison of the features to the model. At image 1330, the software 1300 may advise the individual 1010 of information such as an output 1140 (e.g. a PTSD status). At image 1335, the software 1300 may advise the individual 1010 of additional advice or recommendations based on the information provided at image 1330. For example, if a PTSD status is positive or of a certain severity, the software 1300 may advise the individual 1010 to see the healthcare provider 1240.

Figure 29:
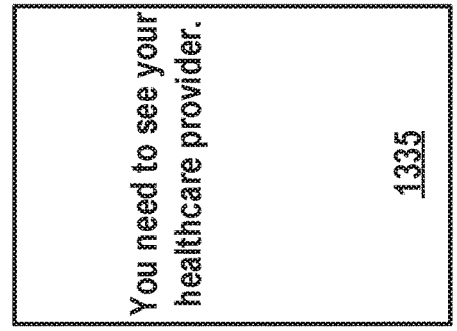
FIG. 29 is an illustration of a user interface of software for receiving information from electrocardiography performed on an individual according to at least one embodiment.
Figure 29:
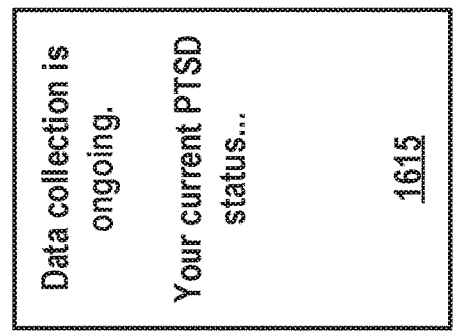
Figure 29:
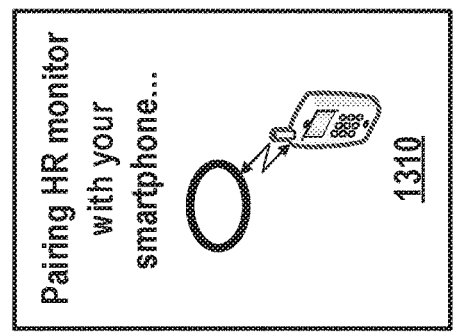
Figure 29:
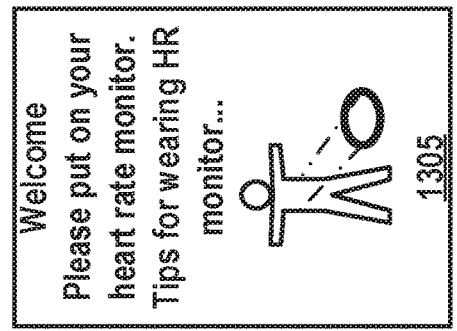

FIG. 29 is an illustration of a user interface of software (1600) for receiving information from electrocardiography performed on an individual according to at least one embodiment. The software (1600) may be designed for ongoing receipt of information from electrocardiography 1535. The software (1600) may be provided on a computing device, such as computing device (1030), computing device (1050), or computing device (1220). Software (1600) may be an implementation of all or a portion of electrocardiography information processing unit 1100. At image 1305, software 1600 may advise individual 1010 to put on the electrocardiograph 1500 and may be provided with instructions on how to put on the electrocardiograph 1500. At image 1310, software 1600 may advise individual 1010 of an attempt to make a communication link between the electrocardiograph 1500 and a computing device 1030. Once the communication link is established, at image 1615, software 1600 may advise the individual 1010 that information from electrocardiography 1535 performed on the individual 1010 is being received. Software 1600 may perform processing comprising determining features from the information from electrocardiography 1535, comparing the features to a model (e.g. a classifier), and/or determining a PTSD status of the individual 1010 based on the comparison of the features to the model. Also at image 1615, the software 1600 may advise the individual 1010 of information such as an output 1140 (e.g. a PTSD status). At image 1335, the software 1600 may advise the individual 1010 of additional advice or recommendations based on the information provided at image 1615. For example, if a PTSD status is positive or of a certain severity, the software 1600 may advise the individual 1010 to see the healthcare provider 1240.

Figure 27:
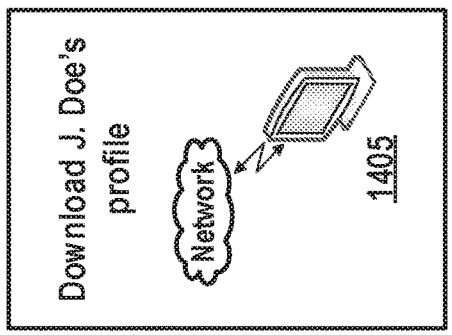
FIG. 27 is an illustration of a user interface of software for professional monitoring of a PTSD status according to at least one embodiment.
Figure 27:
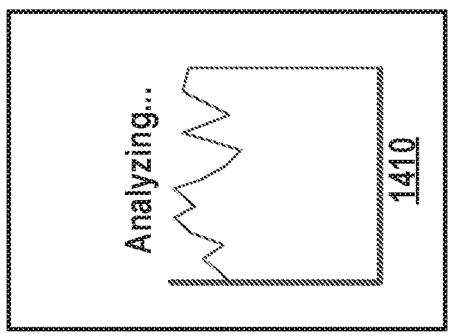
Figure 27:
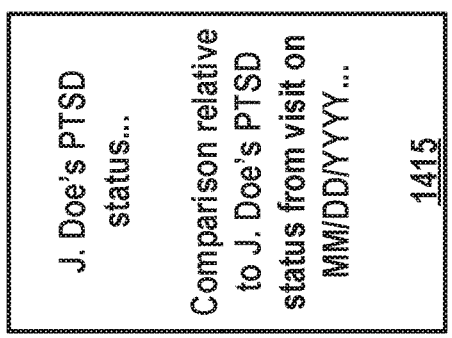
Figure 27:
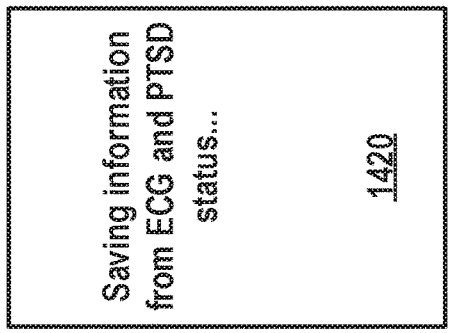

FIG. 27 is an illustration of a user interface of software (1400) for professional monitoring of a PTSD status according to at least one embodiment. The software (1400) may be provided on a computing device, such as computing device (1030), computing device (1050), or computing device (1220). The software may be presented to the healthcare provider 1240 by the interface/front end 1230. Software (1400) may be an implementation of all or a portion of electrocardiography information processing unit 1100. At image 1405, software 1400 may provide an interface to access information from electrocardiography 1535 performed on the individual 1010 or an output 1140 (e.g. a PTSD status), and the interface may be a secure interface complaint with healthcare or privacy regulations (e.g. HIPAA). At image 1410, the software 1400 may advise the healthcare provider 1240 that the software 1400 is processing (e.g. processing the information from electrocardiography 1535 or determining an output 1140 (e.g. a PTSD status)), and this processing may comprise determining features from the information from electrocardiography 1535, comparing the features to a model (e.g. a classifier), and/or determining a PTSD status of the individual 1010 based on the comparison of the features to the model. At image 1415, the software 1400 may advise the healthcare provider 1240 of information such as an output 1140 (e.g. a PTSD status). Also at image 1415, the software 1400 may provide information such as a comparison relative to a prior access of information from electrocardiography 1535 performed on the individual 1010 or a prior output 1140 (e.g. a prior PTSD status). Therefore, software 1400 may provide ongoing information of a PTSD status. At image 1420, software 1400 may provide an interface to save information from electrocardiography 1535 performed on the individual 1010 or an output 1140 (e.g. a PTSD status) so that saved information can be retrieved at a later time.

Figure 28:
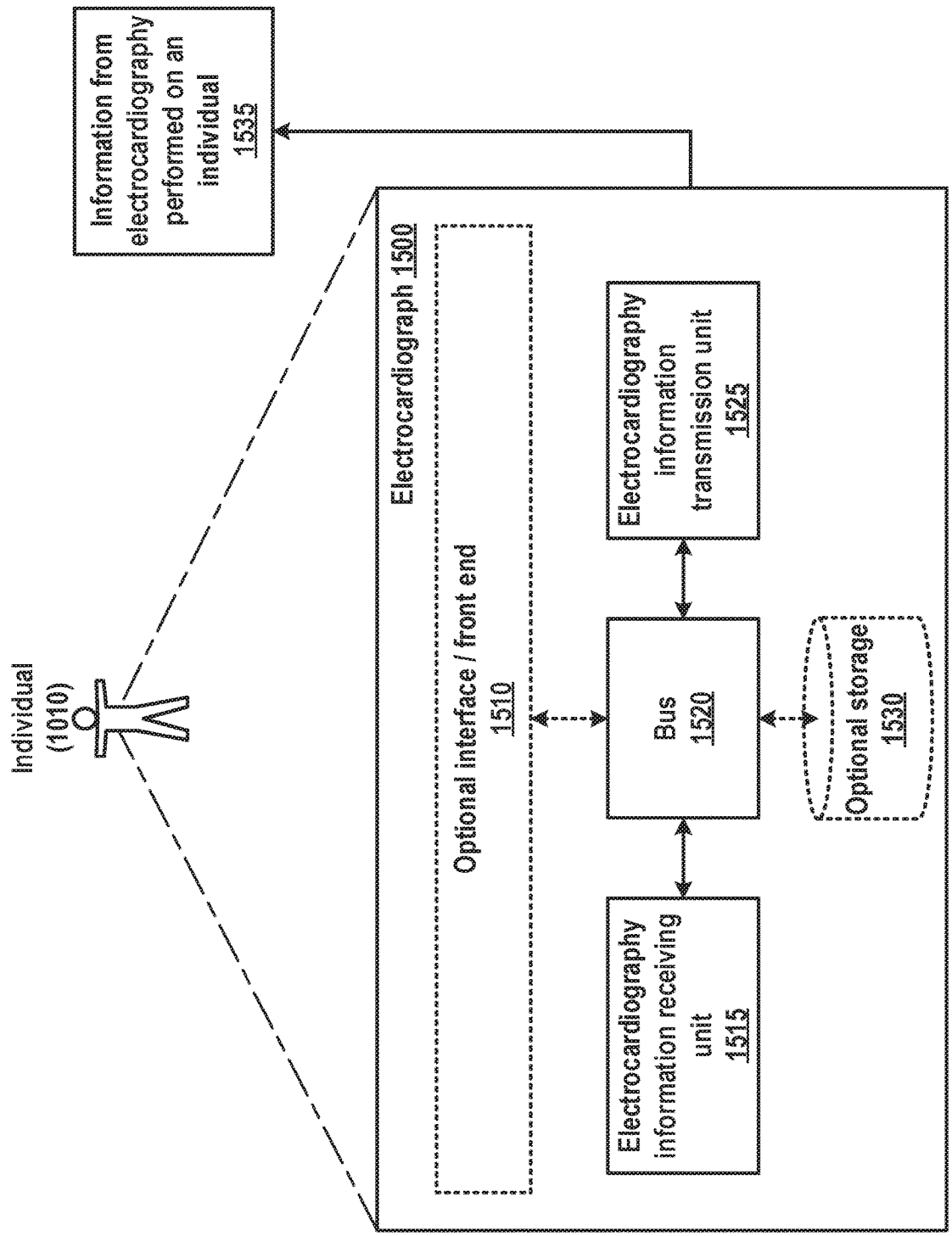
FIG. 28 is a high-level block diagram of an electrocardiograph according to at least one embodiment.

FIG. 28 is a high-level block diagram of an electrocardiograph (1500) according to at least one embodiment. Electrocardiograph 1500 includes electrocardiography information receiving unit 1515, bus 1520, and electrocardiography information transmission unit 1525. Optionally, electrocardiograph 1500 may include optional interface/front end 1510. Optionally, electrocardiograph 1500 may include optional storage 1530.

Individual 1010 wears or is in communication with electrocardiograph 1500 such that electrocardiography information receiving unit 1515 receives a heart signal from individual 1010. Electrocardiography information receiving unit 1515 may be in electronic communication with bus 1520. Electrocardiography information transmission unit 1525 may be in electronic communication with bus 1520. In certain embodiments, the electrocardiograph 1500 can be a heartrate monitor.

Electrocardiography information transmission unit 1525 may transmit information from electrocardiography performed on an individual 1535 using transmission methods disclosed herein, including the transmission methods disclosed herein with respect to electrocardiograph 1500.

Optional interface/front end (1510) may report a PTSD status that is determined using one or more of the methods disclosed herein. Optional interface/front end (1510) may comprise a display (e.g. LCD or LED display), an audio speaker, a vibration generator, a tactile feedback generator, and/or one or more LEDs. Optional interface/front end (1510) may report any of the following: that a heart signal is or is not being received, an amount of time that a heart signal has been received, an amount of time remaining for heart signal reception, that information from electrocardiography performed on an individual has been saved to optional storage 1530, and/or a status of transmission of information from electrocardiography performed on an individual. A status of transmission of information from electrocardiography performed on an individual may include any of the following: that the electrocardiograph 1500 is attempting to pair (via e.g. a Bluetooth protocol, a IEEE 802.15.4 protocol, or a IEEE 802.11 protocol) with another device, that the electrocardiograph 1500 is or is not paired with another device, and/or that the electrocardiograph is, or has completed, transmitting information from electrocardiography from an individual 1535.

The amount of information received by the electrocardiography information receiving unit 1515 will depend on factors including sampling frequency and duration of sampling of a heart signal. Given the methods disclosed herein, an advantageous amount of optional storage 1530 may be determined. In at least one embodiment, optional storage 1530 is sufficient to store an amount of heart signal appropriate to determine a PTSD status, and in this embodiment, information from electrocardiography performed on an individual 1535 may not need to be transmitted by the electrocardiography information transmission unit 1525 until the entire amount of heart signal appropriate to determine a PTSD status has been received by the electrocardiography information receiving unit 1515 and/or stored by the optional storage 1530. Other factors, including mass and cost of optional storage 1530 and mass and cost of any battery included in electrocardiograph 1500, may affect design preferences pertaining to a battery, an optional storage 1530, and a design of the electrocardiography information transmission unit 1525.

The implementation of the optional storage 1530 may be done using a volatile or non-volatile storage comprising memory such as flash or 3D XPoint (e.g. Intel Optane or Micron QuantX). Further, the electrocardiograph 1500 may include an analog to digital converter, an electrode, a transducer, a microprocessor, and/or a system on a chip (SoC). The transducer may receive a heart signal from an individual 1010.

Figure 30:
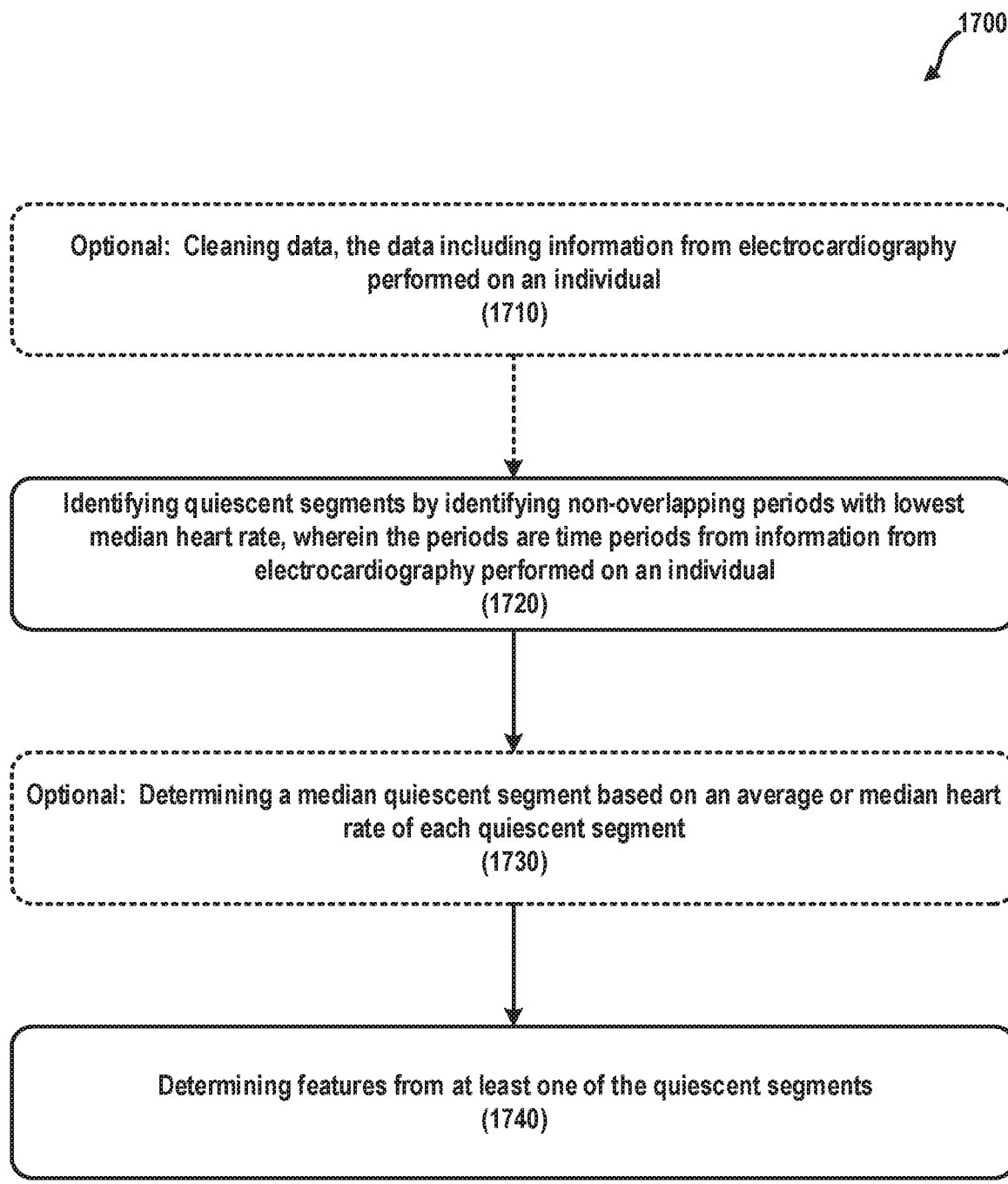
FIG. 30 is a flow diagram illustrating a method for identifying at least one quiescent segment and determining features from the at least one quiescent segment according to at least one embodiment.

FIG. 30 is a flow diagram illustrating a method (1700) for identifying at least one quiescent segment and determining features from the at least one quiescent segment according to at least one embodiment. Optionally, first, data may be cleaned (1710). The data cleaning may be done according to the data cleaning methods disclosed herein and may include one or more exclusion criteria disclosed herein. Second, quiescent segments may be identified (1720) by identifying non-overlapping periods with lowest median heart rate, wherein the periods are time periods from information from electrocardiography 1535 performed on an individual 1010. Optionally, third, a median quiescent segment may be determined (1730) based on an average or median heart rate of each quiescent segment. Fourth, features may be determined (1740) from at least one of the quiescent segments. The determining the features from the at least one of the quiescent segments may include determining features from the median quiescent segment. At least a portion of the method (1700) may be used to select quiescent segment(s) as called for at 740 at FIG. 20 and at 840 at FIG. 21.

Figure 31:
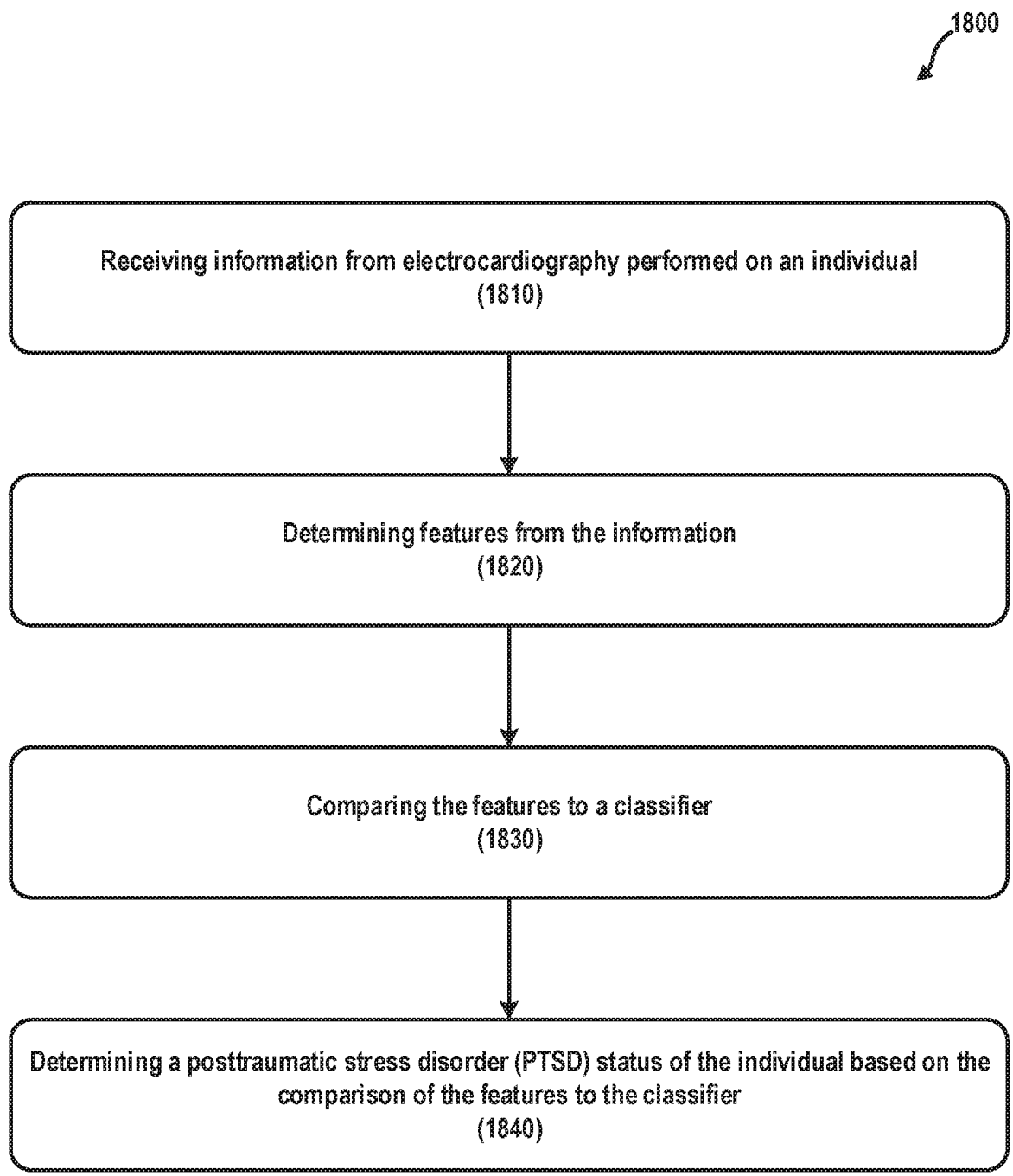
FIG. 31 is a flow diagram illustrating a method for using a classifier to determine a PTSD status according to at least one embodiment.

FIG. 31 is a flow diagram illustrating a method (1800) for using a classifier to determine a PTSD status according to at least one embodiment. First, information from electrocardiography performed on an individual may be received (1810). Second, features may be determined (1820) from the information. Third, the features may be compared (1830) to a classifier. Fourth, based on the comparison of the features to the classifier, a posttraumatic stress disorder (PTSD) status of the individual may be determined (1840).

Figure 32:
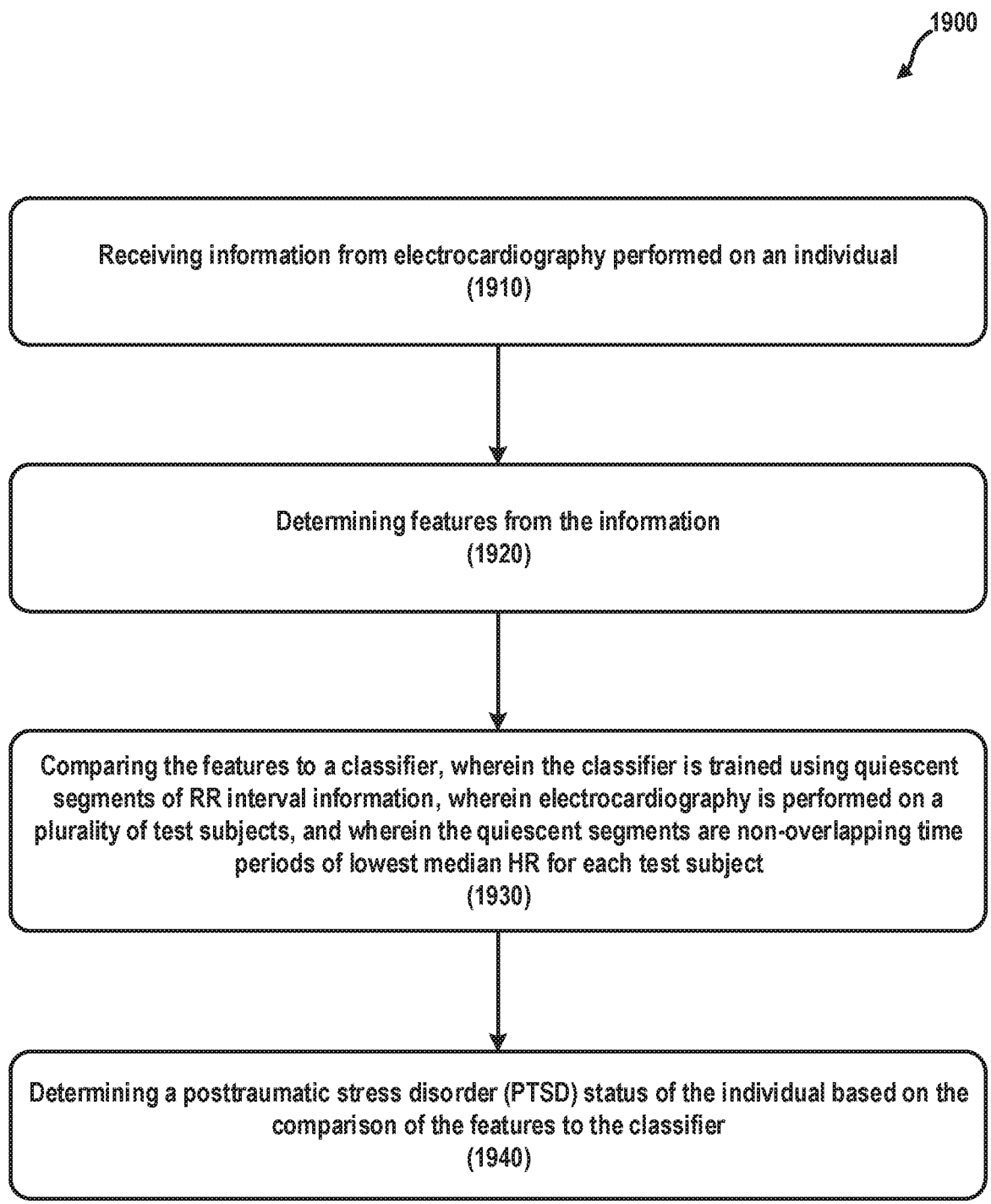
FIG. 32 is a flow diagram illustrating a method for using a classifier to determine a PTSD status according to at least one embodiment.

FIG. 32 is a flow diagram illustrating a method (1900) for using a classifier to determine a PTSD status according to at least one embodiment. First, information from electrocardiography performed on an individual may be received (1910). Second, features may be determined (1920) from the information. Third, the features may be compared (1930) to a classifier, wherein the classifier is trained using quiescent segments of RR interval information, wherein electrocardiography is performed on a plurality of test subjects, and wherein the quiescent segments are non-overlapping time periods of lowest median HR for each test subject. Fourth, based on the comparison of the features to the classifier, a posttraumatic stress disorder (PTSD) status of the individual may be determined (1940).

Figure 22:
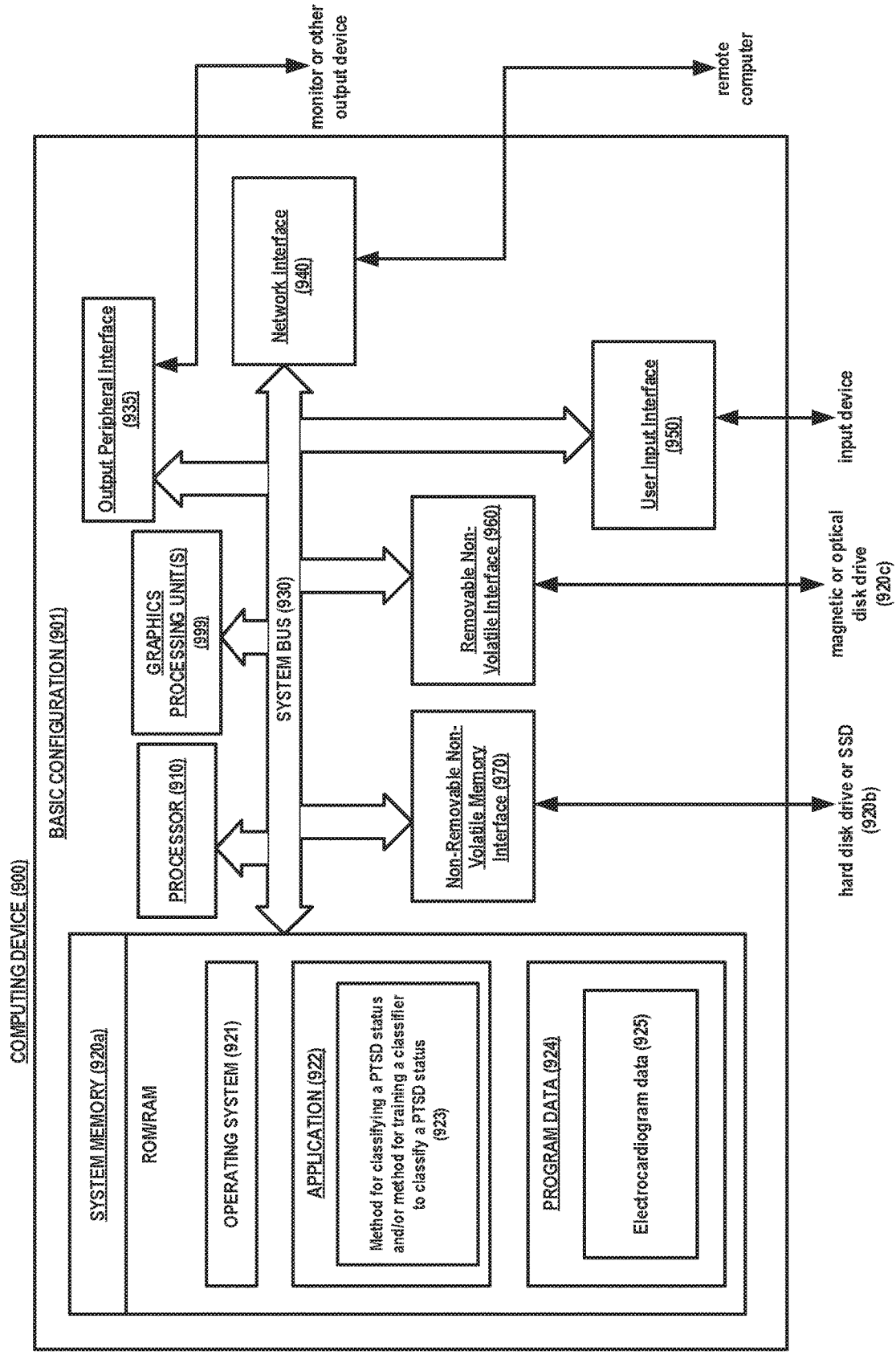
FIG. 22 is a high-level block diagram of an example computer that is arranged for classifying a PTSD status and/or for training a classifier to classify PTSD.

FIG. 22 is a high-level block diagram of an embodiment of an example computer (900) that is arranged for using a classifier to determine a PTSD status and/or for training a PTSD machine learning model. In a very basic configuration (901), the computing device (900) typically includes one or more processors (910) and system memory (920). A system bus (930) can be used for communicating between the processor (910) and the system memory (920).

Depending on the desired configuration, the processor (910) can be of any type including but not limited to a microprocessor (μP), a microcontroller (μC), a digital signal processor (DSP), or any combination thereof. The processor (910) can include one more levels of caching, a processor core, and registers. The processor core can include an arithmetic logic unit (ALU), a floating point unit (FPU), a digital signal processing core (DSP Core), or any combination thereof. A memory controller can also be used with the processor (910), or in some implementations the memory controller can be an internal part of the processor (910).

Depending on the desired configuration, the system memory (920) can be of any type including but not limited to volatile memory (such as RAM), non-volatile memory (such as ROM, flash memory, etc.) or any combination thereof. System memory (920) typically includes an operating system (921), one or more applications (922), and program data (924). The application (922) may include a method for using a classifier to determine a PTSD status and/or a method for training a PTSD machine learning model. Program data (924) includes storing instructions that, when executed by the one or more processing devices, implement a system and method for using a classifier to determine a PTSD status and/or for training a PTSD machine learning model (923). Program data may include (924) may include electrocardiogram data (925). In some embodiments, the application (922) can be arranged to operate with program data (924) on an operating system (921). Program data may include electrocardiogram data (e.g. information from electrocardiography) (925).

The computing device (900) can have additional features or functionality, and additional interfaces to facilitate communications between the basic configuration (901) and any required devices and interfaces, such non-removable non-volatile memory interface (970), removal non-volatile interface (960), user input interface (950), network interface (940), and output peripheral interface (930). A hard disk drive may be connected to the system bus (930) through a non-removable memory interface (970). A magnetic or optical disk drive may be connected to the system bus (930) by the removable non-volatile interface (960). A user of the computing device (900) may interact with the computing device (900) through input devices such as a keyboard, mouse, or other input peripheral connected through a user input interface (950). A monitor or other output peripheral device may be connected to the computing device (900) through an output interface (930) in order to provide output from the computing device (900) to a user or another device.

System memory (920) is an example of computer storage media. Computer storage media includes, but is not limited to, RAM, ROM, EEPROM, flash memory or other memory technology, CD-ROM, digital versatile disk (DVD), Blu-ray Disc (BD) or other optical storage, magnetic cassettes, magnetic tape, magnetic disk storage or other magnetic storage devices, or any other medium which can be used to store the desired information and which can be accessed by computing device (900). Any such computer storage media can be part of the device (900). One or more graphics processing units (GPUs) (999) may be connected to the system bus (930) to provide computing capability in coordination with the processor (910), especially where single instruction, multiple data (SIMD) problems are present.

The computing device (900) can be implemented as a portion of a small-form factor portable (or mobile) electronic device such as a cell phone, a smartphone, a personal data assistant (PDA), a personal media player device, a tablet computer (tablet), a wireless web-watch device, a personal headset device, an application-specific device, or a hybrid device that includes any of the above functions. The computing device (900) can also be implemented as a personal computer including both laptop computer and non-laptop computer configurations. Additionally, the computing device (900) may operate in a networked environment where it is connected to one or more remote computers over a network using the network interface (950).

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will appreciate that the mechanisms of the subject matter described herein are capable of being distributed as a program product in a variety of forms, and that an illustrative embodiment of the subject matter described herein applies regardless of the particular type of non-transitory signal bearing medium used to actually carry out the distribution. Examples of a non-transitory signal bearing medium include, but are not limited to, the following: a recordable type medium such as a floppy disk, a hard disk drive, a solid state drive (SSD), a Compact Disc (CD), a Digital Video Disk (DVD), a Blu-ray disc (BD), a digital tape, a computer memory, etc.

The computing device (1030), the optional computing device (1050), the electrocardiography information processing unit (1100), the computing device (1220), and/or the interface/front end (1230) may be implemented by all or a portion of the computing device (900). Software (1300), software (1400), and/or software (1600) may executed by the computing device (900).

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A method for using a classifier, the method comprising:
receiving measured heart activity information from an individual, a plurality of individuals, or both, the measured heart rate activity information comprising RR interval information and one or more quiescent segments;
determining features from the measured heart rate activity information;
comparing the features to the classifier; and
determining a posttraumatic stress disorder (PTSD) status of the individual based on the comparison of the features to the classifier.

2. The method of claim 1, wherein the classifier is trained using RR interval information from the individual, a plurality of test individuals, or both.

3. The method of claim 2, wherein the classifier is trained using quiescent segments of RR interval information.

4. The method of claim 3, wherein measured heart activity is received from a plurality of test individuals, and wherein the quiescent segments are non-overlapping time periods of lowest median HR for each test individual.

5. The method of claim 4, wherein the classifier is trained using features determined from a median quiescent segment for each test individual.

6. The method of claim 1, wherein the features include one or more of deceleration capacity (DC), low frequency (LF) power, very low frequency (VLF) power, and standard deviation of all normal RR intervals (SDNN), individually or in combination.

7. The method of claim 1, wherein the features include one or more of acceleration capacity (AC), deceleration capacity (DC), total power, and standard deviation of all normal RR intervals (SDNN), individually or in combination.

8. The method of claim 7, wherein phase-rectified signal averaging (PRSA) is performed to quantify the AC, the DC, or both.

9. The method of claim 1, wherein the features include at least one of a mode, a median, a standard deviation, an interquartile range, a skewness, or a kurtosis of RR intervals.

10. The method of claim 1, further comprising selecting at least one quiescent segment from the measured heart rate activity information.

11. The method of claim 1, wherein the classifier is based on logistic regression.

12. The method of claim 1, wherein the measured heart activity is electrocardiography or photoplethysmography.

13. The method of claim 1, wherein one or more of the quiescent segments are from a time period during which the individual is asleep.

14. One or more non-transitory computer readable media storing computer-executable instructions that, when executed by one or more processors, cause the one or more processors to perform operations comprising:
 comparing one or more features from electrocardiography information received from an individual to a classifier, wherein the electrocardiography information comprises a plurality of RR intervals and one or more quiescent segments, and wherein at least one of the features is based on at least one quiescent segment;
 determining a posttraumatic stress disorder (PTSD) status based on the comparison of the features to the classifier; and
 outputting the PTSD status.

15. The one or more non-transitory computer readable media of claim 14, wherein one or more of the quiescent segments are from a time period during which the individual is asleep.

16. A monitoring system for determining a posttraumatic stress disorder (PTSD) indicator, the monitoring system including one or more electronic processing devices that:
 obtain subject data from a biological subject indicative of a measured heart activity for the biological subject over a period of time;
 analyze the subject data to determine one or more quiescent segments of the period of time using the heart activity;
 analyze the subject data to determine at least one feature relating to the heart activity during a quiescent segment;
 apply the at least one feature to at least one computational model to determine a posttraumatic stress disorder (PTSD) indicator indicative of a PSTD status of the biological subject, the computational model embodying a relationship between PSTD and one or more features, the computational model being obtained by applying machine learning to test features derived from measured heart activity for one or more test subjects during at least part of test quiescent segments of a test period of time.

17. The monitoring system of claim 16, wherein the one or more processing devices, determine the quiescent segment at least one of:
 from a period during which the subject was awake;
 from a period during which the subject was asleep;
 from a median quiescent segment; and,
 from one or more non-overlapping 10-minute periods of lowest median HR or lowest average heartrate.

18. The monitoring system of claim 16, wherein the features include one or more of:
 a heart rate statistic feature selected from a heart rate statistic group including:
  a mean;
  a median;
  an average;
  a variance;
  a skew;
  a kurtosis;
  a percentile;
  a cumulative distribution function;
 a heart rate spectral power feature indicative of a spectral power in at least one frequency band selected from a frequency band group including:
  an ultra low frequency less than about 0.003 Hz;
  a very low frequency between about 0.003 Hz and about 0.04 Hz;
  a low frequency between about 0.04 Hz and about 0.15 Hz;
  a high-frequency between about 0.15 Hz and about 0.4 Hz;
 a heart rate variability feature selected from a heart rate variability group including:
  a multi-scale entropy;
  a standard deviation of average pulse intervals; and,
  square root of the mean of the squares of differences between adjacent pulse intervals;
 acceleration capacity (AC); and,
 deceleration capacity (DC).

19. The monitoring system of claim 18, wherein phase-rectified signal averaging (PRSA) is performed to quantify the AC, the DC, or both.

20. The monitoring system of claim 16, wherein the one or more processing devices:
 determine one or more subject attributes from the subject data; and,
 use the one or more subject attributes to apply the computational model so that the at least one feature is assessed based on reference features derived for one or more test subjects having similar attributes to the subject attributes.

21. The monitoring system of claim 16, wherein the system includes a monitoring device including:
 at least one sensor; and,
 a monitoring device processor that generates sensor data in accordance with signals from the at least one sensor, the sensor data being indicative of at least the heart activity of the subject.

22. The monitoring system of claim 16, wherein the monitoring system performs electrocardiography.

* * * * *